United States Patent
Lee et al.

(10) Patent No.: US 11,980,091 B2
(45) Date of Patent: May 7, 2024

(54) ORGANIC ELECTROLUMINESCENCE DEVICE AND COMPOUND FOR ORGANIC ELECTROLUMINESCENCE DEVICE

(71) Applicants: Samsung Display Co., Ltd., Yongin-si (KR); Lapto Co., Ltd., Seongnam-si (KR)

(72) Inventors: Dongchan Lee, Sejong-si (KR); Eu-gene Oh, Seoul (KR); SeulOng Kim, Hwaseong-si (KR); Yunjee Park, Asan-si (KR); Munsoo Kim, Seongnam-si (KR); JuWan Maeng, Seongnam-si (KR); Kap-jong Han, Gwangju-si (KR)

(73) Assignees: Samsung Display Co., Ltd., Yongin-si (KR); Lapto Co., Ltd., Seongnam-si (KR)

( * ) Notice: Subject to any disclaimer, the term of this patent is extended or adjusted under 35 U.S.C. 154(b) by 486 days.

(21) Appl. No.: 17/023,189

(22) Filed: Sep. 16, 2020

(65) Prior Publication Data

US 2021/0098711 A1    Apr. 1, 2021

(30) Foreign Application Priority Data

Sep. 30, 2019   (KR) .................. 10-2019-0121044

(51) Int. Cl.
*H10K 85/60* (2023.01)
*C07D 498/04* (2006.01)
(Continued)

(52) U.S. Cl.
CPC ......... *H10K 85/657* (2023.02); *C07D 498/04* (2013.01); *C07D 513/04* (2013.01);
(Continued)

(58) Field of Classification Search
CPC .............. H10K 86/657; H10K 86/636; H10K 86/6572; H10K 50/11; H10K 2102/10;
(Continued)

(56) References Cited

U.S. PATENT DOCUMENTS 8,093,399 B2    1/2012  Nomura et al.
8,383,932 B2 *  2/2013  Jung ..................... C09B 57/00
                                                        546/256

(Continued)

FOREIGN PATENT DOCUMENTS

CN    102574848 A       7/2012
CN    105294670 A   *   2/2016   ........... C07D 413/14
(Continued)

OTHER PUBLICATIONS

Examination report Jul. 20, 2023 from the Chinese Patent Office in respect of the Chinese Patent Application 202010995172.2, 8pp.
(Continued)

*Primary Examiner* — Michael M. Bernshteyn
(74) *Attorney, Agent, or Firm* — Lewis Roca Rothgerber Christie LLP

(57) ABSTRACT

An organic electroluminescence device of an embodiment includes a first electrode, a second electrode, and an emission layer between the first electrode and the second electrode, and the emission layer includes a compound represented by Formula 1 below, and thus the organic electroluminescence device may exhibit high luminous efficiency characteristics and improved service life characteristics.

(Continued)

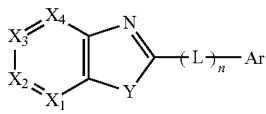

Formula 1

20 Claims, 2 Drawing Sheets

(51) Int. Cl.
| | |
|---|---|
| *C07D 513/04* | (2006.01) |
| *C09K 11/02* | (2006.01) |
| *C09K 11/06* | (2006.01) |
| *H10K 50/11* | (2023.01) |
| *H10K 101/10* | (2023.01) |

(52) U.S. Cl.
CPC .............. *C09K 11/02* (2013.01); *C09K 11/06* (2013.01); *H10K 85/636* (2023.02); *H10K 85/6572* (2023.02); *C09K 2211/1007* (2013.01); *C09K 2211/1018* (2013.01); *H10K 50/11* (2023.02); *H10K 2101/10* (2023.02)

(58) Field of Classification Search
CPC . C09K 11/02; C09K 11/06; C09K 2311/1018; C09K 2311/1007; C07D 498/04; C07D 513/04
USPC .......................................................... 428/690
See application file for complete search history.

(56) References Cited

U.S. PATENT DOCUMENTS

| | | | |
|---|---|---|---|
| 8,785,636 B2 | 7/2014 | Parham et al. | |
| 9,793,492 B2 | 10/2017 | Sagara et al. | |
| 10,069,082 B2 * | 9/2018 | Ren ...................... | C07D 471/04 |
| 2015/0239880 A1 * | 8/2015 | Adachi ................ | C07D 413/10 |
| | | | 544/102 |
| 2019/0067593 A1 * | 2/2019 | Cho ........................ | H10K 50/18 |
| 2019/0252621 A1 * | 8/2019 | Kabasawa ............ | C07D 471/04 |
| 2020/0203630 A1 * | 6/2020 | Park ...................... | H10K 85/631 |
| 2021/0098701 A1 | 4/2021 | Lee et al. | |
| 2021/0098708 A1 | 4/2021 | Kim et al. | |
| 2021/0098715 A1 * | 4/2021 | Kim ...................... | H10K 85/631 |

FOREIGN PATENT DOCUMENTS

| | | | | |
|---|---|---|---|---|
| CN | 105294670 A | | 2/2016 | |
| CN | 105481845 A | * | 4/2016 | |
| CN | 105481845 A | | 4/2016 | |
| CN | 111333615 A | * | 6/2020 | ........... C07D 401/10 |
| CN | 111333615 A | | 6/2020 | |
| KR | 10-1117621 B1 | | 3/2012 | |
| KR | 10-2015-0050570 A | | 5/2015 | |
| KR | 10-1670036 B1 | | 10/2016 | |
| KR | 10-2017-0044821 A | | 4/2017 | |
| KR | 10-2017-0050048 A | | 5/2017 | |
| KR | 10-2018-0117650 A | | 10/2018 | |
| KR | 10-2019-0026796 A | | 3/2019 | |
| KR | 10-2021-0038785 A | | 4/2021 | |

OTHER PUBLICATIONS

Examination report for corresponding CN Application No. 202010995172.2, dated Jan. 8, 2024, 9pp.

* cited by examiner

ORGANIC ELECTROLUMINESCENCE DEVICE AND COMPOUND FOR ORGANIC ELECTROLUMINESCENCE DEVICE

CROSS-REFERENCE TO RELATED APPLICATION

This application claims priority to and the benefit of Korean Patent Application No. 10-2019-0121044, filed on Sep. 30, 2019, the entire contents of which are incorporated herein by reference.

BACKGROUND

1. Field

Embodiments of the present disclosure relate to an organic electroluminescence device and a compound used for the same, and for example, to a compound used as a luminescence material and an organic electroluminescence device including the same.

2. Description of the Related Art

Recently, the development of an organic electroluminescence display as an image display is being actively conducted. The organic electroluminescence display is referred to as a self-luminescent display, which is different from a liquid crystal display, and in which holes and electrons injected from a first electrode and a second electrode recombine in an emission layer, and thus, a luminescence material including an organic compound in the emission layer emits light to provide a display.

In the application of an organic electroluminescence device to a display, a low driving voltage, high luminous efficiency, and long service life of the organic electroluminescence device are beneficial, and development of materials for the organic electroluminescence device which is capable of stably attaining the beneficial features is being continuously investigated.

Recently, a technology utilizing phosphorescent luminescence from energy in a triplet state to implement a high-efficient organic electroluminescence display, or a delayed fluorescence emitting using a phenomenon, which generates singlet excitons by colliding triplet excitons (Triplet-triplet annihilation, TTA) is being developed, and development of a thermally activated delayed fluorescence (TADF) material using a delayed fluorescent luminescence phenomenon is being conducted.

SUMMARY

Embodiments of the present disclosure provide an organic electroluminescence device exhibiting excellent luminous efficiency and long service life characteristics.

Embodiments of the present disclosure also provide a compound which is a material for an organic electroluminescence device having high efficiency and long service life characteristics.

An embodiment of the present disclosure provides a compound represented by the following Formula 1.

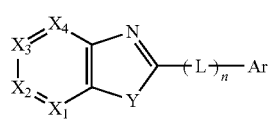

Formula 1

In Formula 1, at least one selected from among $X_1$ to $X_4$ is N, the rest are $CR_a$, Y is O or S, and n is 1 or 2. L is a substituted or unsubstituted arylene group having 6 to 30 carbon atoms for forming a ring, or a substituted or unsubstituted heteroarylene group having 2 to 30 carbon atoms for forming a ring. $R_a$ is a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or is combined with an adjacent group to form a ring, and Ar is represented by the following Formula 2.

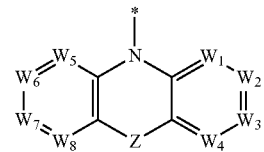

Formula 2

In Formula 2, $W_1$ to $W_8$ are each independently N or $CR_b$, Z is a direct linkage (e.g., a single bond), O, or $CR_cR_d$, and $R_b$ to $R_d$ are each independently a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or are combined with an adjacent group to form a ring.

Formula 1 above may be represented by the following Formula 1-1 or Formula 1-2:

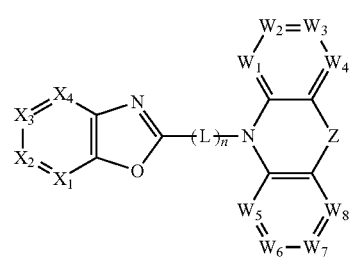

Formula 1-1

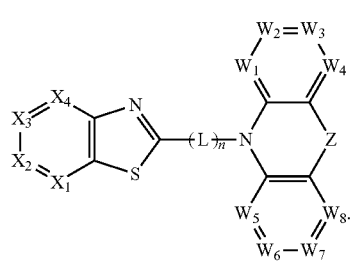

Formula 1-2

In Formula 1-1 and Formula 1-2, $X_1$ to $X_4$, L, n, Z, $W_1$ to $W_8$ may be the same as those defined with respect to Formula 1 and Formula 2 above.

Any one selected from among $X_1$ to $X_4$ may be N, the rest may be $CR_a$, or $X_1$ and $X_4$ may be each independently N, and the rest may be $CR_a$, and $R_a$ may be represented by a hydrogen atom, or any one selected from the following $R_a$-1 to $R_a$-4 below.

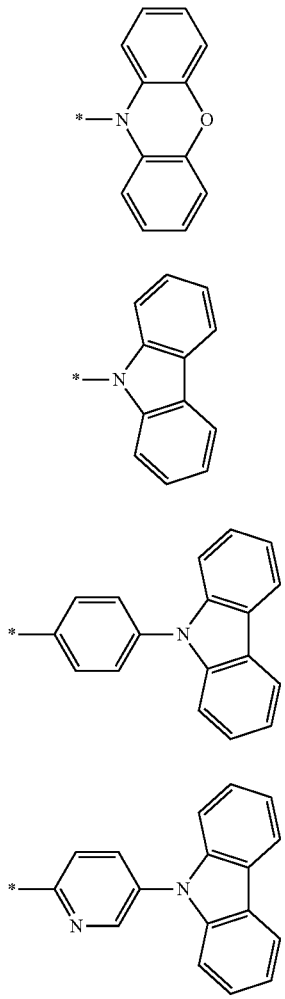

Formula 2 above may be represented by any one selected from the following Formula 2-1 to Formula 2-4.

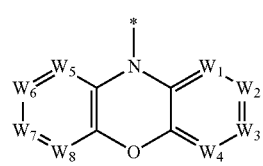

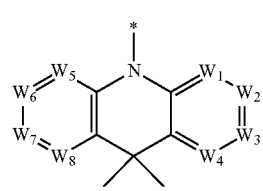

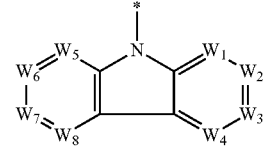

Formula 2-3

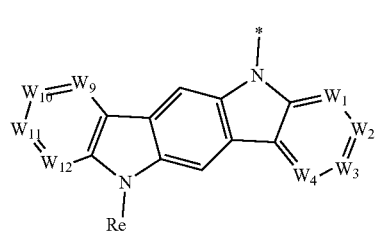

Formula 2-4

In Formula 2-4, $R_e$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring. $W_9$ to $W_{12}$ may be each independently N or $CR_f$, and $R_f$ may be a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring. In Formula 2-1 to Formula 2-4, $W_1$ to $W_8$ may be the same as those defined with respect to Formula 2 above.

Ar may be represented by any one selected from the following Ar-1 to Ar-6.

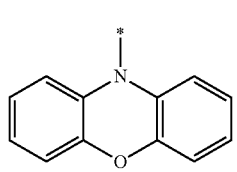

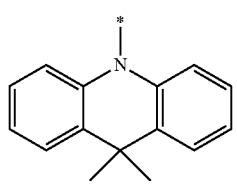

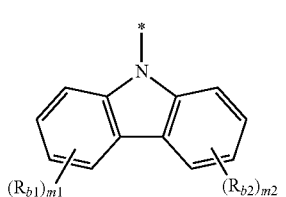

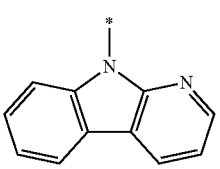

Ar-5

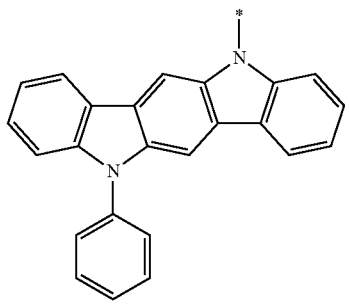

Ar-6

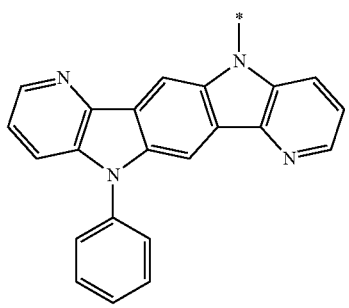

In Ar-3 above, m1 and m2 may be each independently 0 or 1, $R_{b1}$ and $R_{b2}$ may be each independently a hydrogen atom, a deuterium atom, a substituted or unsubstituted arylamine group having 6 to 30 carbon atoms for forming a ring, or a substituted or unsubstituted aryl group having 6 to 30 carbon atoms for forming a ring.

L may be represented by any one the following L-1 to L-5.

L-1

*—⟨phenylene⟩—*

L-2

*—⟨pyridylene⟩—*

L-3

*—⟨phenyl-phenyl⟩—*

L-4

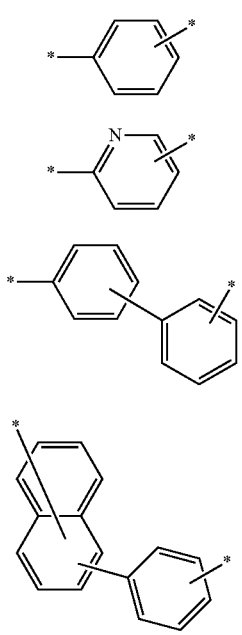

L-5

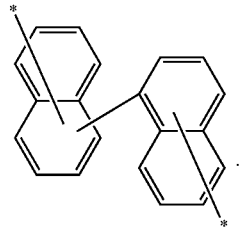

The compound represented by Formula 1 may be a green dopant to emit a green light having a center wavelength (e.g., a central wavelength) of 500 nm or more and 550 nm or less.

The compound represented by Formula 1 may be a blue dopant to emit a blue light having a center wavelength (e.g., a central wavelength) of 450 nm or more and less than 500 nm.

The compound represented by Formula 1 may be a host material.

In the compound represented by Formula 1, the absolute value $\Delta E_{ST}$ of a difference between a lowest singlet excitation energy level (S1) and a lowest triplet excitation energy level (T1) may be 0.2 eV or less.

In an embodiment of the present disclosure, an organic electroluminescence device includes: a first electrode; a second electrode on the first electrode; and an emission layer which is between the first electrode and the second electrode, and the emission layer includes the compound of an embodiment described above.

The emission layer may include a host and a dopant, and the host may include the compound.

The emission layer may emit a delayed fluorescence, and the compound may be a delayed fluorescence dopant.

The emission layer may emit light having a center wavelength (e.g., a central wavelength) of 500 nm to 550 nm, or light having a center wavelength (e.g., a central wavelength) of 450 nm to 500 nm (exclusive of 500 nm).

BRIEF DESCRIPTION OF THE DRAWINGS

The accompanying drawings are included to provide a further understanding of the subject matter of the present disclosure, and are incorporated in and constitute a part of this specification. The drawings illustrate exemplary embodiments of the present disclosure and, together with the description, serve to explain principles of the present disclosure. In the drawings.

DETAILED DESCRIPTION

Figure 1:
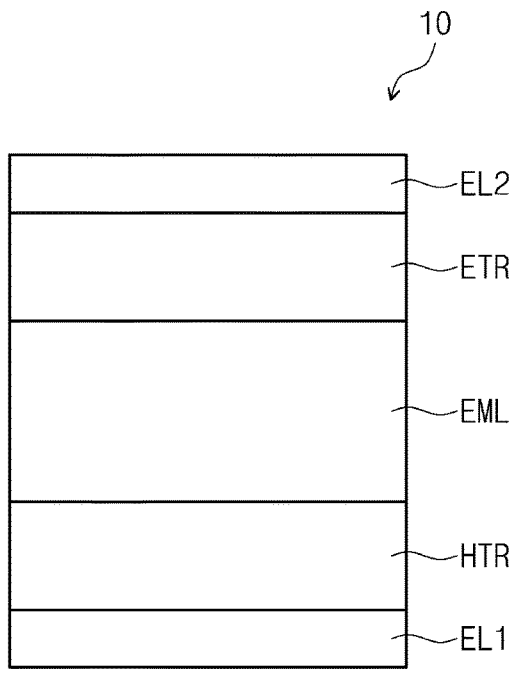
FIG. 1 is a cross-sectional view schematically illustrating an organic electroluminescence device according to an embodiment of the present disclosure.

Because an embodiment of the present disclosure may have various modifications and diverse shapes, only certain embodiments are illustrated in the drawings and described in the detailed description. However, this does not intend to limit the present disclosure to particular embodiments, and it should be understood that the present disclosure covers all the modifications, equivalents, and replacements within the spirit and technical scope of the present disclosure.

In this specification, it will also be understood that when a component (a region, a layer, a portion, or the like) is referred to as "being on," "being connected to," or "being coupled to" another component, it may be directly on/connected/coupled to the other component, or an intervening third component may be also therebetween.

Like reference symbols refer to like elements throughout. Also, in the drawing, the thicknesses, dimensions, and ratios of the components may be exaggerated for effectively describing the technical features of the subject matter of the present disclosure.

As used herein, the term "and/or" includes any and all combinations of one or more of the associated listed items.

Although the terms such as "first" and "second" are used herein to describe various components, these components should not be limited by these terms. The terms are only used to distinguish one component from other components. For example, a first component may be referred to as a second component, and similarly a second component may be referred to as a first component without departing from the scope of the present disclosure. The expression of a singular form may include plural forms unless definitely indicating a particular case in terms of the context.

Also, terms such as "below", "in lower side", "above", "in upper side", and the like may be used to describe the relationships of the components illustrated in the drawings. These terms are relative concepts, and are described on the basis of the directions illustrated in the drawings, but the present disclosure is not limited thereto.

Unless otherwise defined, all terms (including technical and scientific terms) used herein have the same meaning as commonly understood by one of ordinary skill in the art to which the subject matter of the present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be understood that the meaning of "comprise" or "have" specifies the presence of a feature, a fixed number, a step, a process, an element, a component, or a combination thereof disclosed in the specification, but does not exclude the possibility of presence or addition of one or more other features, fixed numbers, steps, processes, elements, components, or combination thereof.

Hereinafter, an organic electroluminescence device according to an embodiment of the present disclosure and a compound included in the same according to an embodiment will be explained referring to drawings.

FIG. 1 to 4 are a cross-sectional view schematically illustrating an organic electroluminescence device according to an embodiment of the present disclosure. Referring to FIG. 1 to 4, in an organic electroluminescence device 10 according to an embodiment of the present disclosure, a first electrode EL1 and a second electrode EL2 face each other, and an emission layer EML may be between the first electrode EL1 and the second electrode EL2.

Furthermore, the organic electroluminescence device 10 of an embodiment further includes a plurality of functional layers between the first electrode EL1 and the second electrode EL2 as well as the emission layer EML. The plurality of functional layers may include a hole transport region HTR, and an electron transport region ETR. For example, the organic electroluminescence device 10 according to an embodiment of the present disclosure may include a first electrode EL1, a hole transport region HTR, an emission layer EML, an electron transport region ETR, and a second electrode EL2 which are laminated sequentially. In addition, the organic electroluminescence device 10 of an embodiment may include a capping layer CPL on the second electrode EL2.

The organic electroluminescence device 10 of an embodiment may include a compound according to an embodiment described below in the emission layer EML between the first electrode EL1 and the second electrode EL2. However, embodiments are not limited thereto, and the organic electroluminescence device 10 of an embodiment may include a compound according to an embodiment described below in the hole transport region HTR and/or the electron transport region ETR which is one of the plurality of functional layers between the first electrode EL1 and the second electrode EL2, as well as in the emission layer EML.

Figure 2:
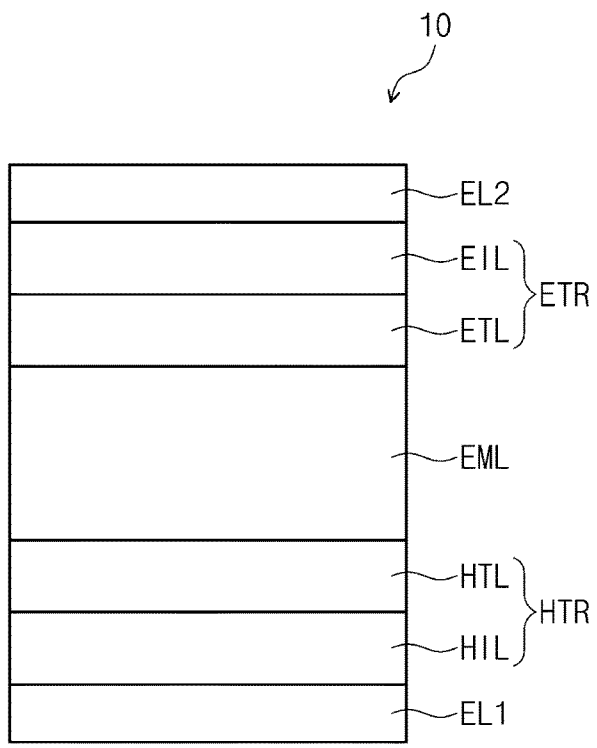
FIG. 2 is a cross-sectional view schematically illustrating an organic electroluminescence device according to an embodiment of the present disclosure.
Figure 3:
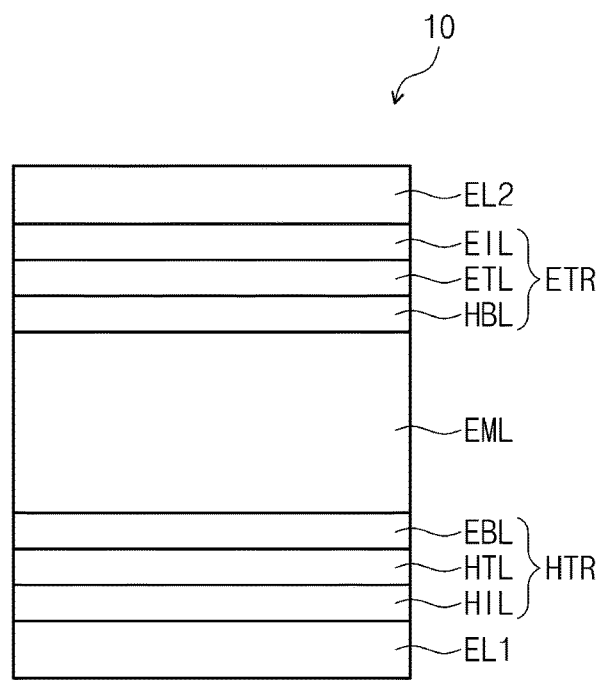
FIG. 3 is a cross-sectional view schematically illustrating an organic electroluminescence device according to an embodiment of the present disclosure.
Figure 4:
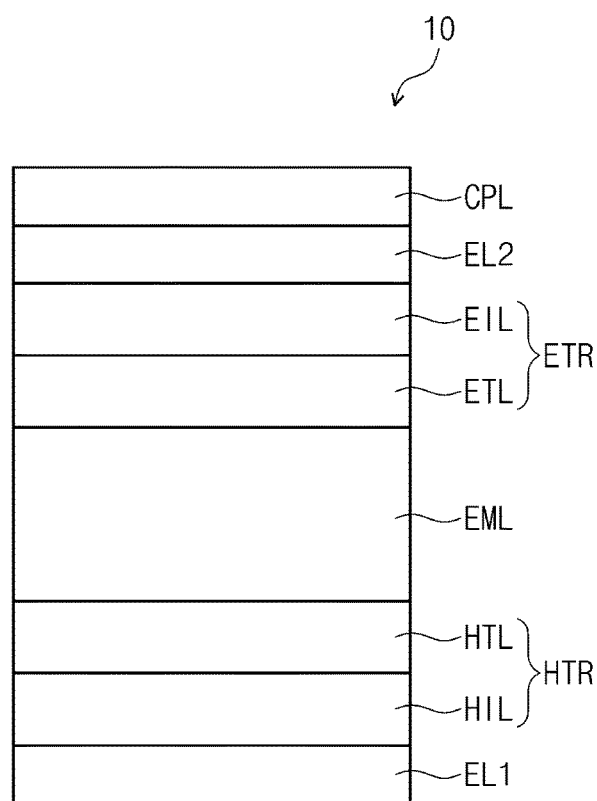
FIG. 4 is a cross-sectional view schematically illustrating an organic electroluminescence device according to an embodiment of the present disclosure.

When compared with FIG. 1, FIG. 2 shows a cross-sectional view of an organic electroluminescence device 10 of an embodiment, wherein the hole transport region HTR includes a hole injection layer HIL and a hole transport layer HTL, and the electron transport region ETR includes an electron injection layer EIL and an electron transport layer ETL. Furthermore, when compared with FIG. 1, FIG. 3 shows a cross-sectional view of an organic electroluminescence device 10 of an embodiment, wherein the hole transport region HTR includes a hole injection layer HIL, a hole transport layer HTL, and an electron blocking layer EBL, the electron transport region ETR includes an electron injection layer EIL, an electron transport layer ETL, and a hole blocking layer HBL. When compared with FIG. 2, FIG. 4 shows a cross-sectional view of an organic electroluminescence device 10 of an embodiment including the capping layer CPL on the second electrode EL2.

The first electrode EL1 has conductivity (e.g., electrical conductivity). The first electrode EL1 may be formed of a metal alloy or a conductive compound. The first electrode EL1 may be an anode. In addition, the first electrode EL1 may be a pixel electrode. The first electrode EL1 may be a transmissive electrode, a transflective electrode, or a reflective electrode. When the first electrode EL1 is the transmissive electrode, the first electrode EL1 may include a transparent metal oxide, for example, indium tin oxide (ITO), indium zinc oxide (IZO), zinc oxide (ZnO), or indium tin zinc oxide (ITZO). When the first electrode EL1 is the transflective electrode or the reflective electrode, the first electrode EL1 may include Ag, Mg Cu, Al, Pt, Pd, Au, Ni, Nd, Ir, Cr, Li, Ca, LiF/Ca, LiF/Al, Mo, Ti, or a compound or mixture (e.g., a mixture of Ag and Mg) thereof. In some embodiments, the first electrode EL1 may have a multi-layered structure including a reflective layer or transflective layer and a transparent conductive layer formed of indium tin oxide (ITO), indium zinc oxide (IZO), zinc oxide (ZnO), or indium tin zinc oxide (ITZO). For example, the first electrode EL1 may have, but is not limited to, a three-layer structure of ITO/Ag/ITO. The first electrode EL1 may have a thickness of about 1,000 Å to about 10,000 Å, for example, of about 1,000 Å to about 3,000 Å.

The hole transport region HTR is provided on the first electrode EL1. The hole transport region HTR may include at least one selected from among a hole injection layer HIL, a hole transport layer HTL, a hole buffer layer, and an electron blocking layer EBL. The hole transport region HTR may have a thickness, for example, of about 50 Å to about 15,000 Å.

The hole transport region HTR may have a multilayer structure having a single layer formed of a single material, a single layer formed of materials different from each other, or a plurality of layers formed of materials different from each other.

For example, the hole transport region HTR may have a single layer structure of a hole injection layer HIL or a hole transport layer HTL, or a single layer structure formed of a hole injection material or a hole transport material. In addition, the hole transport region HTR has a single layer structure formed of materials different from each other, or a structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL which are sequentially laminated from the first electrode EL1, but embodiments are not limited thereto.

The hole transport region HTR may be formed by using various suitable methods such as a vacuum deposition method, a spin coating method, a casting method, a Langmuir-Blodgett (LB) method, an inkjet printing method, a laser printing method, and/or a laser induced thermal imaging (LITI) method.

The hole injection layer HIL may include, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-[tris(3-methylphenyl)phenylamino]triphenylamine] (m-MTDATA), 4,4',4"-tris(N,N-diphenylamino)triphenylamine (TDATA), 4,4',4"-tris{N,-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalenyl)-N,N'-diphenyl-benzidine (NPB), triphenylamine-containing polyetherketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL may further include, for example, carbazole derivatives such as N-phenyl carbazole and polyvinyl carbazole, fluorene derivatives, N,N'-bis(3-methylphenyl)-N,N'-diphenyl-[1,1-biphenyl]-4,4'-diamine (TPD), triphenylamine derivatives such as 4,4',4"-tris(N-carbazolyl)triphenylamine (TCTA), N,N'-di(naphthalenyl)-N,N'-diphenyl-benzidine (NPB), 4,4'-cyclohexylidene bis [N,N-bis(4-methylphenyl)benzenamine] (TAPC), 4,4'-bis [N,N'-(3-tolyl)amino]-3,3'-dimethylbiphenyl (HMTPD), 1,3-Bis(N-carbazolyl)benzene (mCP), etc.

The hole transport region HTR may have a thickness of about 50 Å to about 10,000 Å, for example, of about 100 Å to about 5,000 Å. The hole injection layer HIL may have a thickness, for example, of about 30 Å to about 1,000 Å, the hole transport layer HTL may have a thickness of about 30 Å to about 1,000 Å. For example, the electron blocking layer EBL may have a thickness of about 10 Å to about 1,000 Å. When the thickness of each of the hole transport region HTR, the hole injection layer HIL, the hole transport layer HTL, and the electron blocking layer EBL satisfies the above-described range, suitable or satisfactory hole transport characteristics may be achieved without a substantial increase in driving voltage.

The hole transport region HTR may further include a charge generating material in addition to the above-described materials to improve conductivity (e.g., electrical conductivity). The charge generating material may be uniformly or non-uniformly dispersed into the hole transport region HTR. The charge generating material may be, for example, a p-dopant. The p-dopant may be one selected from quinone derivatives, metal oxides, and cyano group-containing compounds, but is not limited thereto. For example, non-limiting examples of the p-dopant may include, but are not limited to, quinone derivatives such as tetracyanoquinodimethane (TCNQ) and 2,3,5,6-tetrafluoro-7,7,8,8-tetracyanoquinodimethane (F4-TCNQ), and metal oxides such as tungsten oxides and molybdenum oxides.

As described above, the hole transport region HTR may further include at least one of the hole buffer layer or the electron blocking layer EBL in addition to the hole injection layer HIL and the hole transport layer HTL. The hole buffer layer may compensate a resonance distance according to the wavelength of light emitted from the emission layer EML to increase light emission efficiency. A material that may be contained in the hole transport layer may be used as a material to be contained in the hole buffer layer. The electron blocking layer EBL is a layer that blocks or reduces electron injection from the electron transport region ETR to the hole transport region HTR.

The emission layer EML is on the hole transport region HTR. The emission layer EML may have a thickness, for example, of about 100 Å to about 1,000 Å, or of about 100 Å to about 400 Å. The emission layer EML may have a multilayer structure having a single layer formed of a single material, a single layer formed of materials different from each other, or a plurality of layers formed of materials different from each other.

The emission layer EML in the organic electroluminescence device 10 of an embodiment may include a compound of an embodiment.

In the present description, the term "substituted or unsubstituted" may refer to being substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents may be substituted or unsubstituted. For example, a biphenyl group may be interpreted as an aryl group or a phenyl group substituted with a phenyl group.

In the present description, the expression "being bonded to an adjacent group to form a ring" may mean being bonded to an adjacent group to form a substituted or unsubstituted hydrocarbon ring, or a substituted or unsubstituted heterocyclic ring. The hydrocarbon ring includes an aliphatic hydrocarbon ring and an aromatic hydrocarbon ring. The heterocyclic ring includes an aliphatic heterocyclic ring and an aromatic heterocyclic ring. A ring formed by bonding adjacent groups to each other may be a single ring or a multiple ring (e.g., a polycyclic structure including a plurality of rings). In addition, a ring formed by being bonded to an adjacent group may be linked to another ring to form a spiro structure.

In the present description, the term "adjacent group" may mean a substituent which is substituted for an atom directly linked to an atom for which the substituent is substituted, another substituent which is substituted for an atom for which the substituent is substituted, or a substituent sterically closest to the substituent. For example, two methyl groups in 1,2-dimethylbenzene may be interpreted as "adjacent groups" to each other, and two ethyl groups in 1,1-diethylcyclopentane may be interpreted as "adjacent groups" to each other.

In the present description, examples of the halogen atom may include a fluorine atom, a chlorine atom, a bromine atom, and an iodine atom.

In the present description, the alkyl group may be a linear, branched or cyclic alkyl group. The number of carbons in the alkyl group is 1 to 50, 1 to 30, 1 to 20, 1 to 10, or 1 to 6. Examples of the alkyl group may include, but are not limited to, methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the present description, the number of carbons for forming a ring of the hydrocarbon ring may be 5 to 60, 5 to 30, or 5 to 20 of an aliphatic hydrocarbon ring or an aromatic hydrocarbon ring. The hydrocarbon ring group may be any suitable functional group or substituent derived from an aliphatic hydrocarbon ring, or any suitable functional group or substituent derived from an aromatic hydrocarbon ring. The number of carbons for forming a ring of the hydrocarbon ring group may be 5 to 60, 5 to 30, or 5 to 20.

In the present description, the aryl group refers to an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Examples of the aryl group may include, but are not limited to, phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc.

In the present description, the heterocyclic group refers to an optional functional group or substituent derived a ring including one or more among B, O, N, P, Si, and S as a heteroatom. The heterocyclic ring includes an aliphatic heterocyclic ring and an aromatic heterocyclic ring. The aromatic heterocyclic group may be a heteroaryl group. The aliphatic heterocyclic ring and the aromatic heterocyclic ring may be monocyclic or polycyclic.

In the present description, the heterocyclic ring may include one or more among B, O, N, P, Si, and S as a heteroatom. In the case where the heterocyclic ring includes two or more heteroatoms, two or more heteroatoms may be the same as or different from each other. The heterocyclic ring may be a monocyclic heterocyclic ring or a polycyclic heterocyclic ring, and include a heteroaryl. The carbon number for forming a ring in the heterocyclic ring may be 2 to 30, 2 to 20, or 2 to 10.

In the present description, the aliphatic heterocyclic group may include one or more among B, O, N, P, Si, and S as a heteroatom. The number of carbons for forming a ring of the aliphatic heterocyclic group may be 2 to 30, 2 to 20, or 2 to 10. Examples of the aliphatic heterocyclic group may include, but are not limited to, oxirane, thiirane, pyrrolidine, piperidine, tetrahydrofuran, tetrahydrothiophene, thiane, tetrahydropyran, 1,4-dioxane, etc.

In the present description, the heteroaryl group may include one or more among B, O, N, P, Si, and S as a heteroatom. In the case where the heteroaryl group includes two or more heteroatoms, two or more heteroatoms may be the same as or different from each other. The heteroaryl group may be a monocyclic heterocyclic group or a polycyclic heterocyclic group. The number of carbons for forming a ring of the heteroaryl group may be 2 to 30, 2 to 20, or 2 to 10. Examples of the heteroaryl may include thiophenyl, furanyl, pyrrolyl, imidazolyl, thiazolyl, oxazolyl, oxadiazolyl, triazolyl, pyridinyl, bipyridinyl, pyrimidinyl, triazinyl, acridyl, pyridazinyl, pyrazinyl, quinolinyl, quinazolinyl, quinoxalinyl, phenoxazinyl, phthalazinyl, pyrido pyrimidinyl, pyrido pyrazinyl, pyrazino pyrazinyl, isoquinolinyl, indolyl, carbazolyl, N-arylcarbazolyl, N-heteroarylcarbazolyl, N-alkylcarbazolyl, benzoxazolyl, benzoimidazolyl, benzothiazolyl, benzocarbazolyl, benzothiophenyl, dibenzothiophenyl, thienothiophenyl, benzofuranyl, phenanthrolinyl, isooxazolyl, thiadiazolyl, phenothiazinyl, dibenzosilolyl, dibenzofuranyl, etc., without limitation.

In the present description, the carbon number of the amine group may be 1 to 30, but the present disclosure is not particularly limited thereto. The amine group may include an alkyl amine group and an aryl amine group. Examples of the amine group may include, but are not limited to, methylamine, dimethylamine, phenylamine, diphenylamine, naphthylamine, 9-methyl-anthracenylamine, triphenylamine, etc. For example, the alkyl group in the alkyl amine group is the same as the examples of the alkyl group described above, and the aryl group in the aryl amine group is the same as the examples of the aryl group described above.

In the present description, the term "direct linkage" may mean a single bond.

Meanwhile, in the present description, "―――*" means the position to be linked.

The emission layer EML in the organic electroluminescence device 10 of an embodiment may include a compound represented by Formula 1 below of an embodiment.

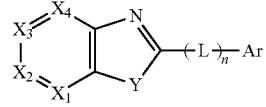

Formula 1

In Formula 1, at least one selected from among $X_1$ to $X_4$ is N, the rest are $CR_a$, and Y is O or S. For example, any one selected from among $X_1$ to $X_4$ may be N, the rest may be $CR_a$, or two selected from among $X_1$ to $X_4$ may be N, and the rest may be $CR_a$.

In some embodiments, the compound represented by Formula 1 of an embodiment may include Aza-type benzoxazole (e.g., an aza-benzoxazole), or Aza-type benzothiazole (e.g., an aza-benzothiazole).

The rest except for N in $X_1$ to $X_4$ may be $CR_a$, and $R_a$ may be a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring. For example, $R_a$ in $CR_a$ may be a substituted or unsubstituted aryl group having 6 to 20 carbon atoms for forming a ring, or a substituted or unsubstituted heteroaryl group having 2 to 20 carbon atoms for forming a ring, but embodiments are not limited thereto.

Any one selected from among $X_1$ to $X_4$ in the compound represented by Formula 1 of an embodiment may be N, the rest may be $CR_a$, or each of $X_1$ and $X_4$ may be N, and the rest may be $CR_a$. In this case, $R_a$ may be a hydrogen atom, or represented by any one selected from among $R_a$-1 to $R_a$-4.

$R_a$-1

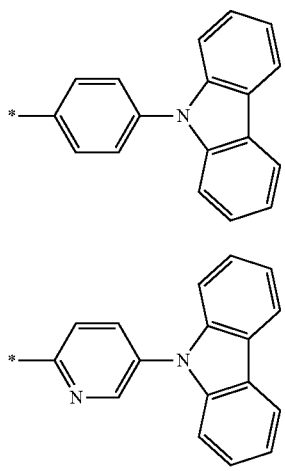

$R_a$-2

$R_a$-3

$R_a$-4

In some embodiments, when at least one selected from among $X_1$ to $X_4$ is N, and the rest is represented by $CR_a$, a plurality of $R_a$'s may be the same as each other or at least one of them may be different.

In Formula 1, n may be 1 or 2. In addition, L may be a substituted or unsubstituted arylene group having 6 to 30 carbon atoms for forming a ring, or a substituted or unsubstituted heteroarylene group having 2 to 30 carbon atoms for forming a ring group.

In Formula 1, L may be represented by any one selected from among L-1 to L-5 below.

L-1
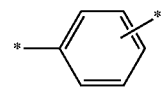

L-2
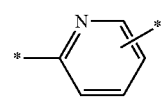

L-3
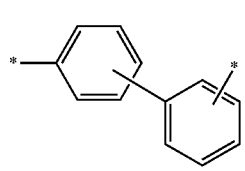

L-4
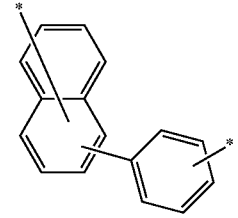

L-5
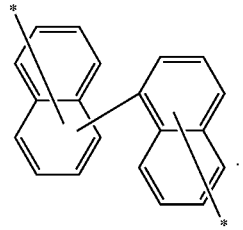

For example, in the compound represented by Formula 1 of an embodiment, a linker L may be a phenylene group, or a pyridylene group.

In the compound represented by Formula 1 of an embodiment, Ar may be represented by Formula 2 below.

Formula 2

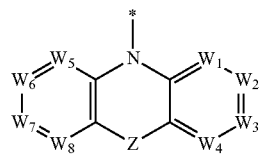

In Formula 2, $W_1$ to $W_8$ may be each independently N or $CR_b$, and Z may be a direct linkage (e.g., a single bond), O, or $CR_cR_d$. $R_b$ to $R_d$ may be each independently a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms, or a substituted or unsubstituted heteroaryl group having 2 to 30 carbon atoms for forming a ring, or may be combined with an adjacent group to form a ring.

For example, a plurality of neighboring $R_b$'s may be combined with each other to form a hydrocarbon ring or a heterocyclic ring. In some embodiments, the plurality of adjacent $R_b$'s may be combined with each other to form a ring including an indole site or an aza-indole site.

In an embodiment, Formula 2 may be represented by any one selected from among Formula 2-1 to Formula 2-4 below.

Formula 2-1

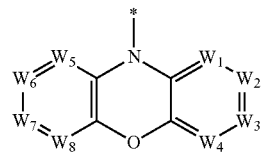

Formula 2-2

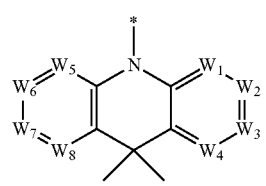

Formula 2-3

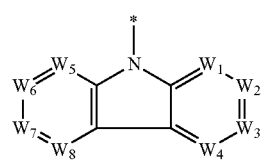

Formula 2-4

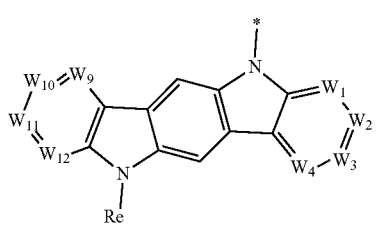

In Formula 2-4, $R_e$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring. For example, in Formula 2-4, $R_e$ may be a substituted or unsubstituted phenyl group.

In Formula 2-4, $W_9$ to $W_{12}$ may be each independently N or $CR_f$, and $R_f$ may be a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with an adjacent group to form a ring.

For example, Formula 1 may be represented by Formula 1-1 or Formula 1-2 below.

Formula 1-1

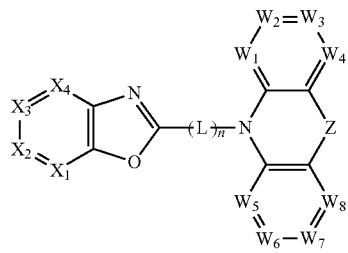

Formula 1-2

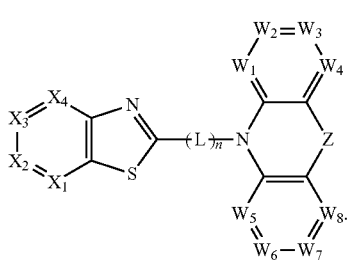

In Formula 1-1 and Formula 1-2, $X_1$ to $X_4$, n, and L may be the same as those defined with respect to Formula 1 above, and $W_1$ to $W_8$ and Z may be the same as those defined with respect to Formula 2 above.

In some embodiments, in Formula 1, Ar may be represented by any one selected from among Ar-1 to Ar-6. However, embodiments are not limited thereto, and heterocyclic compounds which includes N as an atom for forming a ring and in which an N atom is directly bound to a linker L may be variously provided as examples of Ar.

Ar-1

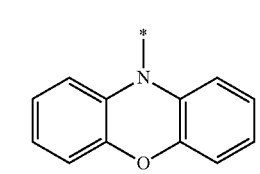

Ar-2

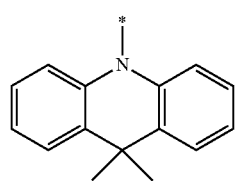

Ar-3

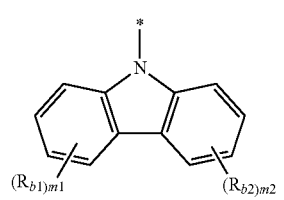

Ar-4

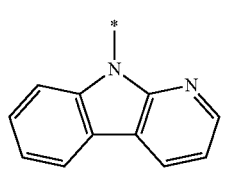

Ar-5

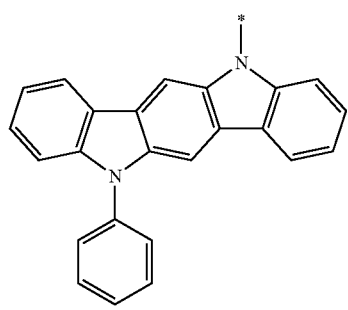

Ar-6

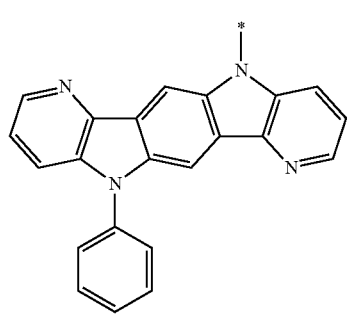

In some embodiments, in Ar-3 above, m1 and m2 are each independently 0 or 1, $R_{b1}$ and $R_{b2}$ are each independently a hydrogen atom, a deuterium atom, a substituted or unsubstituted arylamine group having 6 to 30 carbon atoms for forming a ring, or a substituted or unsubstituted aryl group having 6 to 30 carbon atoms for forming a ring. For example, $R_{b1}$ and $R_{b2}$ may be each independently a diphenylamine group or a phenyl group.

The compound of an embodiment may be any one selected from among compounds represented by Compound Group 1 and Compound Group 2 below. The organic electroluminescence device 10 of an embodiment may include at least one compound among the compounds represented by Compound Group 1 or Compound Group 2 in the emission layer EML.

Compound Group 1

1-1

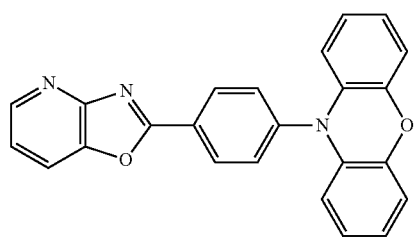

1-2

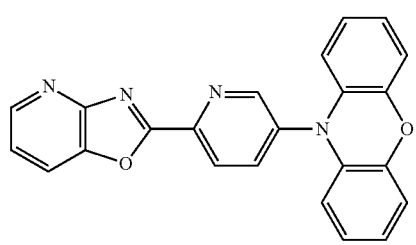

1-3

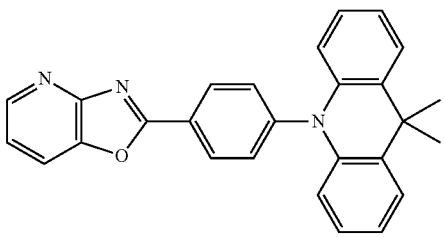

1-4

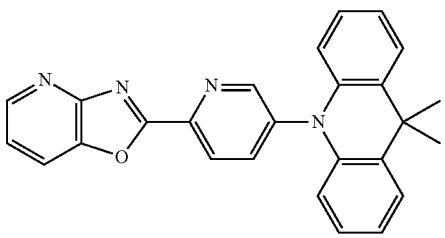

1-5

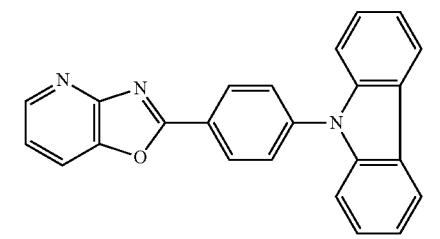

1-6

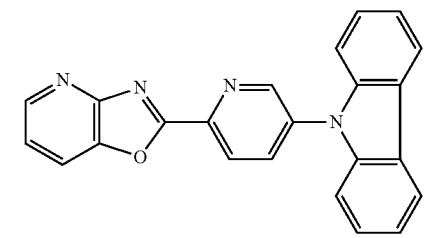

1-7

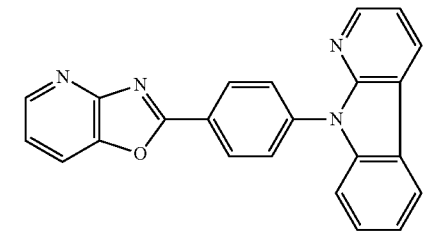

1-8

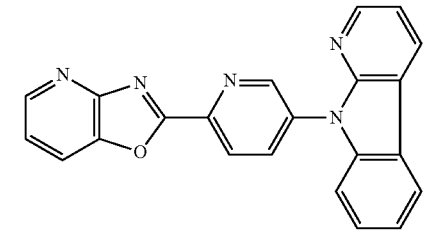

-continued
1-9
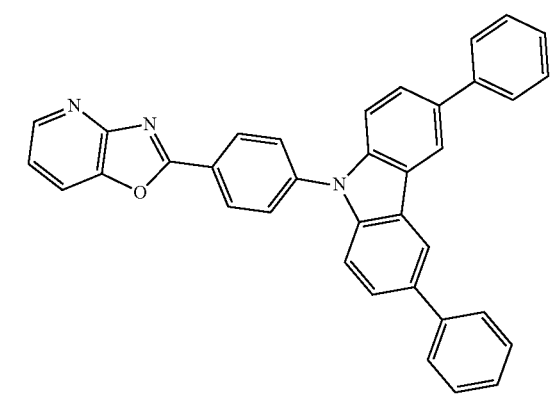
1-10
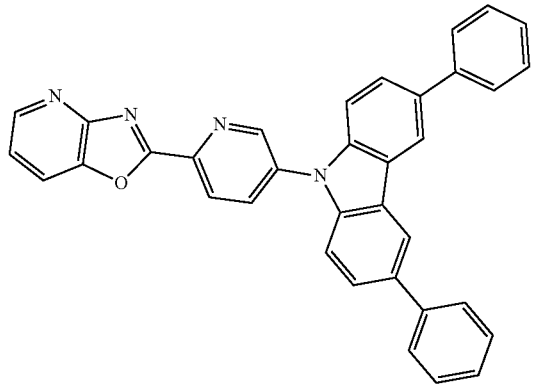
1-11
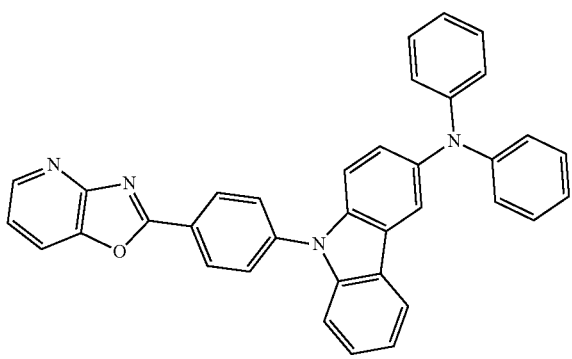
1-12
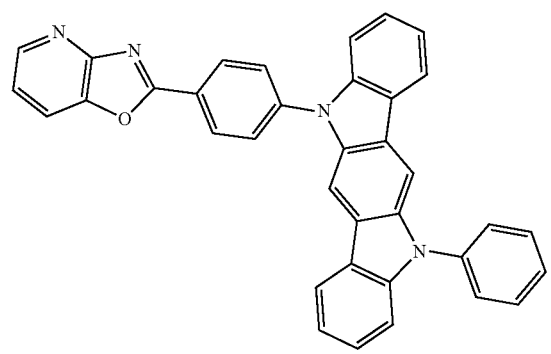
-continued
1-13
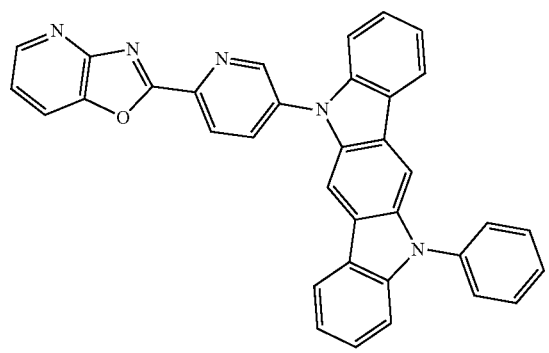
1-14
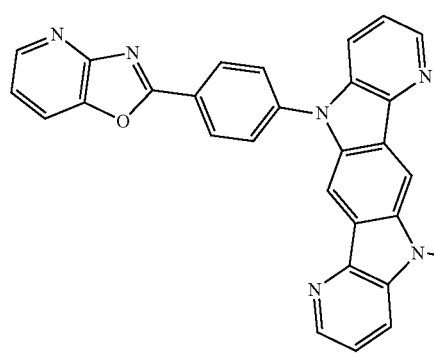
1-15
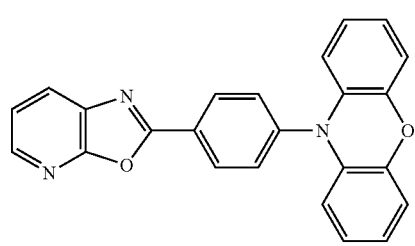
1-16
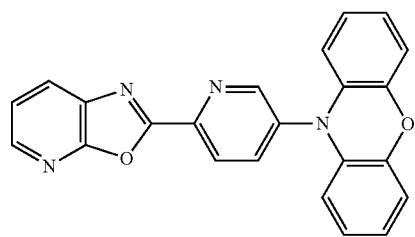
1-17
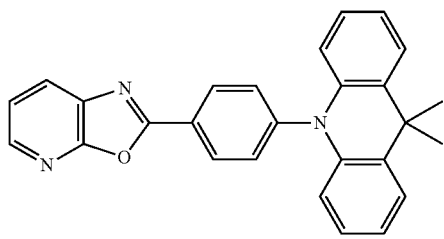

1-18
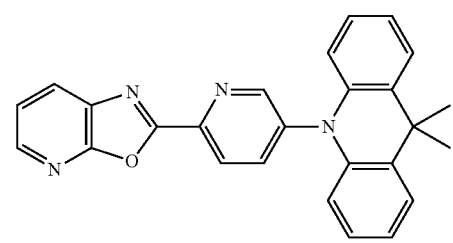
1-19
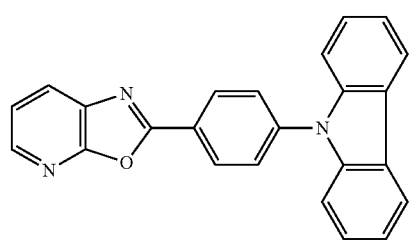
1-20
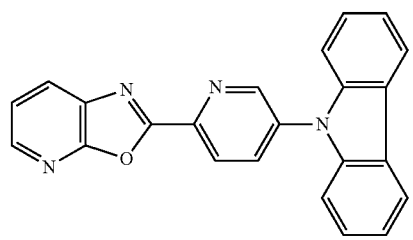
1-21
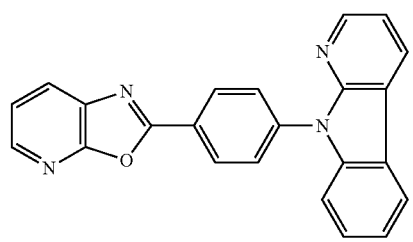
1-22
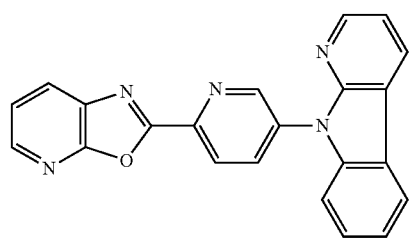
1-23
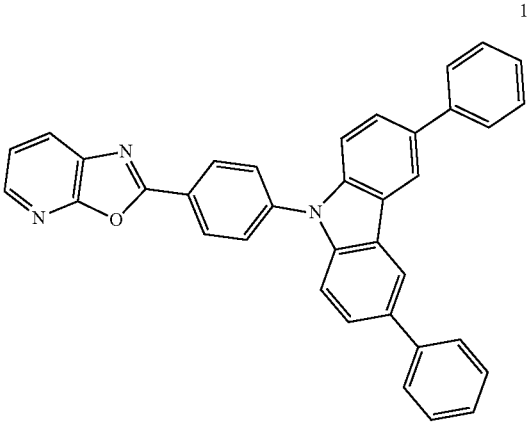
1-24
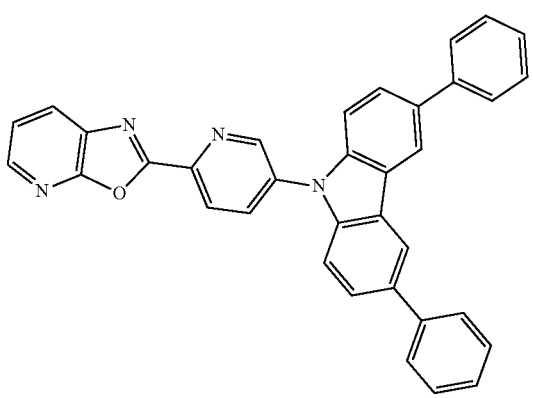
1-25
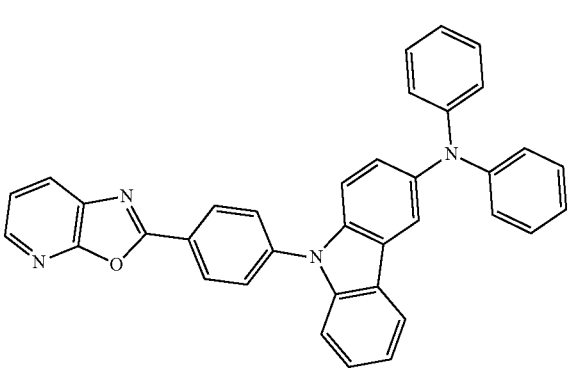
1-26
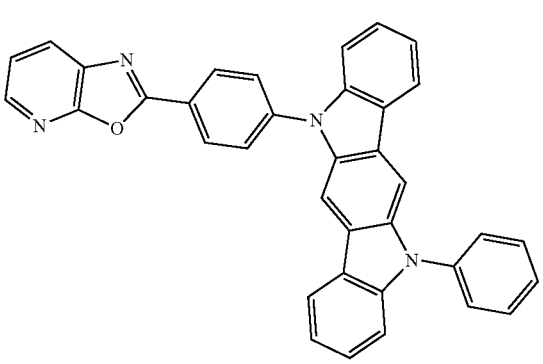
1-27
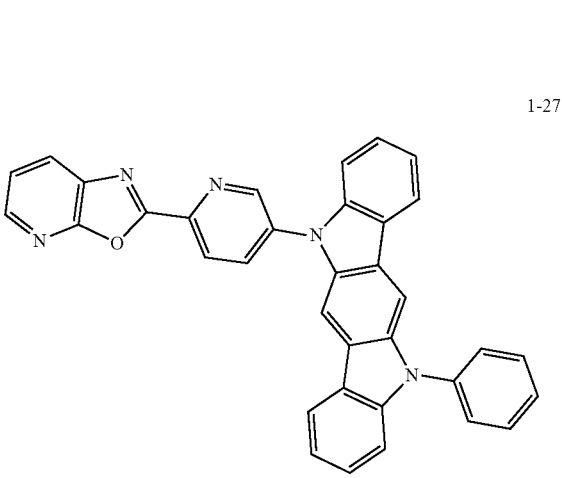

-continued
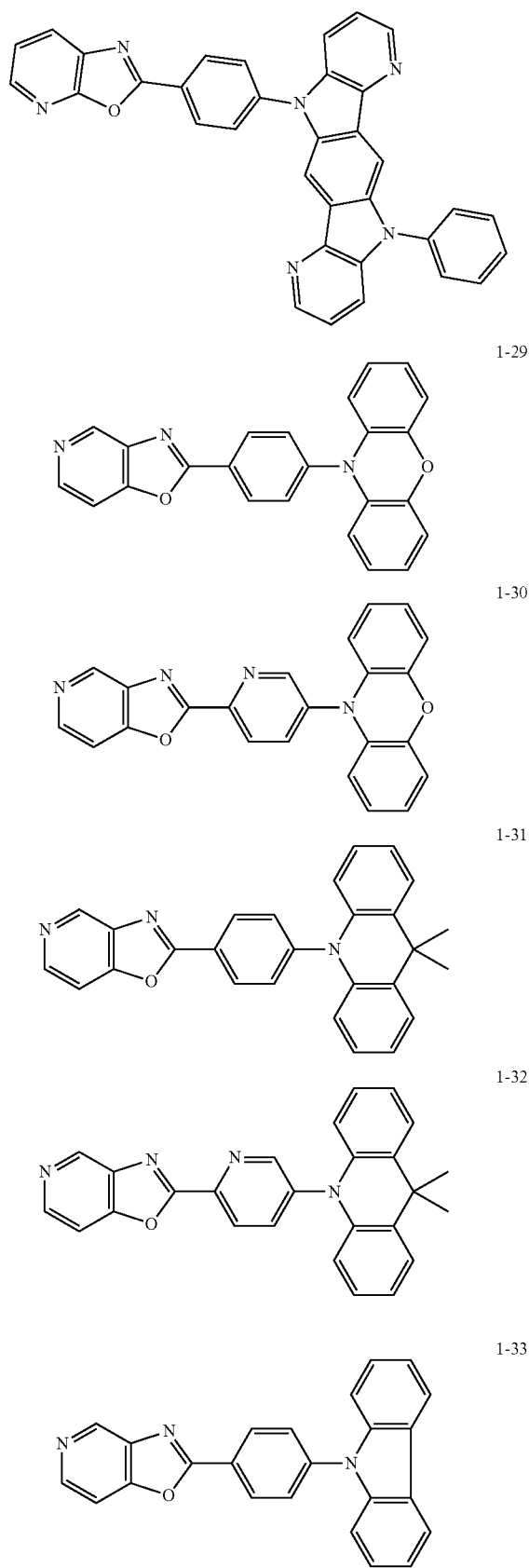
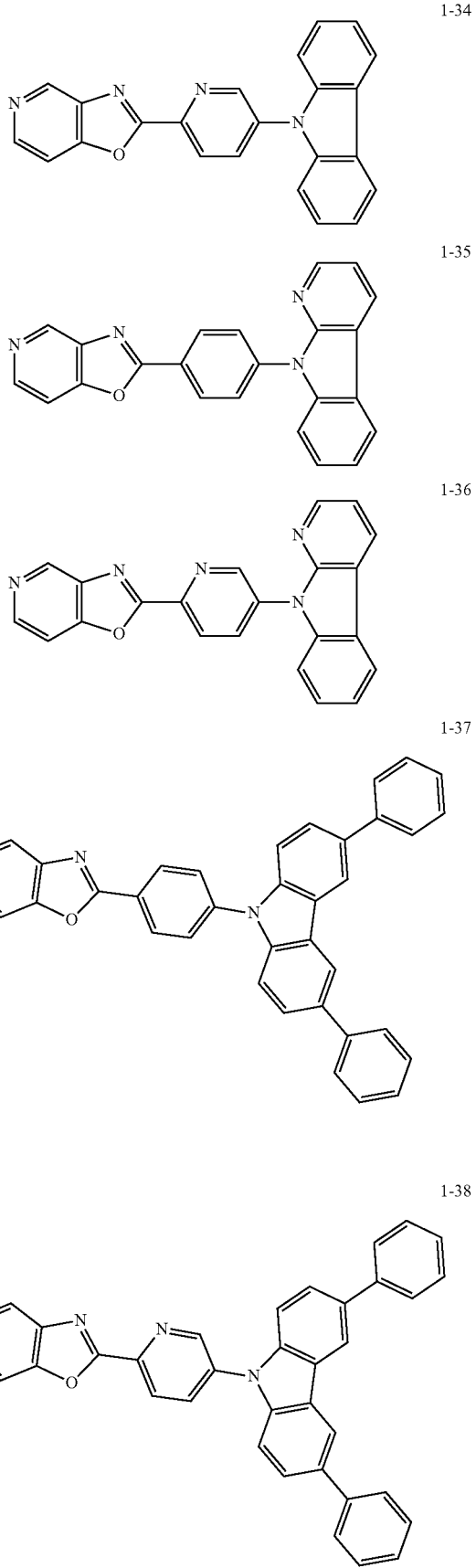

1-39
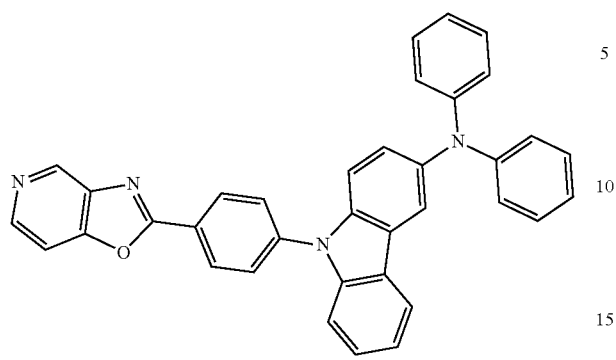
1-40
1-41
1-42
1-43
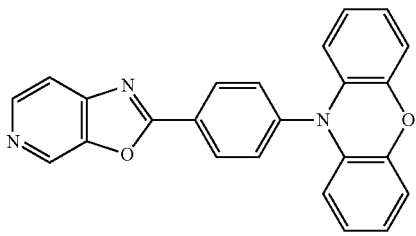
1-44
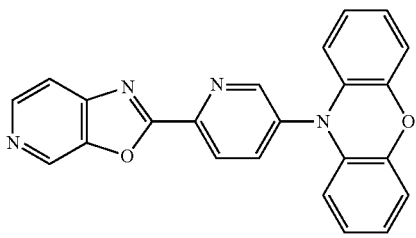
1-45
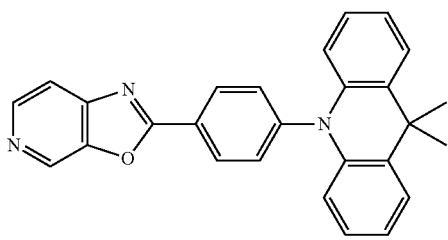
1-46
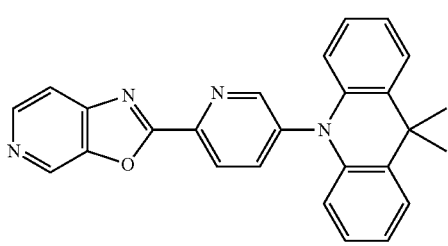
1-47
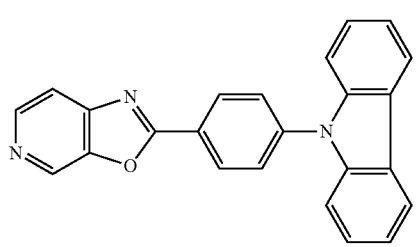
1-48
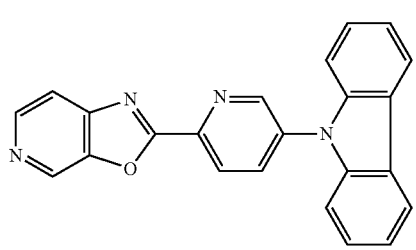

1-49
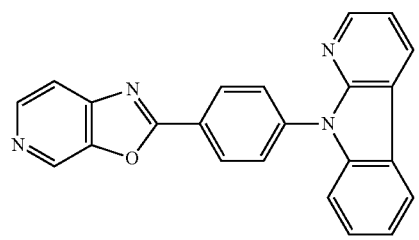
1-50
1-51
1-52
1-53
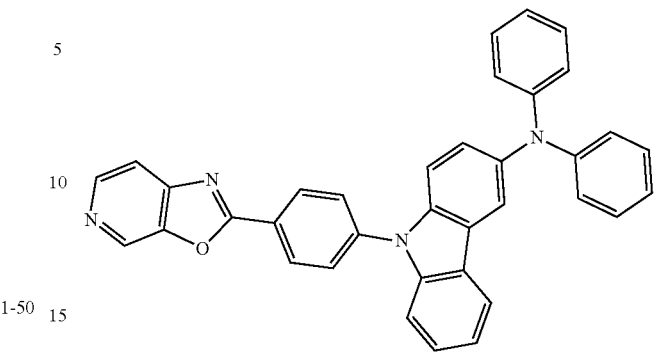
1-54
1-55
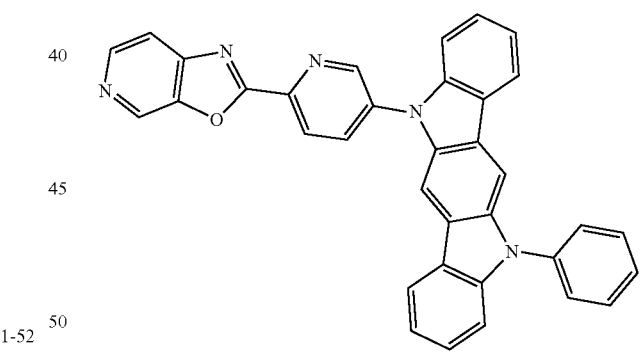
1-56
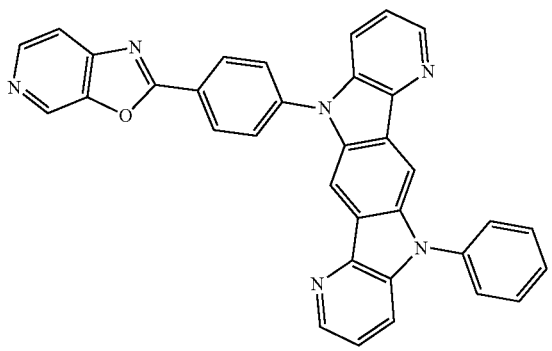

1-57 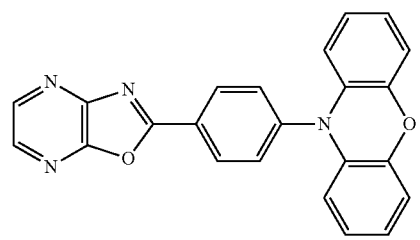
1-58 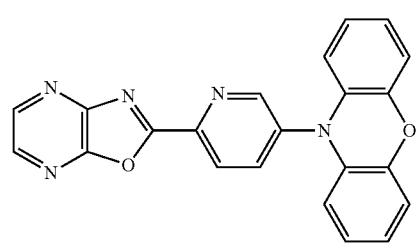
1-59 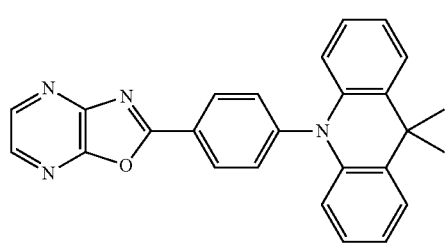
1-60 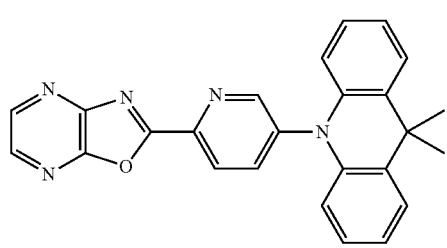
1-61 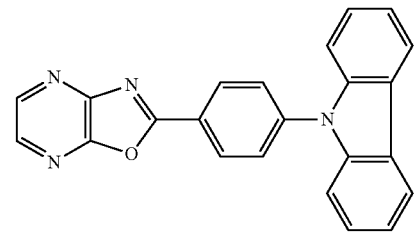
1-62 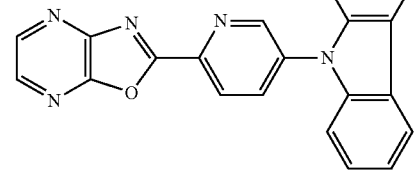
1-63 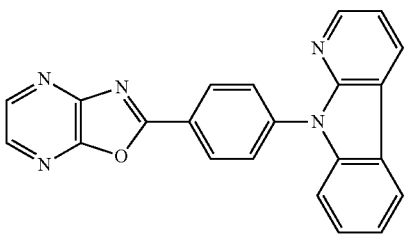
1-64 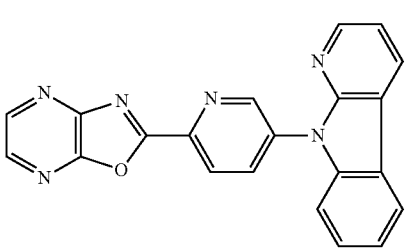
1-65 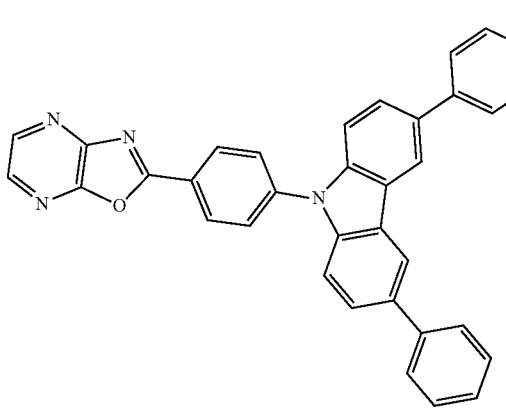
1-66 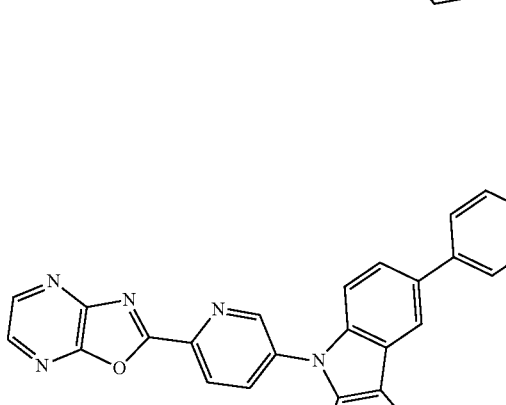

-continued
1-67
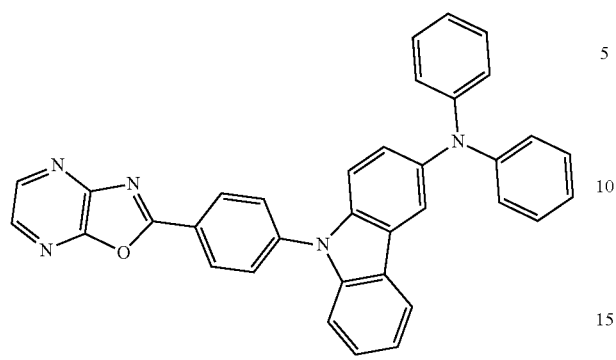
1-68
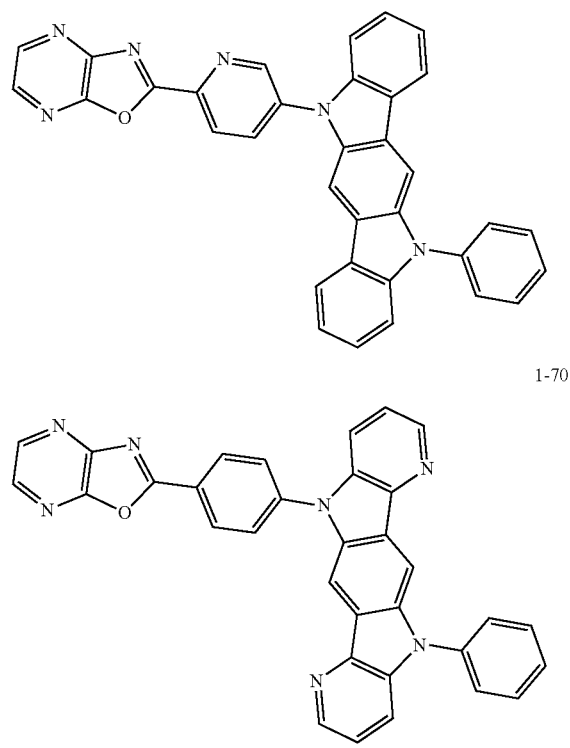
1-69
1-70
-continued
1-71
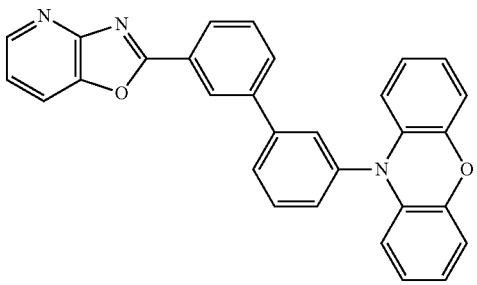
1-72
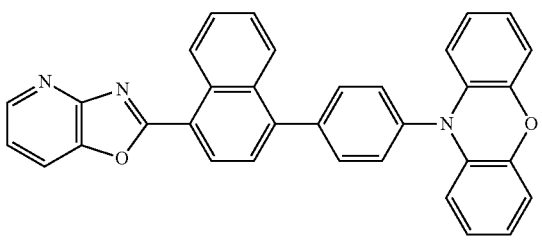
1-73
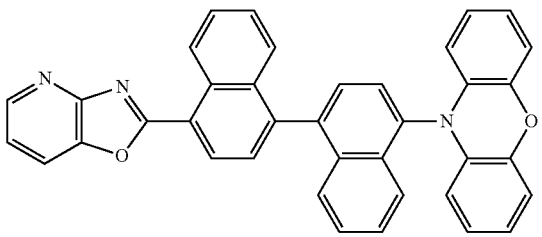
1-74
1-75
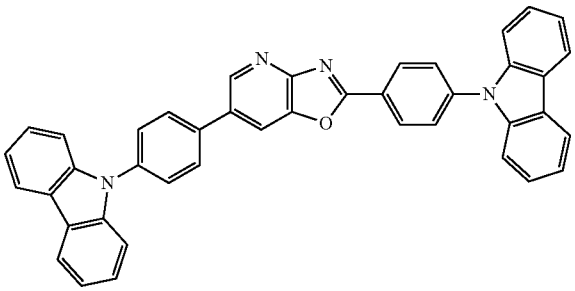

-continued
1-76
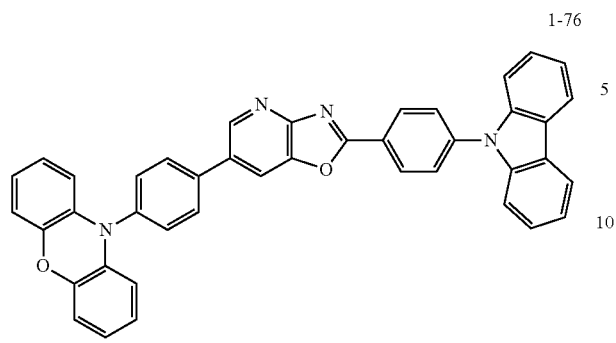
1-77
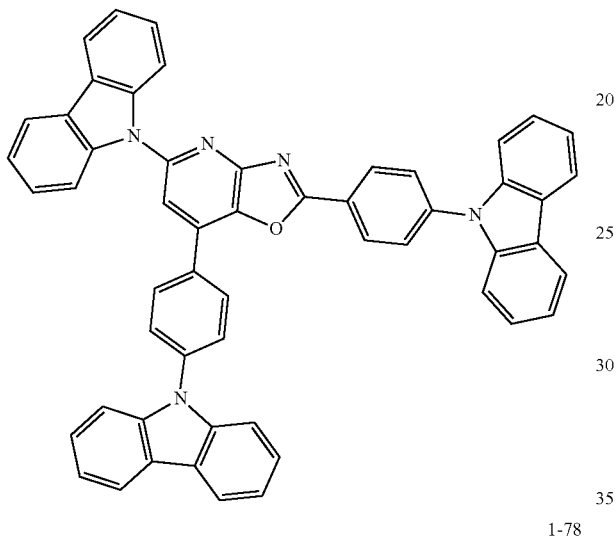
1-78
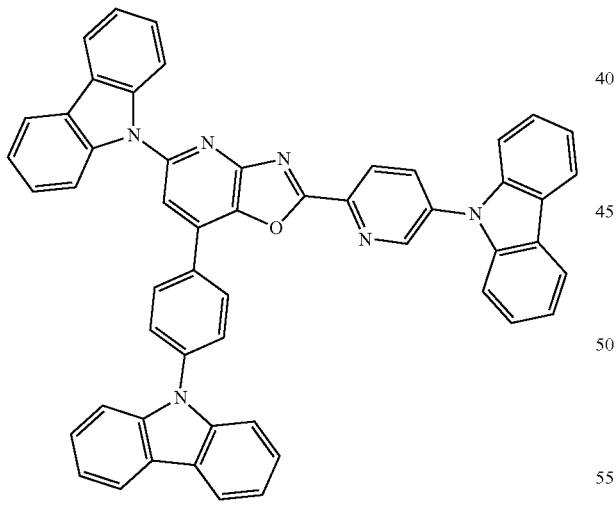
1-79
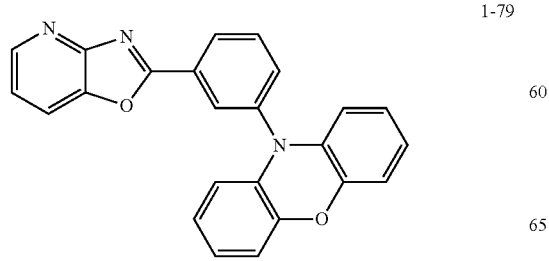
-continued
1-80
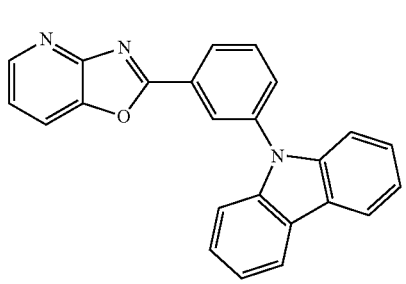
Compound Group 2
2-1
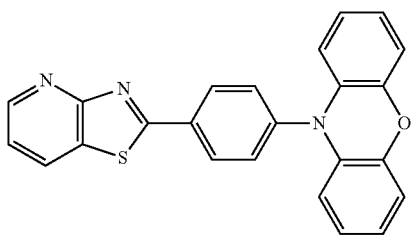
2-2
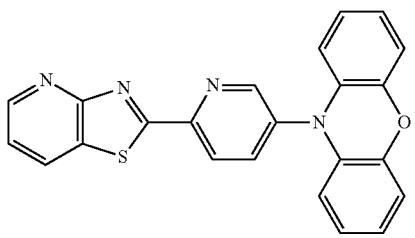
2-3
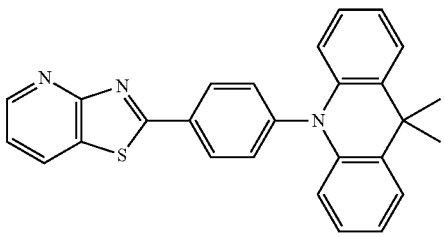
2-4
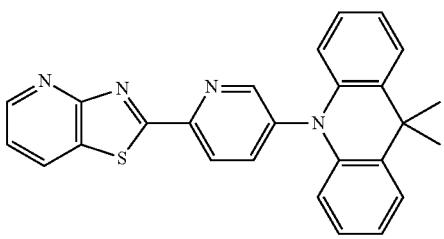
2-5
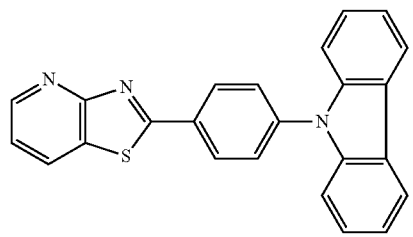

2-6
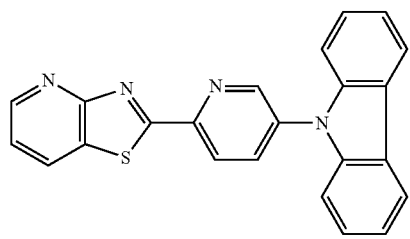
2-7
2-8
2-9
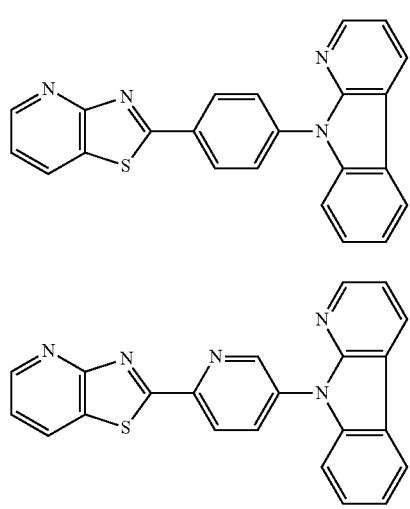
2-10
2-11
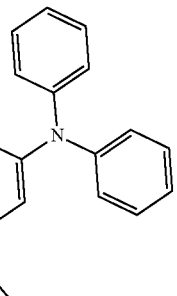
2-12
2-13
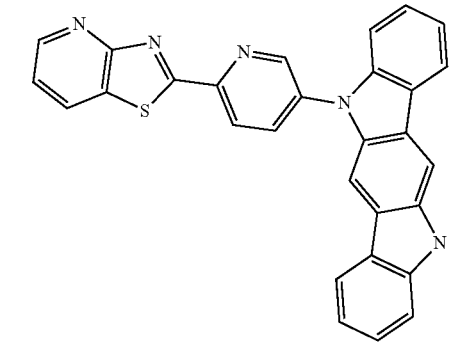
2-14
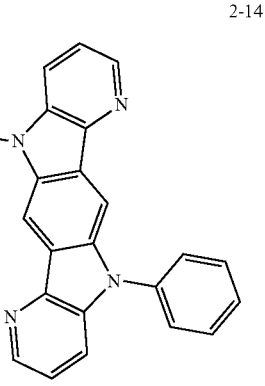

-continued
2-15
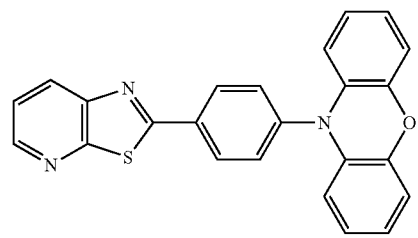
2-16
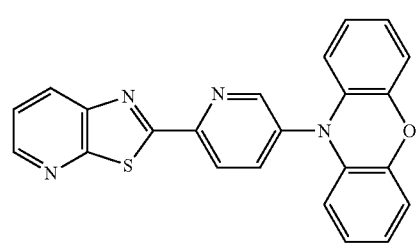
2-17
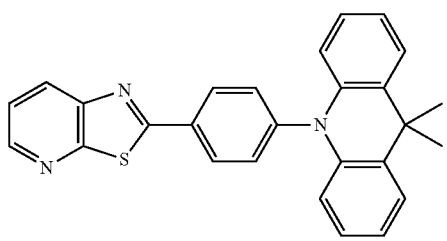
2-18
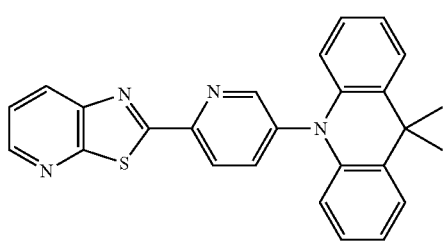
2-19
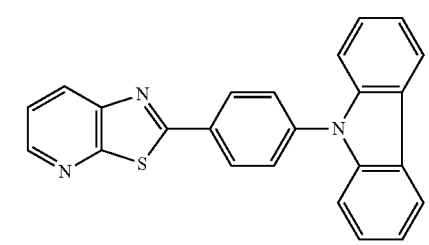
2-20
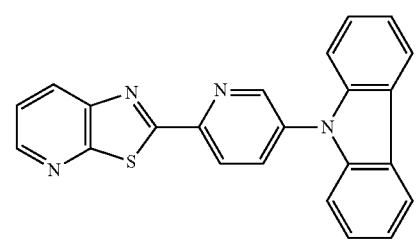
-continued
2-21
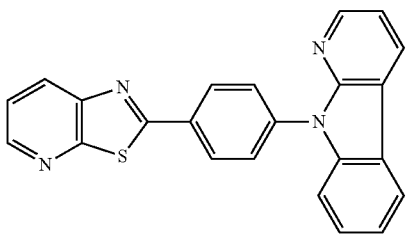
2-22
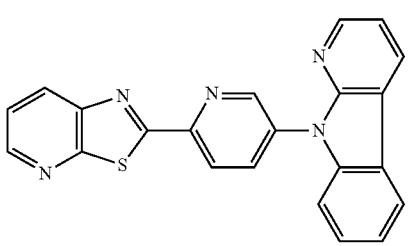
2-23
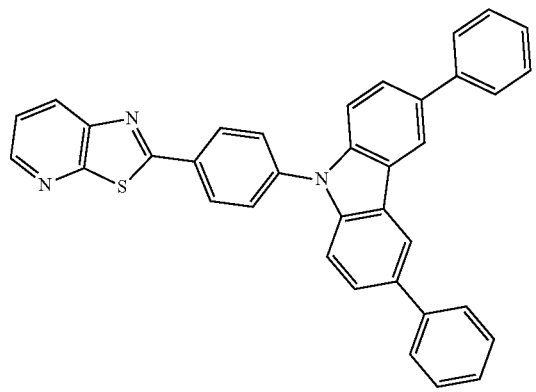
2-24
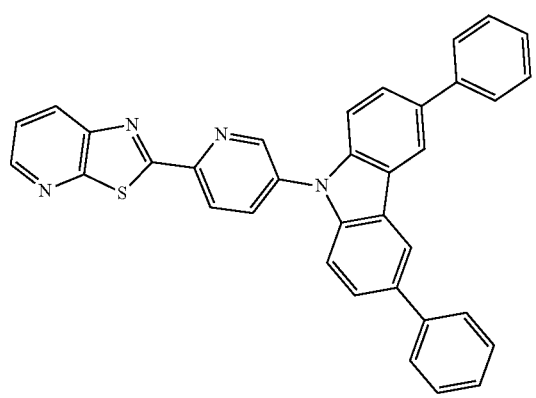

2-25
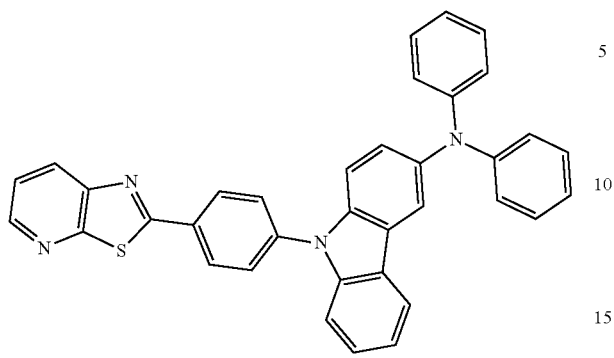
2-26
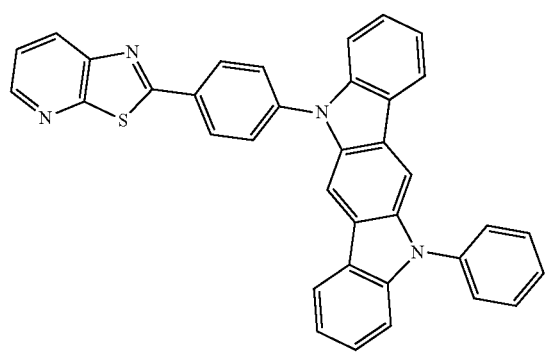
2-27
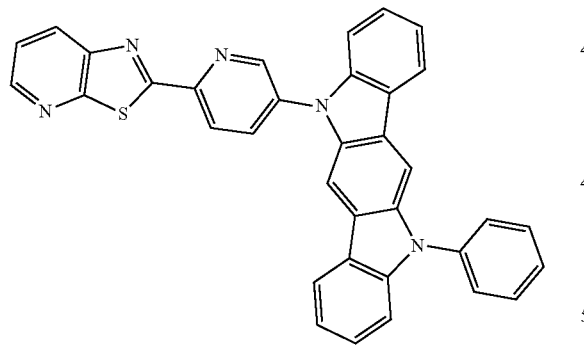
2-28
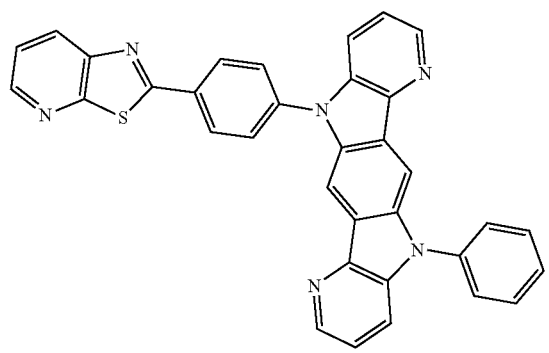
2-29
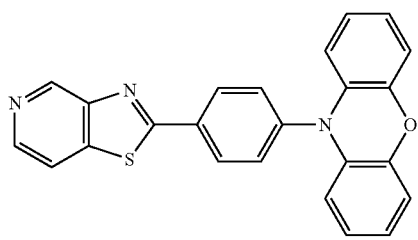
2-30
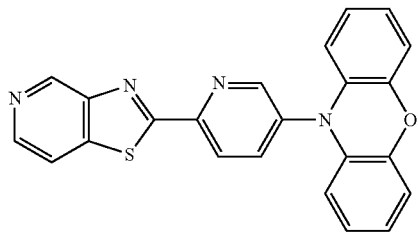
2-31
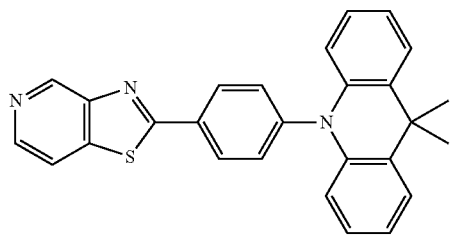
2-32
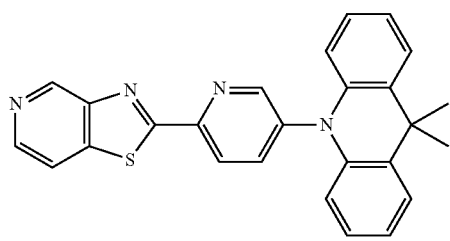
2-33
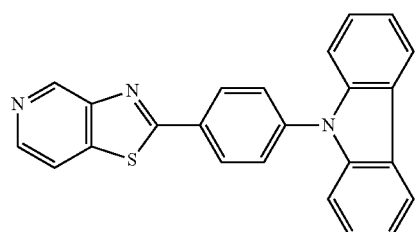
2-34
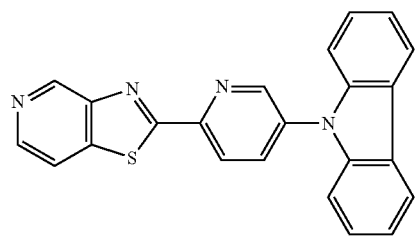

2-35
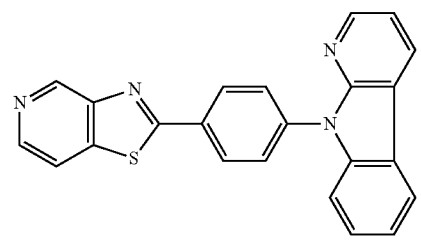
2-36
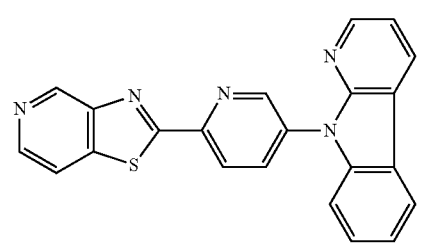
2-37
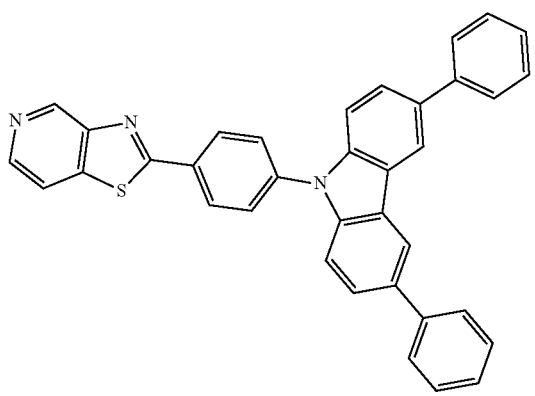
2-38
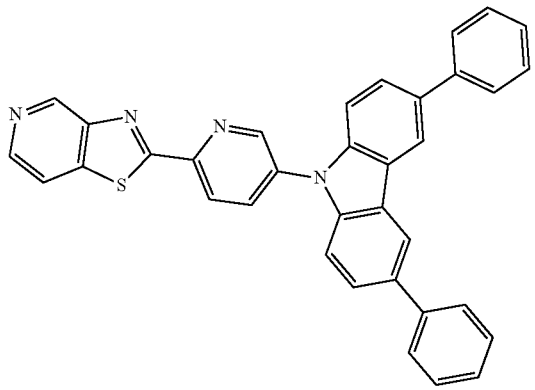
2-39
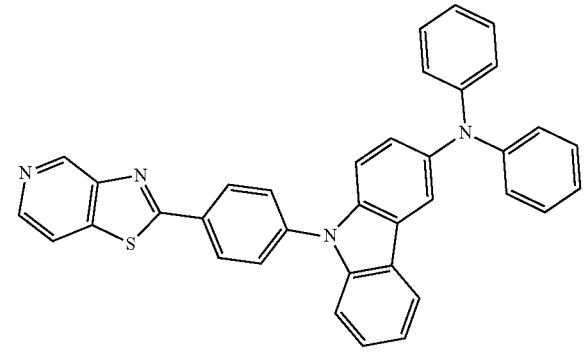
2-40
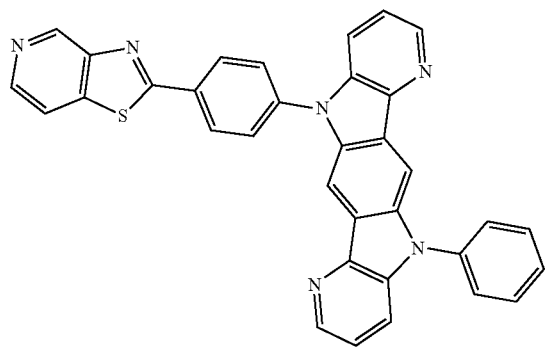
2-41
2-42

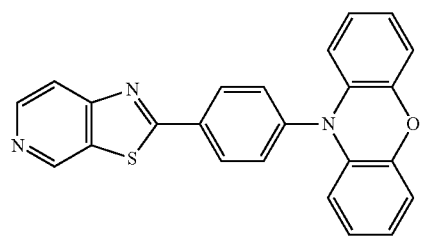
2-43
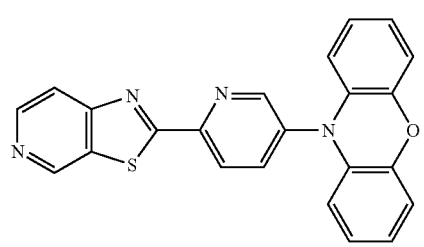
2-44
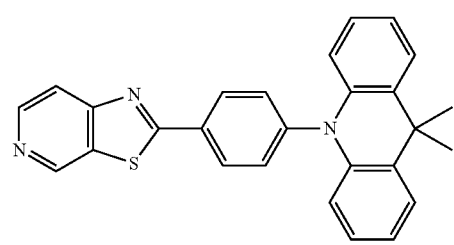
2-45
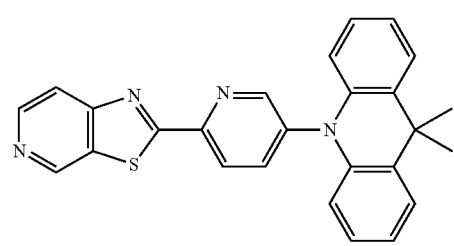
2-46
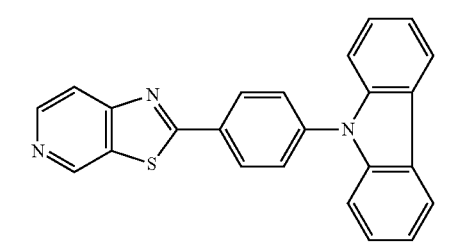
2-47
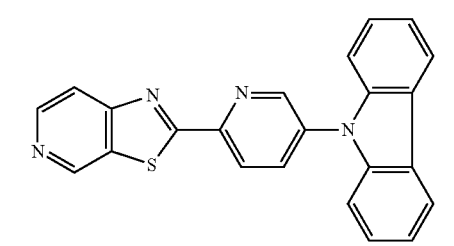
2-48
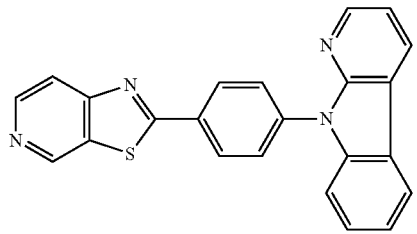
2-49
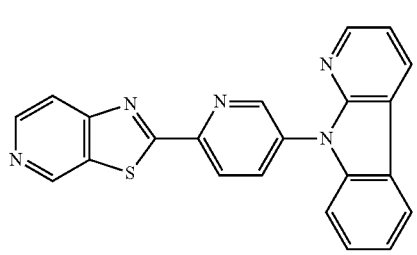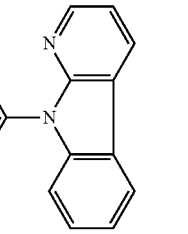
2-50
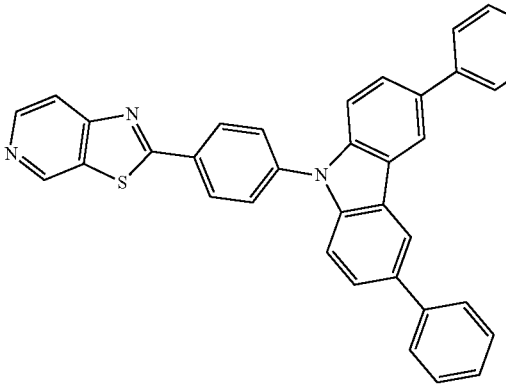
2-51
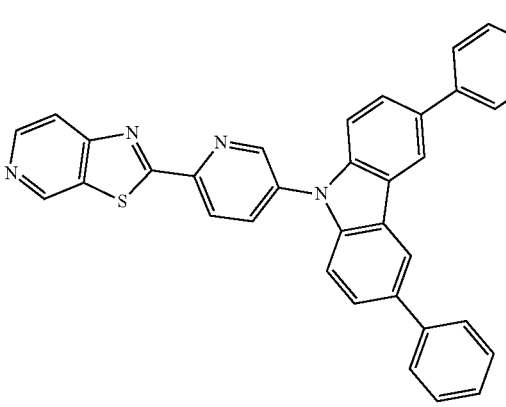
2-52

2-53
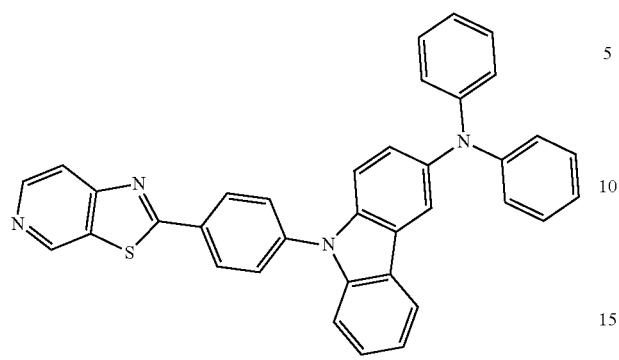
2-54
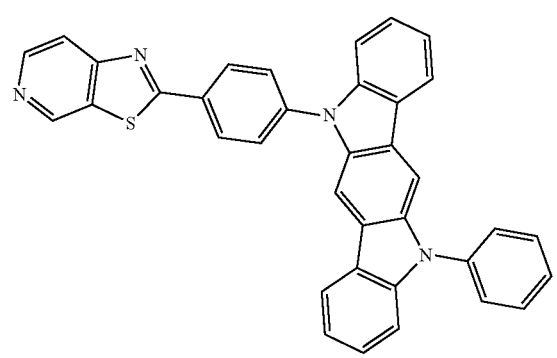
2-55
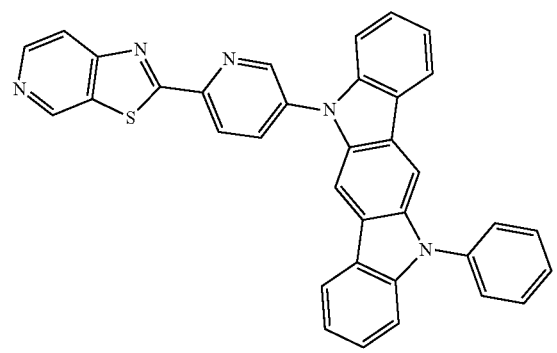
2-56
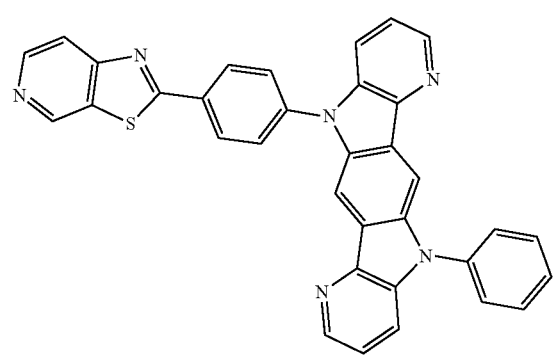
2-57
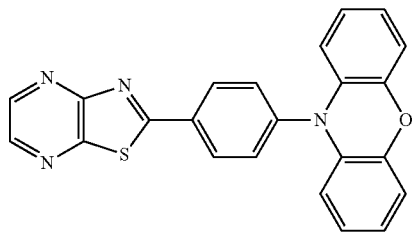
2-58
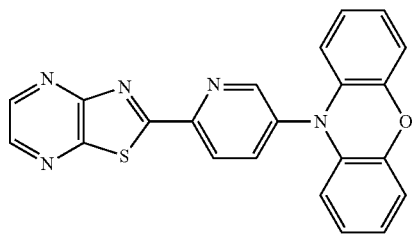
2-59
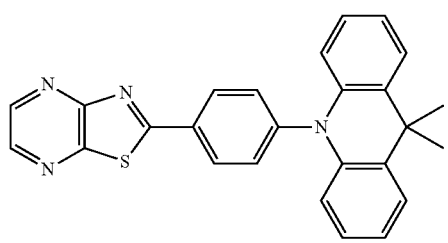
2-60
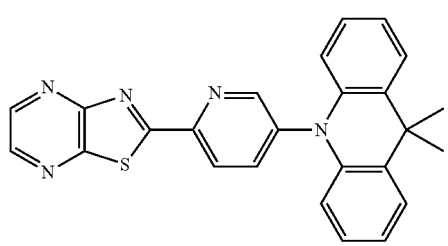
2-61
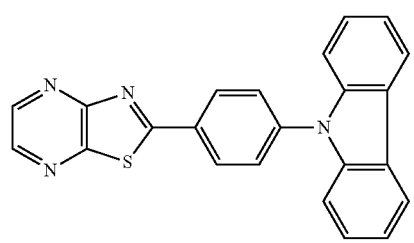
2-62
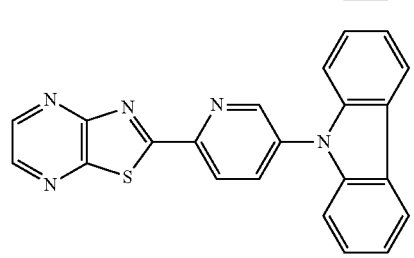

-continued
2-63
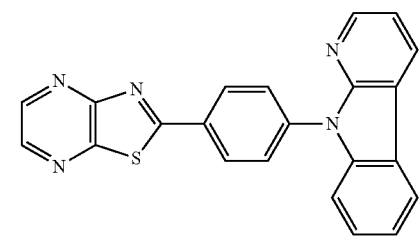
2-64
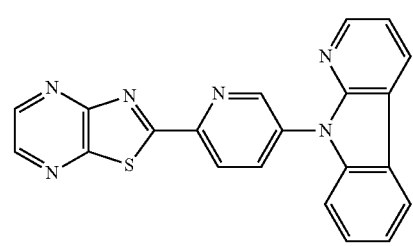
2-65
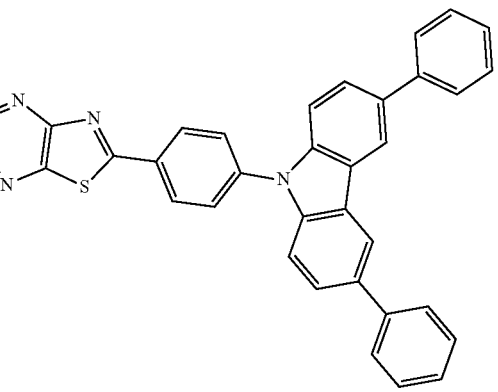
2-66
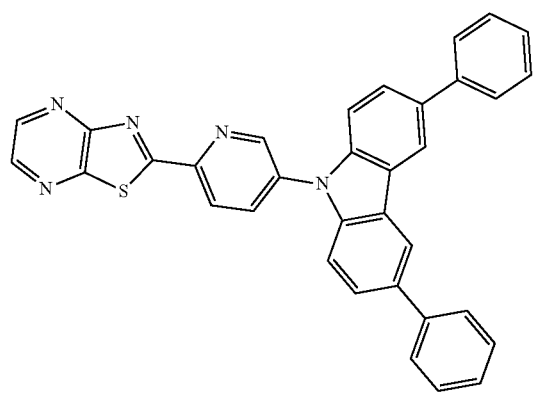
-continued
2-67
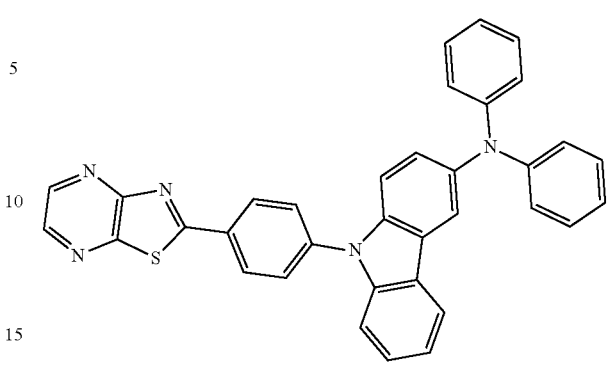
2-68
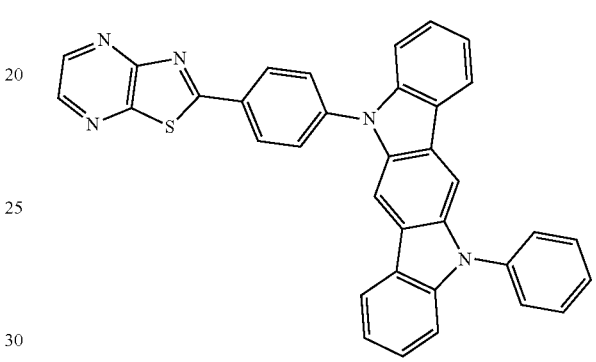
2-69
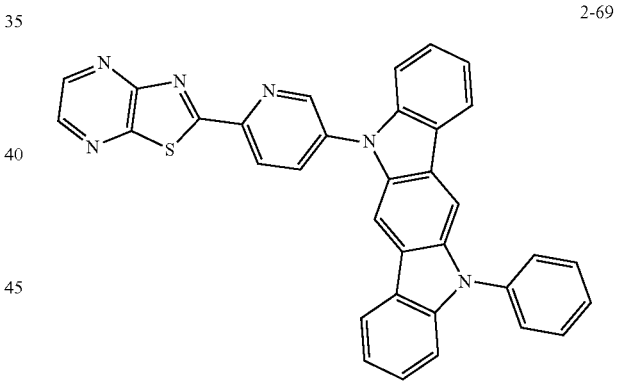
2-70
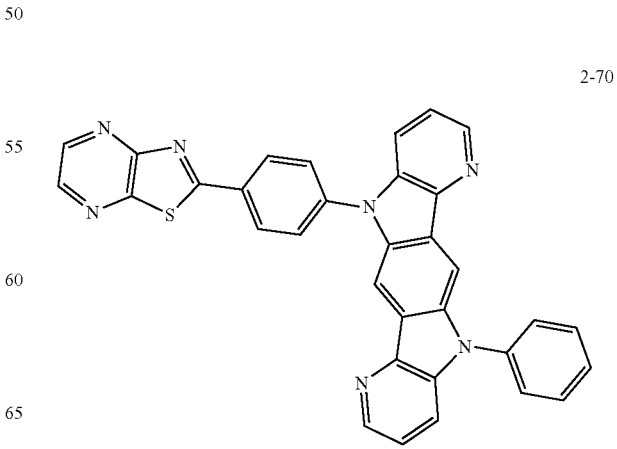

-continued
2-71
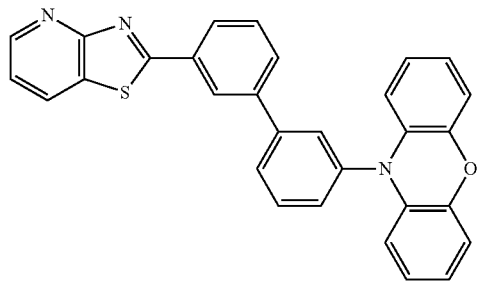
2-72
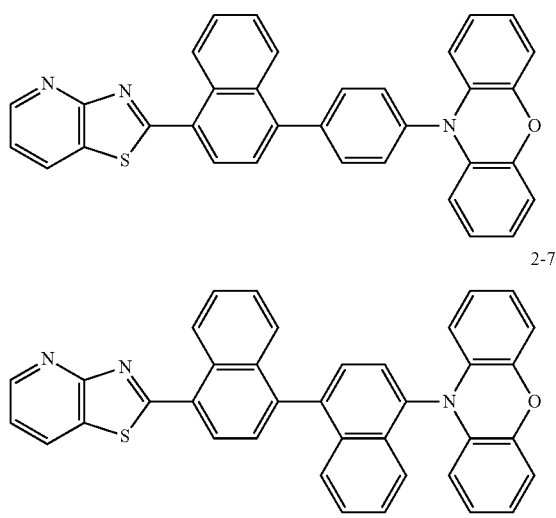
2-73
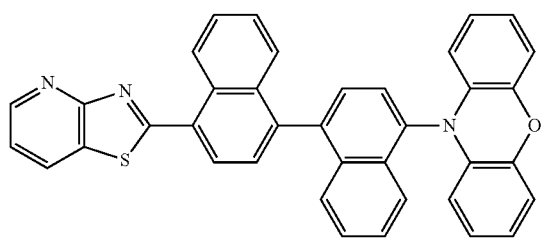
2-74
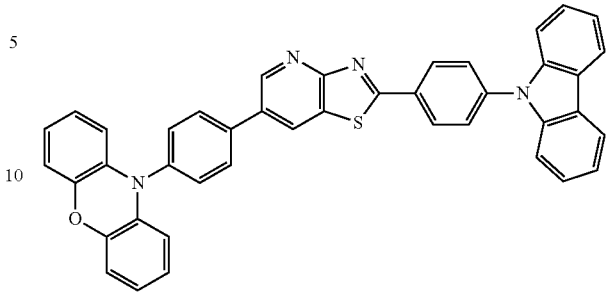
2-75
2-76
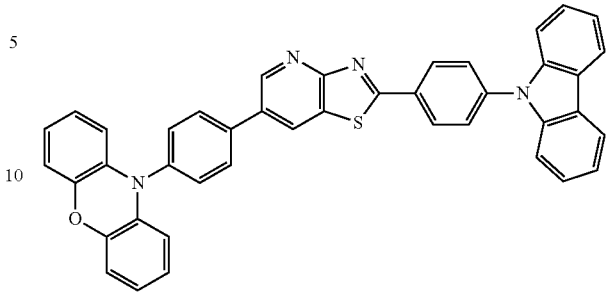
2-77
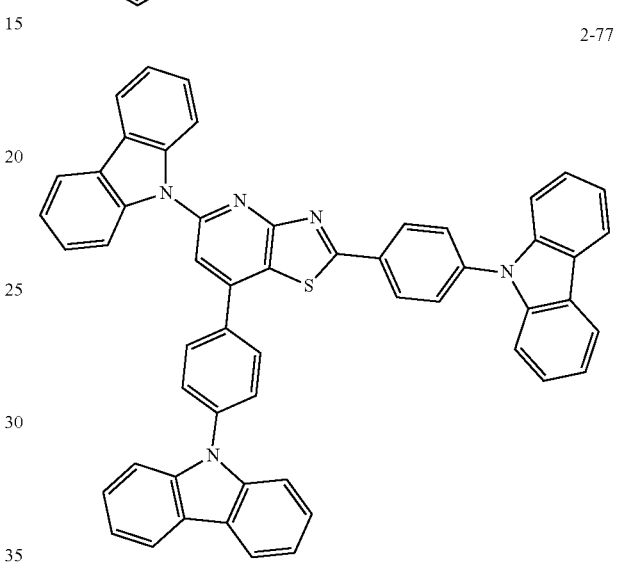
2-78
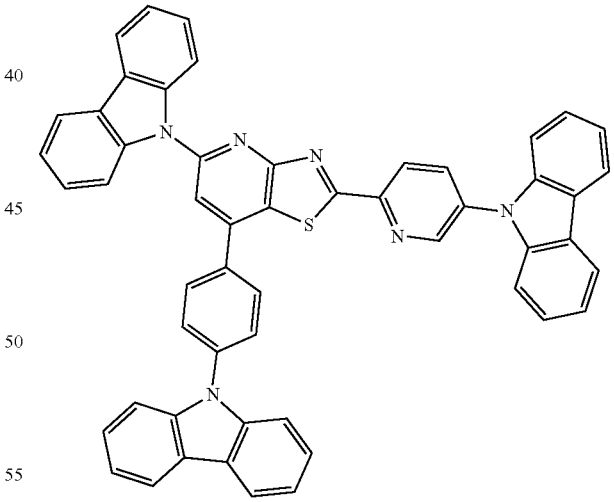
2-79
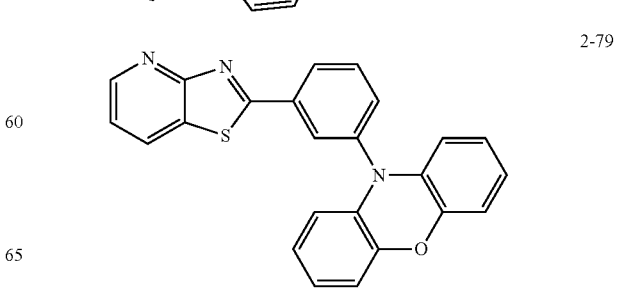

2-80

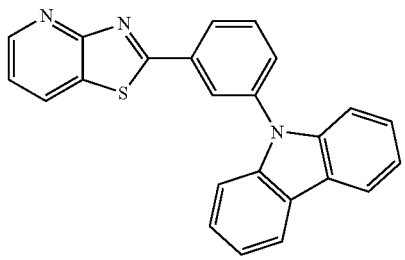

The compound according to an embodiment may be a luminescence material having a luminescence center wavelength ($\lambda_{max}$; e.g., a central wavelength) in a wavelength region of 450 nm or more. For example, the compound represented by Formula 1 of an embodiment may be a luminescence material having a luminescence center wavelength (e.g., a central wavelength) in the 500 nm to 550 nm wavelength region, or a luminescence material having a luminescence center wavelength (e.g., a central wavelength) in the 450 nm to 500 nm (exclusive of 500 nm) wavelength region. The compound represented by Formula 1 of an embodiment may be a green dopant or a blue dopant.

The emission layer EML in the organic electroluminescence device 10 of an embodiment may include a host and a dopant, and may include the above-described compound of an embodiment as a dopant. For example, the emission layer EML in the organic electroluminescence device 10 of an embodiment may include host for emitting a delayed fluorescence and a dopant for emitting a delayed fluorescence, and may include the above-described compound of an embodiment as a dopant for emitting a delayed fluorescence. In some embodiments, the emission layer EML may include at least one selected from among the compounds described above as a thermally activated delayed fluorescence (TADF) dopant.

The compound represented by Formula 1 of an embodiment may be a D (donor)-A (acceptor) type delayed fluorescence dopant material. In the compound represented by Formula 1 of an embodiment, an Aza-type benzoxazole (e.g., an aza-benzoxazole) or Aza-type benzothiazole (e.g., an aza-benzothiazole) moiety may correspond to an electron-accepting part, and a heterocyclic part represented by "Ar" may correspond to an electron-donating part. For example, the compound represented by Formula 1 of an embodiment may be a D-A type thermally activated delayed fluorescence dopant.

In the compound represented by Formula 1 of an embodiment, the compound having the absolute value of a difference between a lowest singlet excitation energy level (S1) and a lowest triplet excitation energy level (T1) of 0.2 eV or less may be used as a thermally activated delayed fluorescence dopant.

In other words, the emission layer EML of the organic electroluminescence device 10 of an embodiment including the compound according to an embodiment as a material of the emission layer EML may emit a delayed fluorescence. For example, the emission layer EML may emit a thermally activated delayed fluorescence.

The compound of an embodiment may have a novel compound structure including the Aza-type benzoxazole (e.g., an aza-benzoxazole) or Aza-type benzothiazole (e.g., an aza-benzothiazole) moiety as an electron-accepting part, and may be used as a thermally activated delayed fluorescence emitting material and as an emission layer material of the organic electroluminescence device to improve luminous efficiency of the organic electroluminescence device and increase service life. In some embodiments, the compound according to an embodiment may be used as a luminescence material to emit light in the green or blue wavelength region and exhibit excellent luminous efficiency.

In an embodiment, the emission layer EML is a delayed fluorescence emission layer, and the emission layer EML may include any suitable host material available in the art and the above-described compound. For example, in an embodiment, the emission layer EML may include the compound of an embodiment as a host material and may include, as the host material, tris(8-hydroxyquinolinato) aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4''-Tris(carbazol-9-yl)-triphenylamine (TCTA), 1,3,5-tris(1-phenyl-1H-benzo[d]imidazole-2-yl)benzene (TPBi), 2-tert-butyl-9,10-di(naphth-2-yl) anthracene (TBADN), distyrylarylene (DSA), 4,4'-bis(9-carbazolyl)-2,2'-dimethyl-biphenyl (CDBP), 2-Methyl-9, 10-bis(naphthalen-2-yl)anthracene (MADN), bis[2-(diphenylphosphino)phenyl]etheroxide (DPEPO), Hexaphenyl cyclotriphosphazene (CP1), 1,4-bis(triphenylsilyl)benzene (UGH2), Hexaphenylcyclotrisiloxane (DP-$SiO_3$), Octaphenylcyclotetra siloxane ($DPSiO_4$), 2,8-Bis(diphenylphosphoryl)dibenzo[b,d]furan (PPF), 3,3'-bis(N-carbazolyl)-1,1'-biphenyl (mCBP), 1,3-Bis(N-carbazolyl) benzene (mCP), etc. However, embodiments are not limited thereto, and any suitable delayed fluorescence emission host materials available in the art as well as the listed host materials may be included.

However, embodiments are not limited thereto, but the compound of an embodiment may be used as a host material in the emission layer EML. When the compound of an embodiment is used as a host material, any suitable dopant material available in the art as well as the compound of an embodiment may be also used in the emission layer EML.

In an embodiment, the emission layer EML may include, as a dopant material, styryl derivatives (e.g., 1,4-bis[2-(3-N-ethylcarbazolyl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenz enamine (N-BDAVBi)), perylene and the derivatives thereof (e.g., 2,5,8,11-tetra-t-butylperylene (TBP)), pyrene and the derivatives thereof (e.g., 1,1'-dipyrene, 1,4-dipyrenylbenzene, 1,4-bis(N,N-diphenylamino)pyrene), etc.

When the emission layer EML emits green light, the emission layer EML may further include, for example, a fluorescence material including Alq3 (tris(8-hydroxyquinolinato)aluminum). When the emission layer EML emits green light, for example, the emission layer EML may include the compound of an embodiment as a host material, and include, as a dopant material, a metal complex such as $Ir(ppy)_3$(fac-tris(2-phenylpyridine)iridium, and/or an organometallic complex, coumarin, and/or derivatives thereof.

When the emission layer EML emits blue light, for example, the emission layer EML may further include a fluorescence material including any one selected from the group consisting of spiro-DPVBi, spiro-6P, distyryl-benzene (DSB), distyryl-arylene (DSA), polyfluorene (PFO)-based polymer and poly(p-phenylene vinylene) (PPV)-based polymer. When the emission layer EML emits green light, for example, the emission layer EML may include the compound of an embodiment as a host material, and include, as a dopant material, a metal complex such as (4,6-F$_2$ppy)$_2$Irpic, and/or an organometallic complex, perylene, and/or derivative thereof.

In some embodiments, the organic electroluminescence device 10 of an embodiment may include a plurality of emission layers. The plurality of emission layers may be sequentially laminated and provided, for example, the organic electroluminescence device 10 including the plurality of emission layers may emit white light. The organic electroluminescence device including the plurality of emission layers may be an organic electroluminescence device having a tandem structure. When the organic electroluminescence device 10 includes a plurality of emission layers, at least one emission layer EML may include the compound according to an embodiment as described above.

In the organic electroluminescence device 10 of an embodiment shown in FIG. 1 to 4, the electron transport region ETR is provided on the emission layer EML. The electron transport region ETR may include, but is not limited to, at least one of the hole blocking layer HBL, the electron transport layer ETL, or the electron injection layer EIL.

The electron transport region ETR may have a multilayer structure having a single layer formed of a single material, a single layer formed of materials different from each other, or a plurality of layers formed of materials different from each other.

For example, the electron transport region HTR may have a single layer structure of an electron injection layer EIL or an electron transport layer ETL, or a single layer structure formed of electron injection materials or electron transport materials. In addition, the electron transport region ETR may have a single layer structure formed of materials different from each other, or a structure of electron transport layer ETL/electron injection layer EIL, hole blocking layer HBL/electron transport layer ETL/electron injection layer EIL which are sequentially laminated from the emission layer EML, but embodiments are not limited thereto. The electron transport region ETR may have a thickness, for example, of about 300 Å to about 1,500 Å.

The electron transport region ETR may be formed by using various suitable methods such as a vacuum deposition method, a spin coating method, a casting method, a Langmuir-Blodgett (LB) method, an inkjet printing method, a laser printing method, and/or a laser induced thermal imaging (LITI) method.

If the electron transport region ETR includes the electron transport layer ETL, the electron transport region ETR may include an anthracene-based compound. However, embodiments are not limited thereto, and the electron transport region may include, for example, tris(8-hydroxyquinolinato) aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-yl)phenyl)-9,10-dinaphthylanthracene, 1,3,5-Tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate) (Bebq$_2$), 9,10-di (naphthalen-2-yl)anthracene (ADN), 1,3-Bis[3,5-di(pyridin-3-yl)phenyl]benzene (BmPyPhB), or a mixture thereof. The thickness of the electron transport layers ETL may be of about 100 Å to about 1,000 Å, for example, of about 150 Å to about 500 Å. If the thickness of the electron transport layers ETL satisfies the above-described range, suitable or satisfactory electron transport characteristics may be achieved without substantially increasing in driving voltage.

When the electron transport region ETR includes the electron injection layer EIL, the electron transport region ETR may be formed using metal halides such as LiF, NaCl, CsF, RbCl, and RbI, lanthanum metals such as Yb, metal oxides such as Li$_2$O and BaO, Lithium quinolate (Liq), etc., but embodiments are not limited thereto. The electron injection layer EIL may be also formed of a mixture of an electron transport material and an organo metal salt. The organo metal salt may be a material having an energy band gap of about 4 eV or more. For example, the organo metal salt may include metal acetate, metal benzoate, metal acetoacetate, metal acetylacetonate and/or metal stearate. The thickness of the electron injection layers EIL may have a thickness of about 1 Å to about 100 Å, and of about 3 Å to about 90 Å. If the thickness of the electron injection layers EIL satisfies the above-described range, suitable or satisfactory electron injection characteristics may be achieved without substantially increasing in driving voltage.

As described above, the electron transport region ETR may include the hole blocking layer HBL. The hole blocking layer HBL may include, for example, at least one of 2,9-dimethyl-4,7-diphenyl-1,10-phenanthroline (BCP), or 4,7-diphenyl-1,10-phenanthroline (Bphen), but is not limited thereto.

The second electrode EL2 may be on the electron transport region ETR. The second electrode EL2 may be a common electrode or cathode. The second electrode EL2 may be a transmissive electrode, a transflective electrode, or a reflective electrode. When the second electrode EL2 is the transmissive electrode, the second electrode EL2 may be formed of transparent metal oxides, for example, indium tin oxide (ITO), indium zinc oxide (IZO), zinc oxide (ZnO), indium tin zinc oxide (ITZO), etc.

When the second electrode EL2 is the transflective electrode or the reflective electrode, the second electrode EL2 may include Ag, Mg Cu, Al, Pt, Pd, Au, Ni, Nd, Ir, Cr, Li, Ca, LiF/Ca, LiF/Al, Mo, Ti, or a compound or mixture (e.g., a mixture of Ag and Mg) including the same. In some embodiments, the second electrode EL2 may have a multi-layered structure including a reflective layer or transflective layer and a transparent conductive layer formed of indium tin oxide (ITO), indium zinc oxide (IZO), zinc oxide (ZnO), and/or indium tin zinc oxide (ITZO).

In some embodiments, the second electrode EL2 may be coupled to an auxiliary electrode. When the second electrode EL2 is coupled to the auxiliary electrode, resistance of the second electrode EL2 may be decreased.

In some embodiments, a capping layer CPL may be further on the second electrode EL2 of the organic electroluminescence device 10 of an embodiment. The capping layer CPL may include, for example, α-NPD, NPB, TPD, m-MTDATA, Alq$_3$, CuPc, N4,N4,N4',N4'-tetra (biphenyl-4-yl) biphenyl-4,4'-diamine (TPD15), 4,4',4''-Tris (carbazol-9-yl) triphenylamine (TCTA), etc.

The organic electroluminescence device 10 according to an embodiment of the present disclosure may include the above-described compound of an embodiment in the emission layer EML between the first electrode EL1 and the second electrode EL2 to exhibit improved luminous efficiency. The compound according to an embodiment may be a thermally activated delayed fluorescence dopant, and the emission layer EML may include the compound of an embodiment to emit a thermally activated delayed fluorescence, and thereby exhibiting good luminous efficiency characteristics. In addition, the compound according to an embodiment may be included as a host material in the emission layer EML, and may be used with any suitable fluorescence dopant material available in the art or any suitable phosphorescence dopant material available in the art to improve luminous efficiency and service life of the organic electroluminescence device. In some embodiments, the compound according to an embodiment may be used as a dopant material of the emission layer EML, and realize the organic electroluminescence device having excellent luminous efficiency and long service life characteristics even in a green emitting region or blue emitting region.

In some embodiments, the above-described compound of an embodiment may be included as a material for the organic electroluminescence device 10 in an organic layer as well as the emission layer EML. For example, the organic electroluminescence device 10 of an embodiment of the present disclosure may also include the above-described compound in at least one functional layer between the first electrode EL1 and the second electrode EL2, or in the capping layer CPL on the second electrode EL2.

The above-described compound of an embodiment may have a novel compound structure including the Aza-type benzoxazole (e.g., an aza-benzoxazole) or Aza-type benzothiazole (e.g., an aza-benzothiazole) moiety as an electron-accepting part, and may be used as an emission layer material to contribute to high efficiency characteristics of the organic electroluminescence device. Furthermore, the organic electroluminescence device of an embodiment including the compound of an embodiment in the emission layer may exhibit high efficiency characteristics in a green wavelength region or a blue wavelength region.

Hereinafter, the compound according to an embodiment of the present disclosure and the organic electroluminescence device of an embodiment will be explained in in more detail with reference to examples and comparative examples. In addition, the examples below are exemplified for assisting the understanding of the present disclosure, and the scope of the present disclosure is not limited thereto.

Examples

1. Synthesis of Compound of One Embodiment

First, a compound synthesis method according to the present embodiment will be described by exemplifying methods for synthesizing compounds 1-1, 1-5, 1-43, 1-47, 1-51, 1-58, 1-79, and 1-80. In addition, in the following descriptions, a compound synthesis method is provided as an example, but an embodiment of the present disclosure is not limited to the following examples.

(1) Synthesis of Compound 1-1

Compound 1-1 according to an embodiment may be synthesized by, for example, the steps shown in Reaction Formula 1 below:

Reaction Formula 1

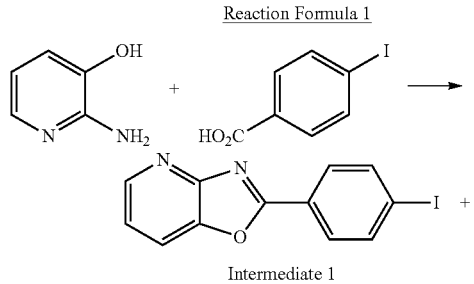

Intermediate 1

-continued

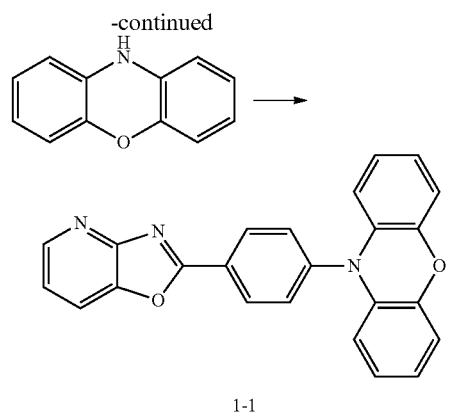

1-1

Synthesis of Intermediate 1

In a 500 mL one-neck flask, 2-aminopyridin-3-ol (20.0 g, 181.6 mmol) and 4-iodobenzoic acid (45.1 g, 181.6 mmol) were mixed well, and POCl$_3$ (140 mL) was added slowly at 0° C. and then stirred. After heating to 90° C., the mixture was reacted for 12 hours. After the reaction was believed to be completed, the reactant was cooled to room temperature, and added dropwise slowly to ice. The reactant was neutralized with a sodium carbonate solution, and the formed solid was then filtered, washed with water and methanol, and dried to obtain a white solid compound (Intermediate 1) (43.0 g, yield: 73.5%).

Synthesis of Compound 1-1

In a 250 mL one-neck flask, Intermediate 1 (3.5 g, 10.9 mmol), phenoxazine (2.1 g, 11.4 mmol), Pd(dba)$_2$ (0.31 g, 0.54 mmol), P(tBu)$_3$ (0.53 mL, 1.1 mmol, 50 wt % toluene solution), NaOtBu (2.1 g, 21.7 mmol), and xylene (54 mL) were refluxed and stirred for one day. The reactant was cooled to room temperature and the impurities were removed by celite filtration. After the solvent was completely removed, the reactant was purified by silica gel column chromatography (EA:CHCl$_3$=1:20). The obtained solid was treated with acetone and filtered to obtain Compound 1-1 which is a yellow solid (797.0 mg, yield: 19.4%).

(2) Synthesis of Compound 1-5

Compound 1-5 according to an embodiment may be synthesized by, for example, the steps shown in Reaction Formula 2 below:

Reaction Formula 2

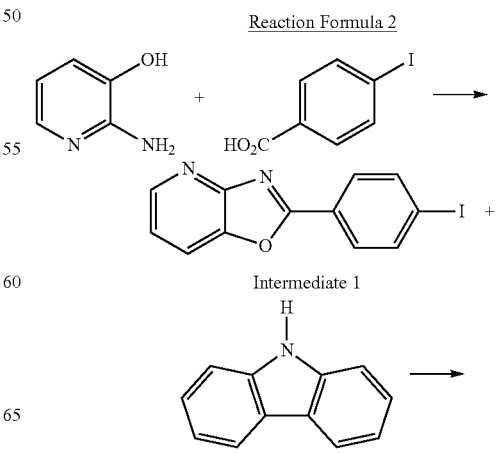

Intermediate 1

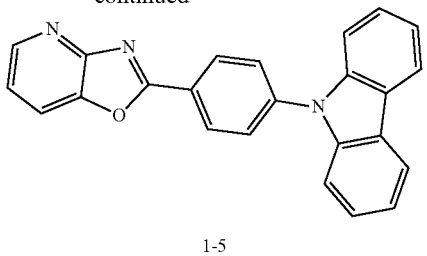

1-5

In a 250 mL one-neck flask, Intermediate 1 (3.5 g, 10.9 mmol), 9H-carbazole (1.5 g, 9.0 mmol), Pd(dba)$_2$ (0.31 g, 0.54 mmol), P(tBu)$_3$ (0.53 mL, 1.1 mmol, 50 wt % toluene solution), NaOtBu (2.1 g, 21.7 mmol), and xylene (54 mL) were refluxed and stirred for one day. The reactant was cooled to room temperature and the impurities were removed by celite filtration. After the solvent was completely removed, the reactant was purified by silica gel column chromatography (EA:CHCl$_3$=1:20). The obtained solid was treated with acetone and filtered to obtain Compound 1-5 which is a yellow solid (1.2 g, yield: 35.1%).

(3) Synthesis of Compound 1-43

Compound 1-43 according to an embodiment may be synthesized by, for example, the steps shown in Reaction Formula 3 below:

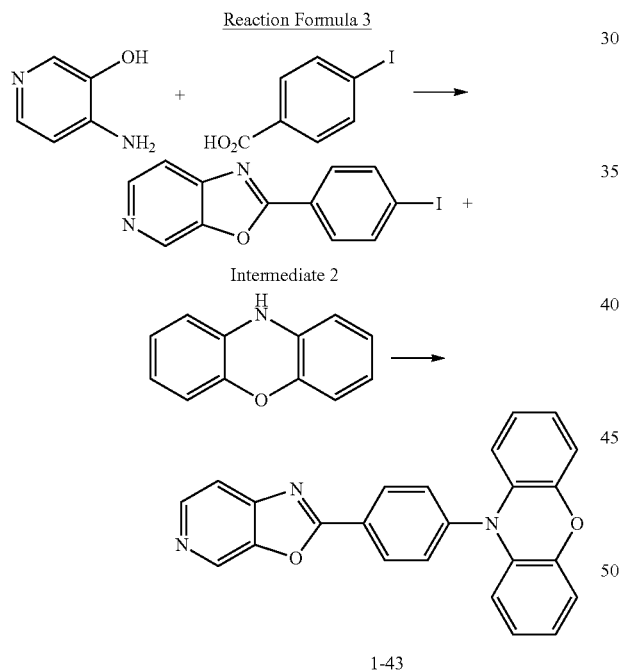

Reaction Formula 3

1-43

Synthesis of Intermediate 2

In a 250 mL one-neck flask, 4-aminopyridin-5-ol (5.0 g, 45.4 mmol) and 4-iodobenzoic acid (11.3 g, 45.4 mmol) were mixed well, and POCl$_3$ (40 mL) was added slowly at 0° C. and then stirred. After heating to 90° C., the mixture was reacted for 12 hours. After the reaction was believed to be completed, the reactant was cooled to room temperature, and added dropwise slowly to ice. The reactant was neutralized with a sodium carbonate solution, and the formed solid was then filtered, washed with water and methanol, and dried to obtain a white solid compound (Intermediate 2) (7.2 g, yield: 49.2%).

Synthesis of Compound 1-43

In a 250 mL one-neck flask, Intermediate 2 (3.5 g, 10.9 mmol), phenoxazine (2.1 g, 11.4 mmol), Pd(dba)$_2$ (0.31 g, 0.54 mmol), P(tBu)$_3$ (0.53 mL, 1.1 mmol, 50 wt % toluene solution), NaOtBu (2.1 g, 21.7 mmol), and xylene (54 mL) were refluxed and stirred for one day. The reactant was cooled to room temperature and the impurities were removed by celite filtration. After the solvent was completely removed, the reactant was purified by silica gel column chromatography (EA:CHCl$_3$=1:20). The obtained solid was treated with acetone and filtered to obtain Compound 1-43 which is a yellow solid (1.0 g, yield: 24.4%).

(4) Synthesis of Compound 1-47

Compound 1-47 according to an embodiment may be synthesized by, for example, the steps shown in Reaction Formula 4 below:

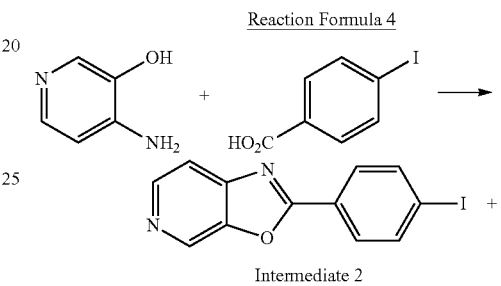

Reaction Formula 4

Intermediate 2

1-47

In a 250 mL one-neck flask, Intermediate 2 (3.5 g, 10.9 mmol), 9H-carbazole (1.5 g, 9.0 mmol), Pd(dba)$_2$ (0.31 g, 0.54 mmol), P(tBu)$_3$ (0.53 mL, 1.1 mmol, 50 wt % toluene solution), NaOtBu (2.1 g, 21.7 mmol), and xylene (54 mL) were refluxed and stirred for one day. The reactant was cooled to room temperature and the impurities were removed by celite filtration. After the solvent was completely removed, the reactant was purified by silica gel column chromatography (EA:CHCl$_3$=1:20). The obtained solid was treated with acetone and filtered to obtain Compound 1-47 which is a yellow solid (925 mg, yield: 28.5%).

(5) Synthesis of Compound 1-51

Compound 1-51 according to an embodiment may be synthesized by, for example, the steps shown in Reaction Formula 5 below:

Reaction Formula 5

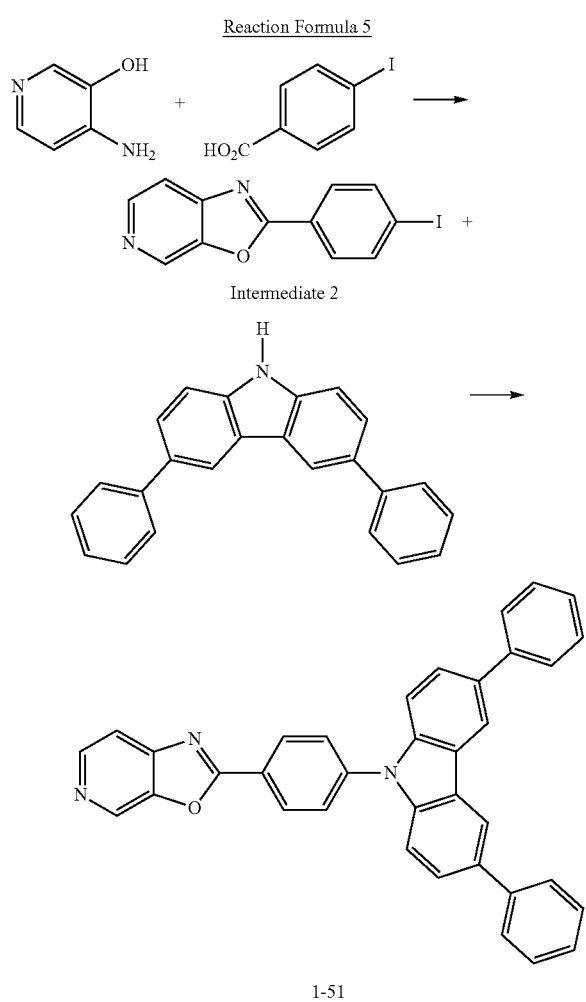

1-51

In a 250 mL one-neck flask, Intermediate 2 (1.5 g, 4.5 mmol), 3,6-diphenyl-9H-carbazole (2.8 g, 9.0 mmol), Pd(dba)$_2$ (0.3 g, 0.5 mmol), P(tBu)$_3$ (0.26 g, 0.5 mmol, 50 wt % toluene solution), NaOtBu (1.5 g, 15.8 mmol), and xylene (45 mL) were refluxed and stirred for one day. The reactant was cooled at room temperature and the impurities were removed by celite filtration. After the solvent was completely removed, the reactant was purified by silica gel column chromatography (MC:HEX=1:8→1:1). Such obtained product was solidified by Acetone:MeOH=2:1, and then filtered to obtain Compound 1-51 which is a red-brown solid (1.7 g, yield: 73.4%).

(6) Synthesis of Compound 1-53

Compound 1-53 according to an embodiment may be synthesized by, for example, the steps shown in Reaction Formula 6 below:

Reaction Formula 6

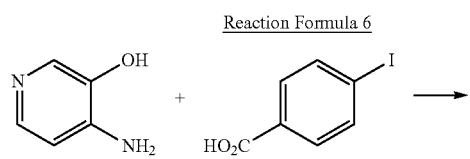

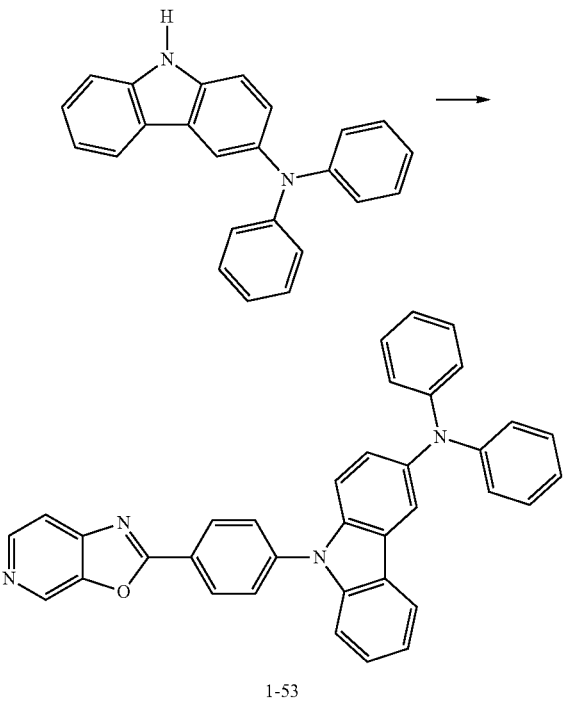

1-53

In a 250 mL one-neck flask, Intermediate 2 (1.5 g, 4.5 mmol), N,N-diphenyl-9H-carbazole-3-amine (3.0 g, 9.0 mmol), Pd(dba)$_2$ (0.3 g, 0.5 mmol), P(tBu)$_3$ (0.26 g, 0.5 mmol, 50 wt % toluene solution), NaOtBu (1.5 g, 15.8 mmol), and xylene (45 mL) were refluxed and stirred for one day. The reactant was cooled at room temperature and the impurities were removed by celite filtration. After the solvent was completely removed, the reactant was purified by silica gel column chromatography (MC:HEX=1:8→1:1). Such obtained product was solidified by Acetone:MeOH=2: 1, and then filtered to obtain Compound 1-53 which is a red-brown solid (1.7 g, yield: 71.2%).

(7) Synthesis of Compound 1-79

Compound 1-79 according to an embodiment may be synthesized by, for example, the steps shown in Reaction Formula 7 below:

Reaction Formula 7

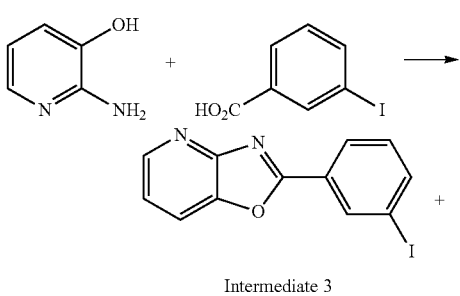

Intermediate 3

-continued

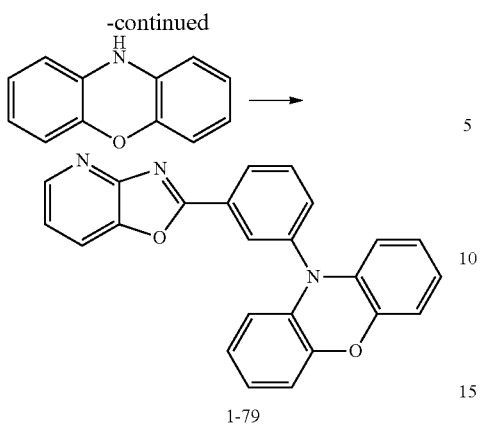

1-79

-continued

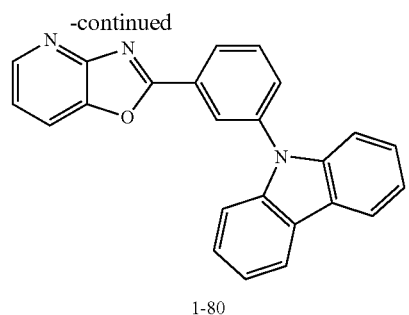

1-80

In a 250 mL one-neck flask, Intermediate 3 (3.5 g, 10.9 mmol), 9H-carbazole (1.5 g, 9.0 mmol), Pd(dba)$_2$ (0.31 g, 0.54 mmol), P(tBu)$_3$ (0.53 mL, 1.1 mmol, 50 wt % toluene solution), NaOtBu (2.1 g, 21.7 mmol), and xylene (54 mL) were refluxed and stirred for one day. The reactant was cooled to room temperature and the impurities were removed by celite filtration. After the solvent was completely removed, the reactant was purified by silica gel column chromatography (EA:CHCl$_3$=1:20). The obtained solid was treated with acetone and filtered to obtain Compound 1-80 which is a yellow solid (1.4 g, yield: 42.6%).

(9) Synthesis of Compound 2-5

Compound 2-5 according to an embodiment may be synthesized by, for example, the steps shown in Reaction Formula 9 below:

Synthesis of Intermediate 3

In a 250 mL one-neck flask, 2-aminopyridin-3ol (10.0 g, 90.8 mmol) and 3-iodobenzoic acid (22.5 g, 90.8 mmol) were mixed well, and POCl$_3$ (70 mL) was added slowly at 0° C. and then stirred. Then, after heating to 90° C., the mixture was reacted for 12 hours. After the reaction was believed to be completed, the reactant was cooled to room temperature, and added dropwise slowly to ice. The reactant was neutralized with a sodium carbonate solution, and the formed solid was then filtered, washed with water and methanol, and dried to obtain a white solid compound (Intermediate 3) (15.3 g, yield: 52.3%).

Synthesis of Compound 1-79

In a 250 mL one-neck flask, Intermediate 3 (3.5 g, 10.9 mmol), phenoxazine (2.1 g, 11.4 mmol), Pd(dba)$_2$ (0.31 g, 0.54 mmol), P(tBu)$_3$ (0.53 mL, 1.1 mmol, 50 wt % toluene solution), NaOtBu (2.1 g, 21.7 mmol), and xylene (54 mL) were refluxed and stirred for one day. The reactant was cooled to room temperature and the impurities were removed by celite filtration. After the solvent was completely removed, the reactant was purified by silica gel column chromatography (EA:CHCl$_3$=1:20). The obtained product was treated with acetone and filtered to obtain Compound 1-79 which is a yellow solid (1.2 g, yield: 29.3%).

(8) Synthesis of Compound 1-80

Compound 1-80 according to an embodiment may be synthesized by, for example, the steps shown in Reaction Formula 8 below:

Reaction Formula 8

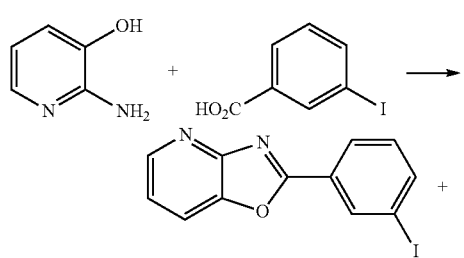

Intermediate 3

Reaction Formula 9

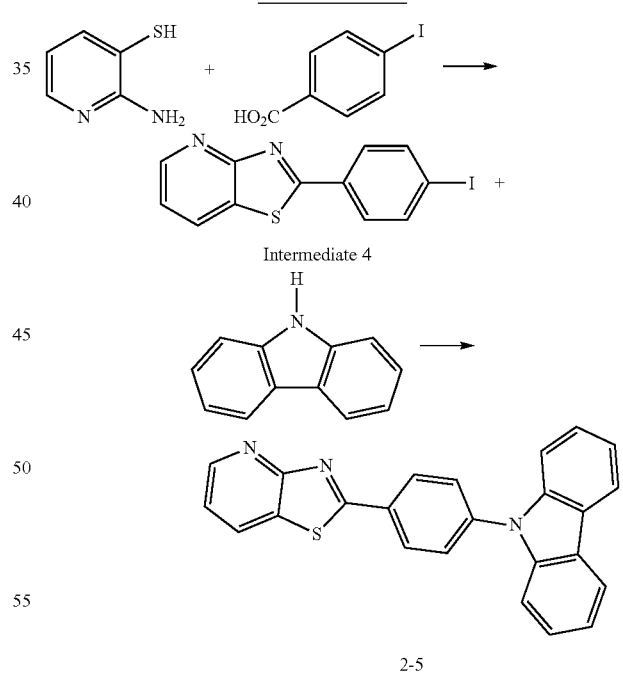

2-5

Synthesis of Intermediate 4

In a 500 mL one-neck flask, 2-aminopyridin-3-thiol (22.9 g, 181.6 mmol) and 4-iodobenzoic acid (45.1 g, 181.6 mmol) were mixed well, and POCl$_3$ (140 mL) was added slowly at 0° C. and then stirred. After heating to 90° C., the mixture was reacted for 12 hours. After the reaction was believed to be completed, the reactant was cooled to room temperature, and added dropwise slowly to ice. The reactant was neutralized with a sodium carbonate solution, and the formed solid was then filtered, washed with water and methanol, and dried to obtain a white solid compound (Intermediate 4) (43.8 g, yield: 71.3%).

Synthesis of Compound 2-5

In a 250 mL one-neck flask, Intermediate 4 (3.7 g, 10.9 mmol), 9H-carbazole (1.5 g, 9.0 mmol), Pd(dba)$_2$ (0.31 g, 0.54 mmol), P(tBu)$_3$ (0.53 mL, 1.1 mmol, 50 wt % toluene solution), NaOtBu (2.1 g, 21.7 mmol), and xylene (54 mL) were refluxed and stirred for one day. The reactant was cooled to room temperature and the impurities were removed by celite filtration. After the solvent was completely removed, the reactant was purified by silica gel column chromatography (EA:CHCl$_3$=1:20). The obtained solid was treated with acetone and filtered to obtain Compound 2-5 which is a yellow solid (1.2 g, yield: 40.7%).

(10) Synthesis of Compound 2-53

Compound 2-53 according to an embodiment may be synthesized by, for example, the steps shown in Reaction Formula 10 below:

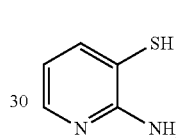

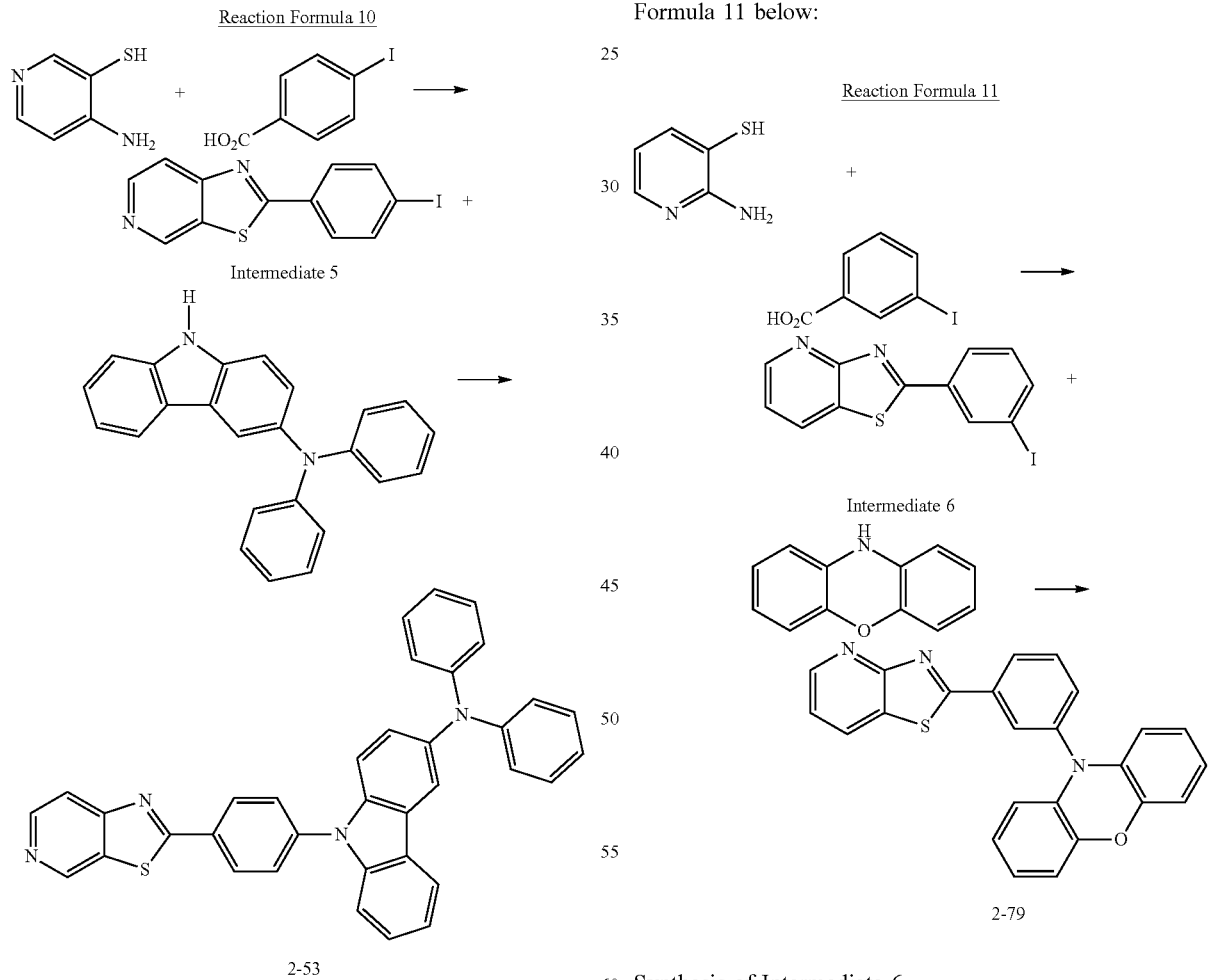

Synthesis of Intermediate 5

In a 250 mL one-neck flask, 4-aminopyridin-3-thiol (5.7 g, 45.4 mmol) and 4-iodobenzoic acid (11.3 g, 45.4 mmol) were mixed well, and POCl$_3$ (40 mL) was added slowly at 0° C. and then stirred. After heating to 90° C., the mixture was reacted for 12 hours. After the reaction was believed to be completed, the reactant was cooled to room temperature, and added dropwise slowly to ice. The reactant was neutralized with a sodium carbonate solution, and the formed solid was then filtered, washed with water and methanol, and dried to obtain a white solid compound (Intermediate 5) (5.7 g, yield: 37.7%).

Synthesis of Compound 2-53

In a 250 mL one-neck flask, Intermediate 5 (1.5 g, 4.5 mmol), N,N-diphenyl-9H-carbazole-3-amine (3.0 g, 9.0 mmol), Pd(dba)$_2$ (0.3 g, 0.5 mmol), P(tBu)$_3$ (0.26 g, 0.5 mmol, 50 wt % toluene solution), NaOtBu (1.5 g, 15.8 mmol), and xylene (45 mL) were refluxed and stirred for one day. The reactant was cooled at room temperature and the impurities were removed by celite filtration. After the solvent was completely removed, the reactant was purified by silica gel column chromatography (MC:HEX=1:8→1:1). Such obtained product was solidified by Acetone:MeOH=2:1, and then filtered to obtain Compound 2-53 which is a red-brown solid (1.5 g, yield: 61.5%).

(11) Synthesis of Compound 2-79

Compound 2-79 according to an embodiment may be synthesized by, for example, the steps shown in Reaction Formula 11 below:

Synthesis of Intermediate 6

In a 250 mL one-neck flask, 2-aminopyridin-3-thiol (10.0 g, 90.8 mmol) and 3-iodobenzoic acid (22.5 g, 90.8 mmol) were mixed well, and POCl$_3$ (70 mL) was added slowly at 0° C. and then stirred. Then, after heating to 90° C., the mixture was reacted for 12 hours. After the reaction was believed to be completed, the reactant was cooled to room temperature, and added dropwise slowly to ice. The reactant was neutralized with a sodium carbonate solution, and the formed solid was then filtered, washed with water and methanol, and dried to obtain a white solid compound (Intermediate 6) (18.2 g, yield: 62.2%).

Synthesis of Compound 2-79

In a 250 mL one-neck flask, Intermediate 6 (3.5 g, 10.9 mmol), phenoxazine (2.1 g, 11.4 mmol), Pd(dba)$_2$ (0.31 g, 0.54 mmol), P(tBu)$_3$ (0.53 mL, 1.1 mmol, 50 wt % toluene solution), NaOtBu (2.1 g, 21.7 mmol), and xylene (54 mL) were refluxed and stirred for one day. The reactant was cooled to room temperature and the impurities were removed by celite filtration. After the solvent was completely removed, the reactant was purified by silica gel column chromatography (EA:CHCl$_3$=1:20). The obtained product was treated with acetone and filtered to obtain Compound 2-79 which is a yellow solid (1.4 g, yield: 33.8%).

2. Evaluation of Compound

The fluorescence luminous characteristics of the compound of an embodiment were evaluated. The luminous characteristics of Comparative Example Compounds were evaluated along with those of the compound of an embodiment. The compounds used in the evaluation are shown in below.

(Compounds Used in Evaluation of Luminous Characteristics)

1-1
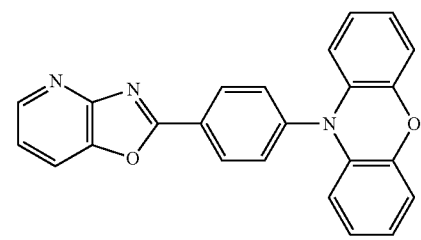

1-5
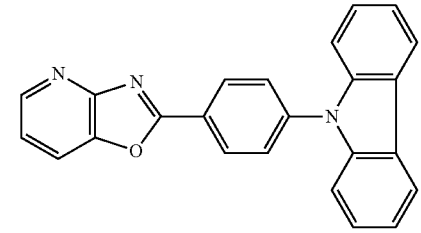

1-43
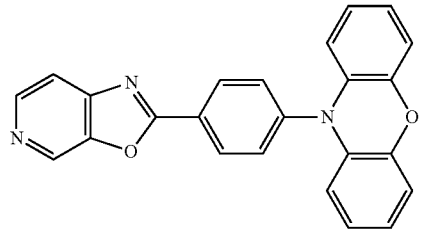

1-47
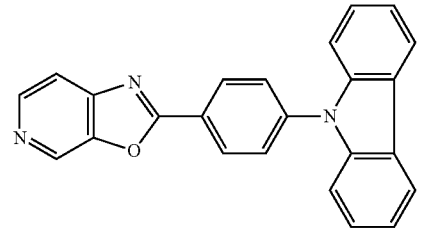

1-79
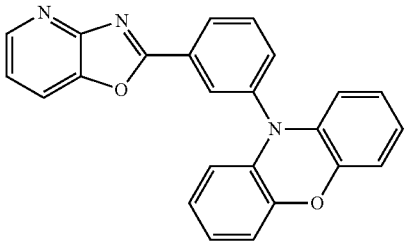

1-80
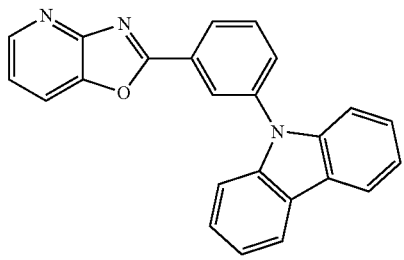

2-5
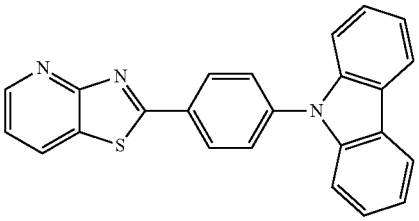

2-53
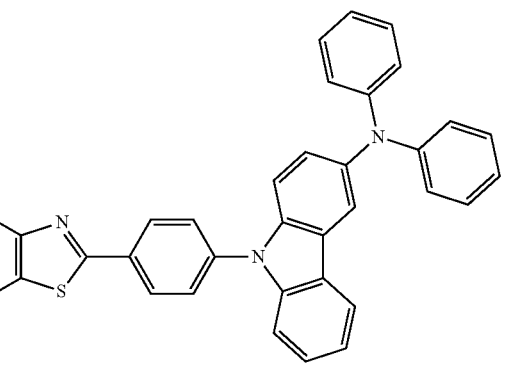

2-79
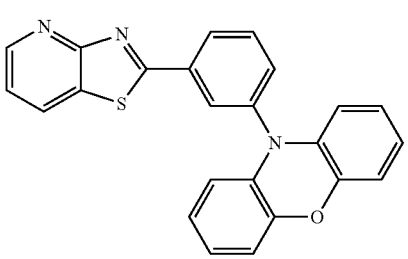

Comparative Example Compounds Used in Evaluation of Luminous Characteristics

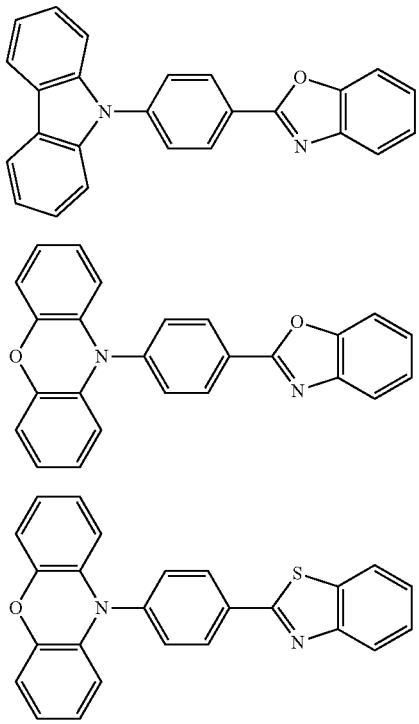

With respect to the compounds of Examples and Comparative Example Compounds, $\Delta E_{ST}$ value and luminous wavelength were evaluated and shown in Table 1. The results of characteristic evaluation are shown in Table 1. $\Delta E_{ST}$ corresponds to a difference between a lowest singlet excitation energy level (S1 level) and a lowest triplet excitation energy level (T1 level), and was calculated using a Gaussian calculation method (basis set B3LYP/6-31G*). That is, density functional theory calculations were performed utilizing a Gaussian software package from Gaussian Inc., utilizing the B3LYP hybrid functional and 6-31G* basis set. Furthermore, the luminous wavelength of Example Compounds and Comparative Example Compounds was identified using a luminescence spectrum.

TABLE 1

| Division | $\Delta E_{ST}$ | Luminous wavelength |
|---|---|---|
| Compound 1-1 | 0.01 eV | Green |
| Compound 1-5 | 0.06 eV | Blue |
| Compound 1-43 | 0.02 eV | Green |
| Compound 1-47 | 0.09 eV | Blue |
| Compound 1-79 | 0.02 eV | Green |
| Compound 1-80 | 0.09 eV | Blue |
| Compound 2-5 | 0.08 eV | Blue |
| Compound 2-53 | 0.09 eV | Blue |
| Compound 2-79 | 0.02 eV | Green |
| Comparative Example Compound C1 | 0.50 eV | Blue |
| Comparative Example Compound C2 | 0.20 eV | Green |
| Comparative Example Compound C3 | 0.25 eV | Green |

Referring to the results of Table 1, the compounds of Examples each may be used as a luminescence material which emits blue light or green light. In addition, it is considered that the compounds of Examples each have a small $\Delta E_{ST}$ value of less than 0.20 eV, and may be used as a delayed fluorescence emitting material.

Manufacture and Evaluation of Organic Electroluminescence Device 3-1. Example a of Organic Electroluminescence Device Including Compound of One Embodiment An organic electroluminescence device of an embodiment including a compound of an embodiment as a host material in an emission layer was manufactured as follows.

Manufacture of Organic Electroluminescence Device

A glass substrate on which ITO is patterned was washed with pure water and then irradiated with ultraviolet rays for about 30 minutes and treated with ozone. Then, HT1 was deposited on the glass substrate to a thickness of about 1,200 Å, and HT2 was deposited on the glass substrate to a thickness of about 100 Å to form a hole transport region.

Next, when forming an emission layer, a compound of an Example or a compound of a Comparative example and 4CzIPN were co-deposited in a ratio of 80:20 to form a layer having a thickness of 400 Å. That is, with respect to the emission layer which is formed by co-depositing, a compound of the present disclosure and 4CzIPN were mixed and deposited in the Example, and a compound of a Comparative Example and 4CzIPN were mixed and deposited in the Comparative Example, respectively.

Then, ET and Liq were mixed in 5:5 and deposited on the emission layer to form a layer having a thickness of about 300 Å, and then a layer having a thickness of about 10 Å was formed with Liq to form an electron transport region. Next, a second electrode having a thickness of about 100 Å was formed by Mg:Ag (10:1)

In the Examples and Comparative Examples, the hole transport region, the emission layer, the electron transport region, and the second electrode were formed using a vacuum deposition apparatus.

A hole transport region material, an electron transport region material, and a dopant material used in manufacture of the organic electroluminescence device are shown below.

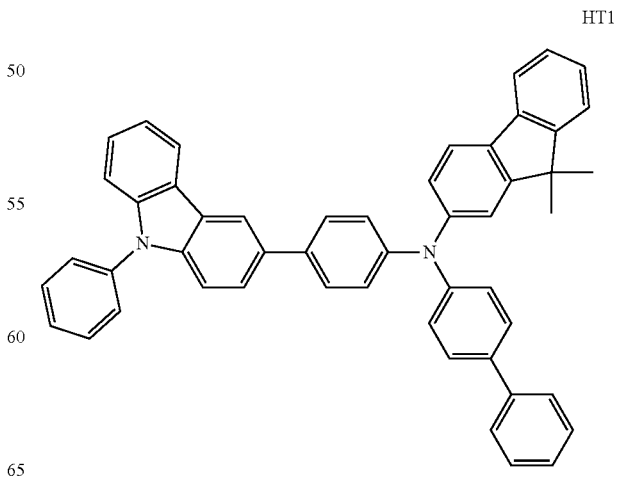

-continued

HT2

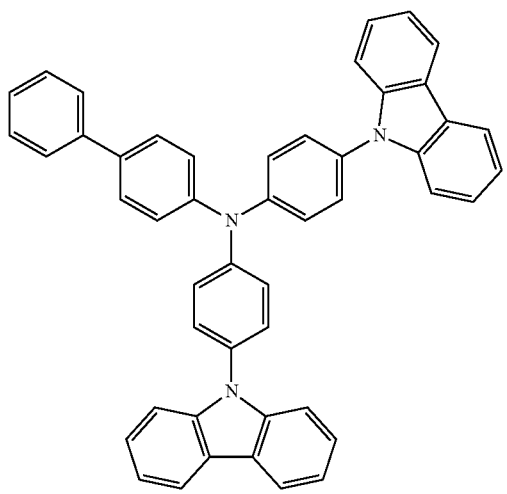

ET

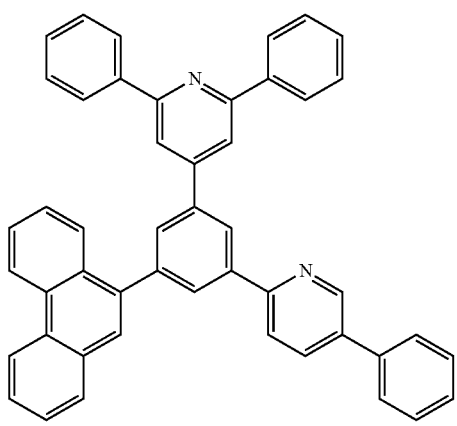

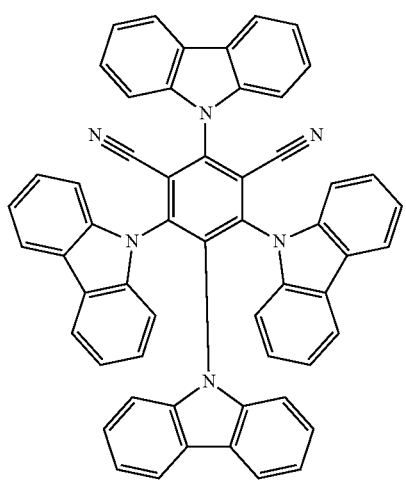

4CzIPN

Furthermore, compounds used in Example 1-1 and Example 1-2 are shown below.

1-51

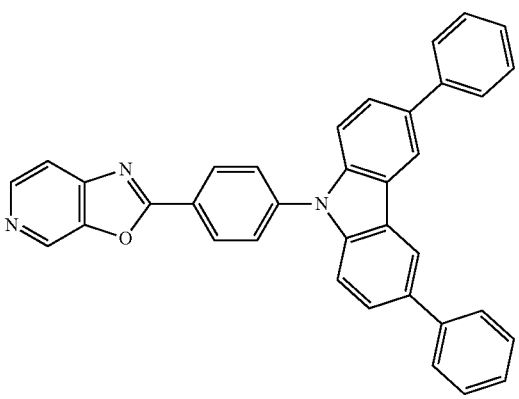

1-58

Evaluation of Property of Organic Electroluminescence Device

Efficiency, service life, and luminous color of the manufactured organic electroluminescence devices are listed in Table 2 for comparison. In the results of characteristic evaluation with respect to Examples and Comparative Examples shown in Table 2, the efficiency represents current efficiency values with respect to current density of 10 mA/cm$^2$. In addition, in characteristic evaluation of the organic electroluminescence devices, efficiency and service life in Examples are represented as relative value for comparison when it is assumed that efficiency and service life in Comparative Example 1-1 are 100%.

In Example 1-1 and Example 1-2, Compound 1-51 and Compound 1-58 each were used respectively as a host material of the emission layer. In Comparative Example 1-1, mCBP which is an existing host material was used as a host material of the emission layer.

TABLE 2

| Division | Host | Dopant | Efficiency | Service life | Luminous color |
|---|---|---|---|---|---|
| Examples 1-1 | Compound 1-51 | 4CzIPN | 105% | 155% | Green |
| Examples 1-2 | Compound 1-58 | 4CzIPN | 110% | 170% | Green |
| Comparative Example 1-1 | mCBP | 4CzIPN | 100% | 100% | Green |

Referring to the results of Table 2, it may can be seen that all of Example 1-1, Example 1-2, and Comparative Example 1-1 emit light in the green wavelength region. In the case of Example 1-1 and Example 1-2, it can be seen that both of efficiency and service life characteristics are improved as compared with Comparative Example 1-1.

Therefore, it may be seen that the compound according to an embodiment may be used as a host material of the emission layer to emit light in the green wavelength region, and exhibits improved luminous efficiency and excellent service life characteristics compared with the case of use of the existing host material.

3-2. Example B of Organic Electroluminescence Device Including Compound of One Embodiment The organic electroluminescence device of an embodiment including the compound of an embodiment as a dopant material in the emission layer was manufactured as follows.

Manufacture of Organic Electroluminescence Device

A glass substrate on which ITO is patterned was washed with pure water and then irradiated with ultraviolet rays for about 30 minutes and treated with ozone. Then, HT1 was deposited on the glass substrate to a thickness of about 1,200 Å, and HT2 was deposited on the glass substrate to a thickness of about 100 Å to form a hole transport region.

Next, when forming an emission layer, a compound of an Example or a compound of a Comparative Example and mCBP were co-deposited in a ratio of 20:80 to form a layer having a thickness of 400 Å. That is, with respect to the emission layer which is formed by co-depositing, a compound of an Example and mCBP were mixed and deposited in the Example, and a compound of a Comparative Example and mCBP were mixed and deposited in the Comparative Example, respectively.

Then, ET and Liq were mixed in 5:5 and deposited on the emission layer to form a layer having a thickness of about 300 Å, and then a layer having a thickness of about 10 Å was formed with Liq to form an electron transport region. Next, a second electrode having a thickness of about 100 Å was formed by Mg:Ag (10:1)

In the Examples and Comparative Examples, the hole transport region, the emission layer, the electron transport region, and the second electrode were formed using a vacuum deposition apparatus.

Evaluation of Property of Organic Electroluminescence Device

Efficiency, service life, and luminous color of the manufactured organic electroluminescence device are listed in Table 3 for comparison. In the results of characteristic evaluation with respect to Examples and Comparative Examples shown in Table 3, the efficiency represents current efficiency values with respect to current density of 10 mA/cm². In addition, in characteristic evaluation of the organic electroluminescence device, efficiency and service life of Examples is represented by comparing with a relative value when efficiency and service life of Comparative Example 2-1 or Comparative Example 3-1 are considered 100%.

In the evaluation shown in Table 3 below, Example 2-1 to Example 2-4, Comparative Example 2-1 and Comparative Example 2-2 show the evaluation results with respect to the organic electroluminescence device which emits light in the green wavelength region, and Example 3-1 to Example 3-5 and Comparative Example 3-1 show the evaluation results with respect to the organic electroluminescence device which emits light in the blue wavelength region. In Example 2-1 to Example 2-4, Comparative Example 2-1 and Comparative Example 2-2, Example 3-1 to Example 3-5, and Comparative Example 3-1, mCBP which is an existing host material was used as a host material of the emission layer.

TABLE 3

| Division | Host | Dopant | Efficiency | Service life | Luminous color |
|---|---|---|---|---|---|
| Examples 2-1 | mCBP | Compound 1-1 | 130% | 140% | Green |
| Examples 2-2 | mCBP | Compound 1-43 | 120% | 130% | Green |
| Examples 2-3 | mCBP | Compound 1-79 | 120% | 125% | Green |
| Examples 2-4 | mCBP | Compound 2-79 | 115% | 120% | Green |
| Comparative Example 2-1 | mCBP | Comparative Example Compound C2 | 100% | 100% | Green |
| Comparative Example 2-2 | mCBP | Comparative Example Compound C3 | 95% | 90% | Green |
| Examples 3-1 | mCBP | Compound 1-5 | 120% | 115% | Blue |
| Examples 3-2 | mCBP | Compound 1-47 | 130% | 125% | Blue |
| Examples 3-3 | mCBP | Compound 1-80 | 120% | 120% | Blue |
| Examples 3-4 | mCBP | Compound 2-5 | 115% | 120% | Blue |
| Examples 3-5 | mCBP | Compound 2-53 | 125% | 125% | Blue |
| Comparative Example 3-1 | mCBP | Comparative Example Compound C1 | 100% | 100% | Blue |

Referring to the results of Table 3, it can be seen that Examples may be used as the organic electroluminescence devices which emit green light or blue light and the compounds according to an embodiment may be used as a green dopant which emits green light or a blue dopant which emits blue light.

Further, referring to the results of Table 3, it can be seen that Example 2-1 to Example 2-4 exhibit improved excellent efficiency characteristics and long service life characteristics as compared with Comparative Example 2-1 and Comparative Example 2-2, and Example 3-1 to Example 3-5 exhibit improved efficiency characteristics and excellent service life characteristics as compared with Comparative Example 3-1.

Therefore, referring to the evaluation result of Table 3, it may be identified that the compounds according to an embodiment are used as a dopant material of the emission layer of the organic electroluminescence device and emit green light or blue light. Further, it may be seen that when the compound of an embodiment is used as a dopant material of the emission layer, including aza-type benzoxazole (e.g., an aza-benzoxazole) moiety, the compound exhibits effect of improving efficiency and service life characteristics of the organic electroluminescence device.

The compound of an embodiment may have a novel compound structure including the Aza-type benzoxazole (e.g., an aza-benzoxazole) or Aza-type benzothiazole (e.g., an aza-benzothiazole) moiety as an electron-accepting part, and may be used as an emission layer material to contribute to high efficiency and long service life characteristics of the organic electroluminescence device. Furthermore, the organic electroluminescence device of an embodiment including the compound of an embodiment in the emission layer may exhibit high efficiency characteristics and improved service life characteristics in a green wavelength region or a blue wavelength region.

The organic electroluminescence device according to an embodiment of the present disclosure may exhibit improved device properties such as high efficiency and long service life in a green wavelength region or a blue wavelength region.

The compounds of an embodiment may be included in the emission layer of the organic electroluminescence device to improve life properties of the organic electroluminescence device and contribute to high efficiency.

Although described with reference to example embodiments of the present disclosure, it will be understood that various changes and modifications to the subject matter of the present disclosure may be made by one skilled in the art or one having ordinary knowledge in the art without departing from the spirit and technical field of the present disclosure as hereinafter claimed.

Hence, the technical scope of the present disclosure is not limited to the detailed descriptions in the specification, but it should be determined only by the appended claims, and equivalents thereof.

What is claimed is:

1. An organic electroluminescence device comprising:
   a first electrode;
   a second electrode on the first electrode; and
   an emission layer which is between the first electrode and the second electrode and includes a compound represented by the following Formula 1:

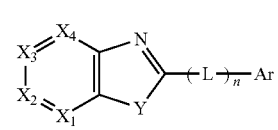

Formula 1 in Formula 1,
at least one selected from among $X_2$ to $X_4$ is N, the rest are $CR_a$, or each of $X_1$ and $X_4$ among $X_1$ to $X_4$ is N, the rest are $CR_a$,
Y is O or S,
n is 1 or 2,
L is an unsubstituted phenylene or an unsubstituted pyridinylene,
$R_a$ is a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or is combined with an adjacent group to form a ring, and
Ar is represented by the following Formula 2:

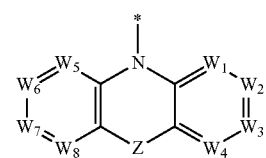

Formula 2 in Formula 2,
$W_1$ to $W_8$ are each independently N or $CR_b$,
Z is a direct linkage, O, or $CR_cR_d$, and
$R_b$ to $R_d$ are each independently a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or are combined with an adjacent group to form a ring.

2. The organic electroluminescence device of claim 1, wherein Formula 1 above is represented by the following Formula 1-1 or Formula 1-2 below:

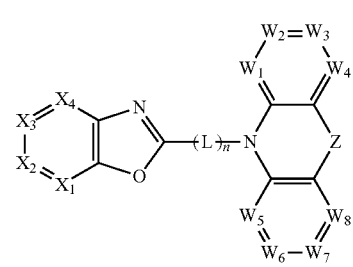

Formula 1-1

Formula 1-2

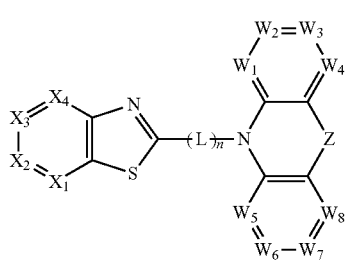

in Formula 1-1 and Formula 1-2, $X_1$ to $X_4$, L, n, Z, and $W_1$ to $W_8$ are the same as those defined with respect to Formula 1 and Formula 2.

3. The organic electroluminescence device of claim 1, wherein Formula 2 is represented by any one selected from the following Formula 2-1 to Formula 2-4 below:

Formula 2-1

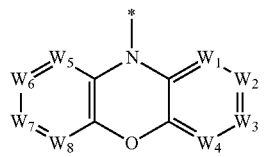

Formula 2-2

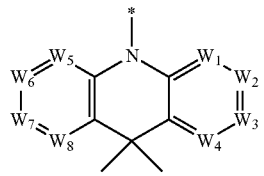

Formula 2-3

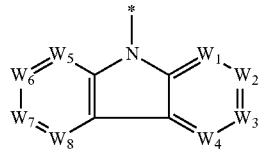

Formula 2-4

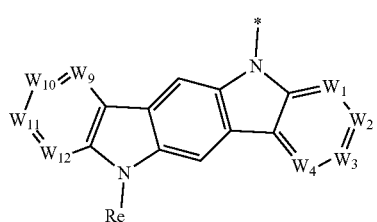

in Formula 2-4,
$R_e$ is a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring,
$W_9$ to $W_{12}$ are each independently N or $CR_f$,
$R_f$ is a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or are combined with an adjacent group to form a ring, and
in Formula 2-1 to Formula 2-4, $W_1$ to $W_8$ are the same as those defined with respect to Formula 2.

4. The organic electroluminescence device of claim 1, wherein Ar is represented by any one selected from the following Ar-1 to Ar-6:

Ar-1

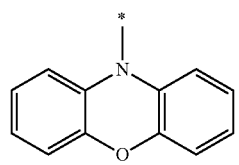

Ar-2

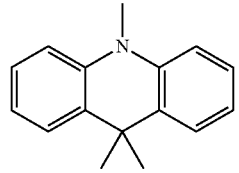

Ar-3

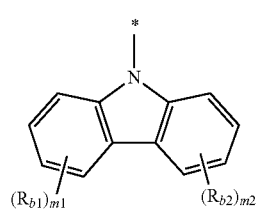

$(R_{b1})_{m1}$ $(R_{b2})_{m2}$

Ar-4

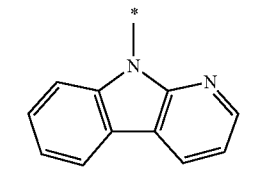

Ar-5

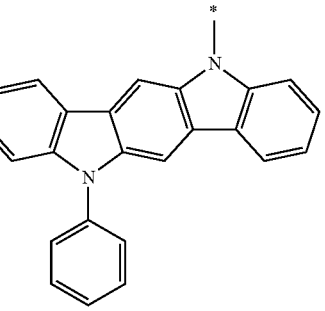

Ar-6

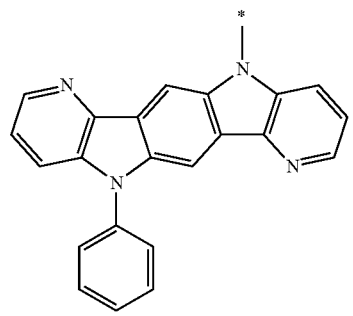

in Ar-3, m1 and m2 are each independently 0 or 1, and R$_{b1}$ and R$_{b2}$ are each independently a hydrogen atom, a deuterium atom, a substituted or unsubstituted arylamine group having 6 to 30 carbon atoms for forming a ring, or a substituted or unsubstituted aryl group having 6 to 30 carbon atoms for forming a ring.

5. The organic electroluminescence device of claim 1, wherein L is represented by any one selected from the following L-1 and L-2

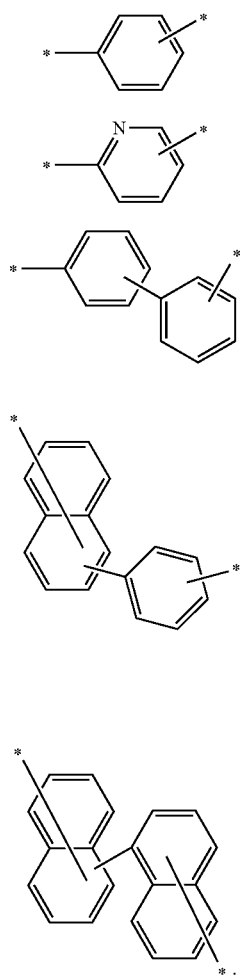

6. The organic electroluminescence device of claim 1, wherein the emission layer comprises a host and a dopant, and the host comprises the compound.

7. The organic electroluminescence device of claim 1, wherein the emission layer emits a delayed fluorescence, and the compound is a delayed fluorescence dopant.

8. The organic electroluminescence device of claim 1, wherein the emission layer emits light having a center wavelength of 500 nm or more and 550 nm or less, or light having a center wavelength of 450 nm or more and less than 500 nm.

9. The organic electroluminescence device of claim 1, wherein the emission layer comprises at least one selected from compounds represented in the following Compound Group 1 and Compound Group 2:

Compound Group 1

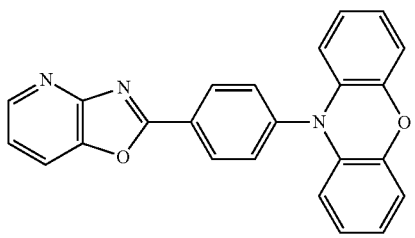
1-1

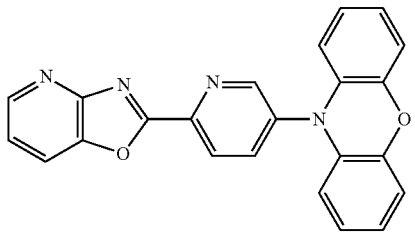
1-2

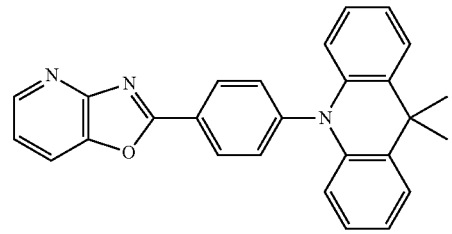
1-3

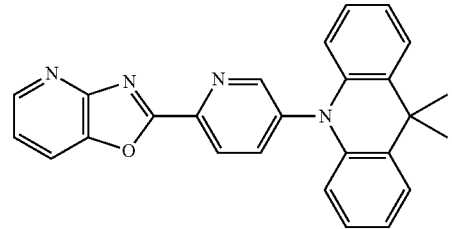
1-4

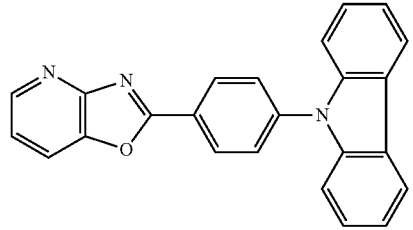
1-5

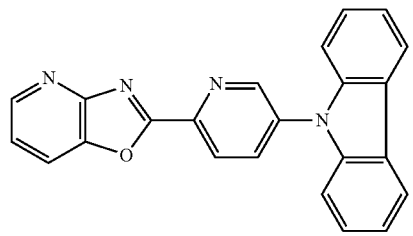
1-6

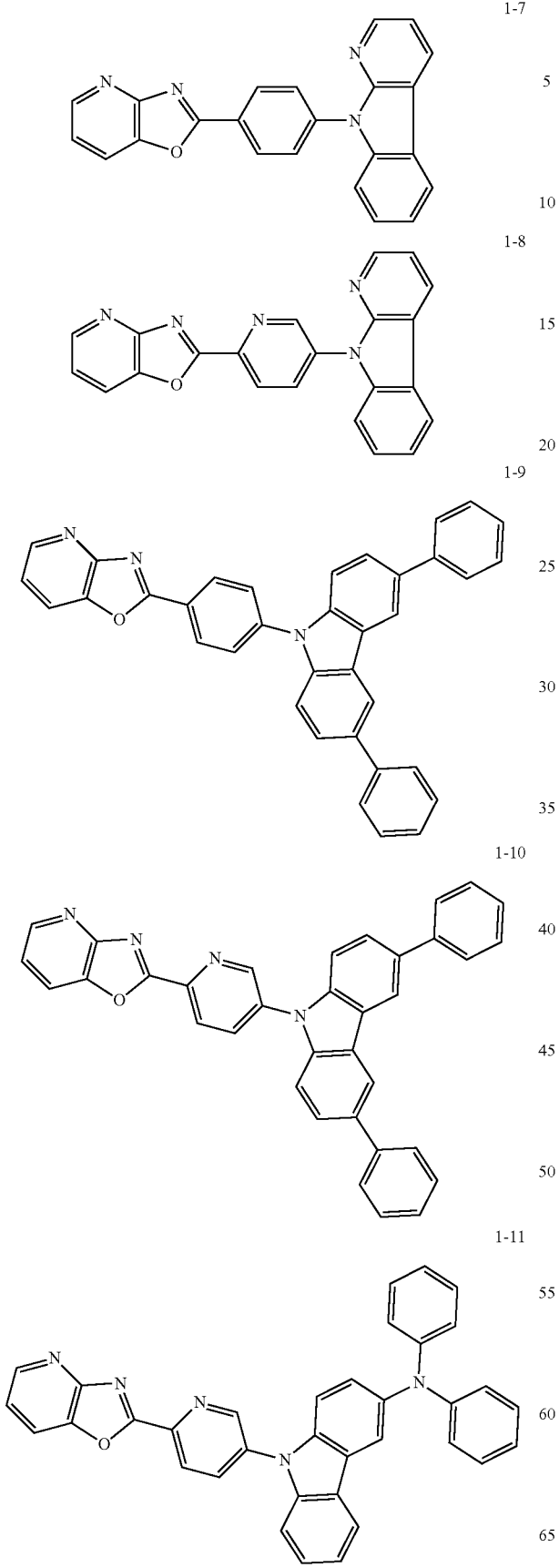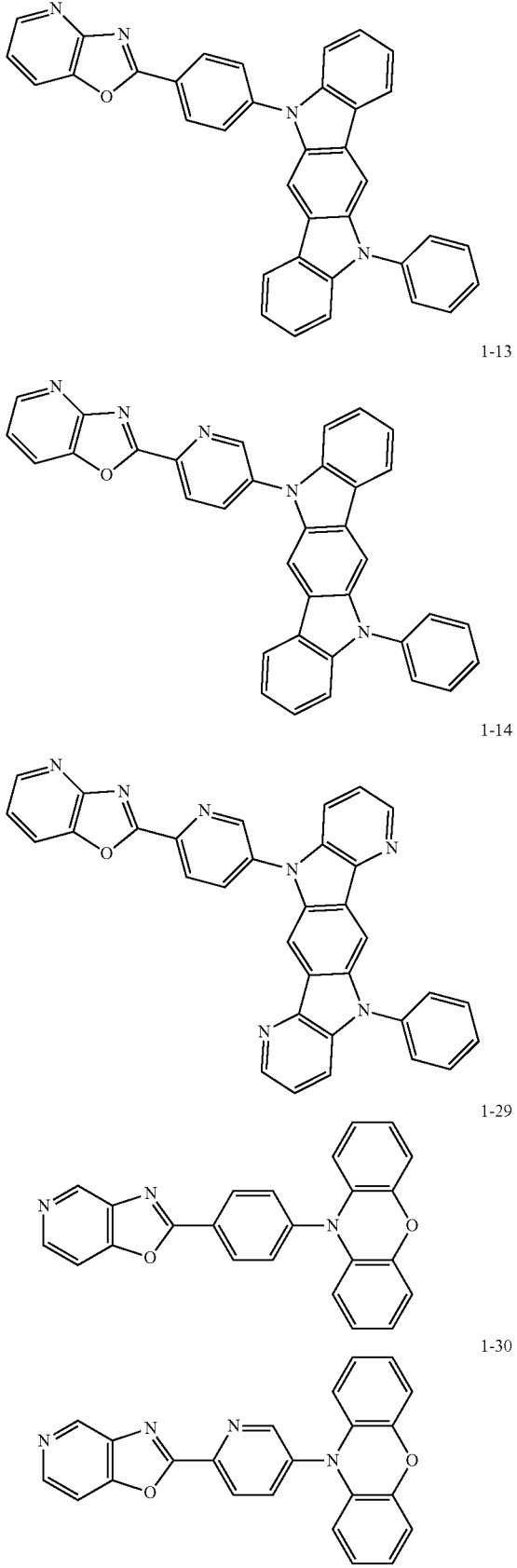

1-31
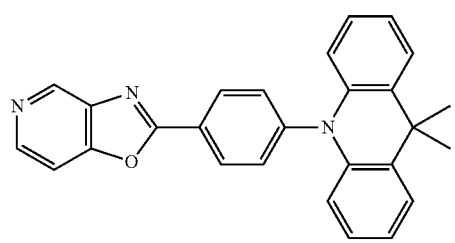
1-32
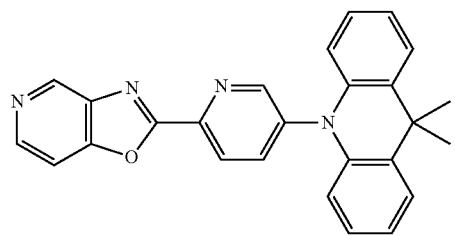
1-33
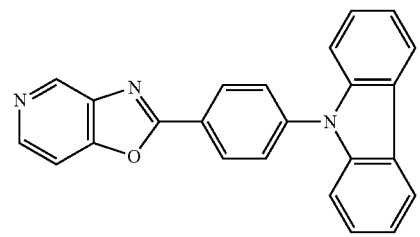
1-34
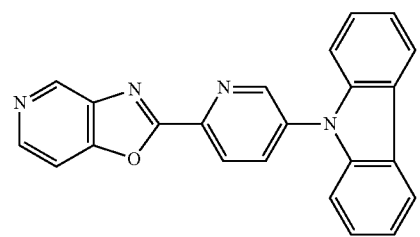
1-35
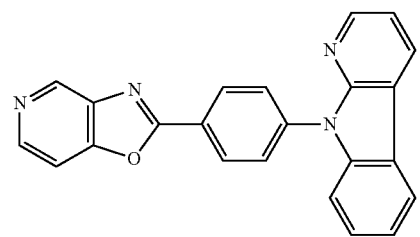
1-36
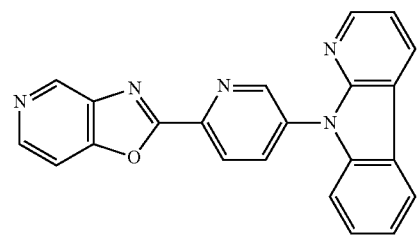
1-37
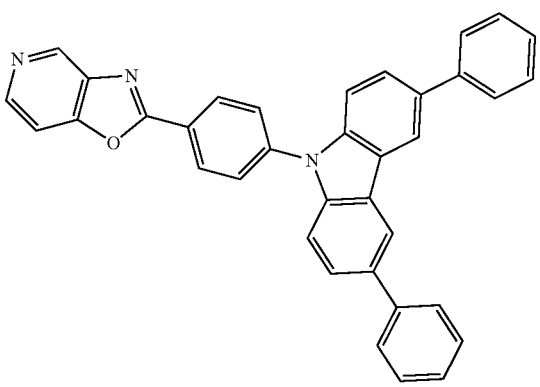
1-38
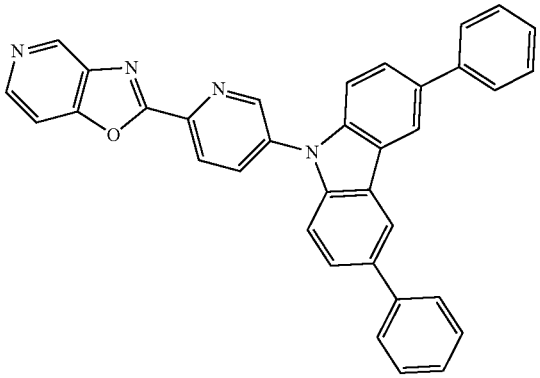
1-39
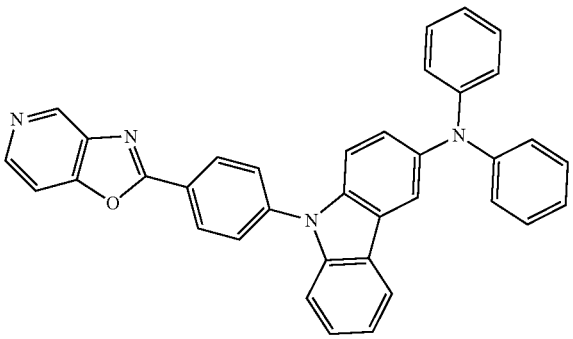
1-40
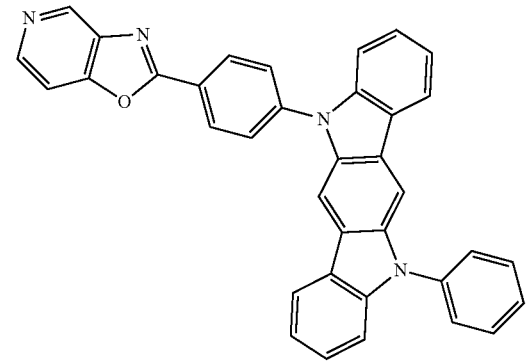

1-41
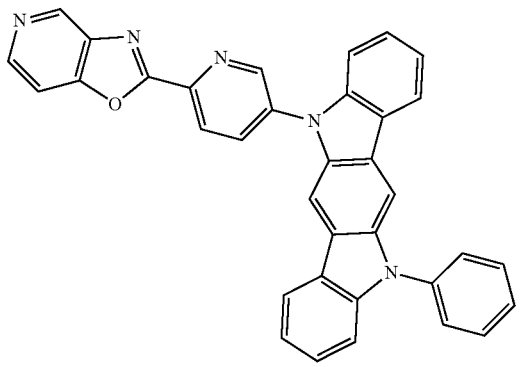
1-42
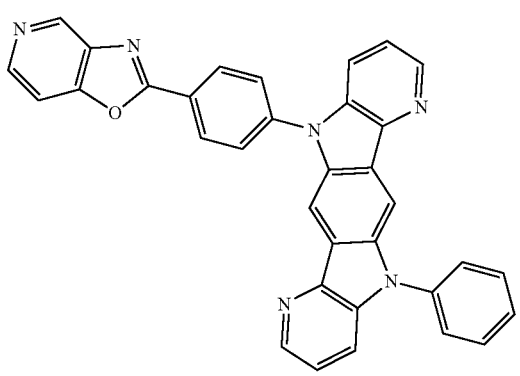
1-43
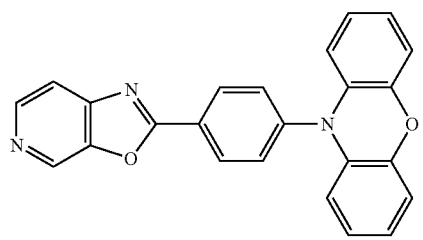
1-44
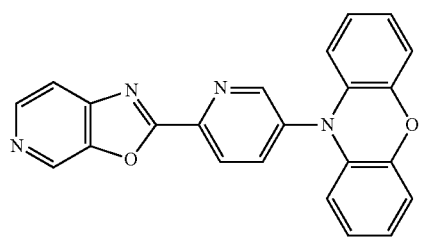
1-45
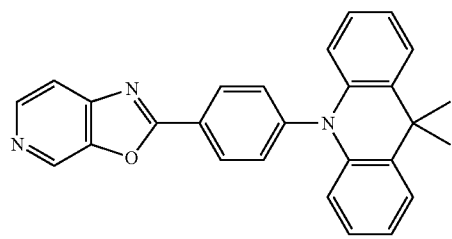
1-46
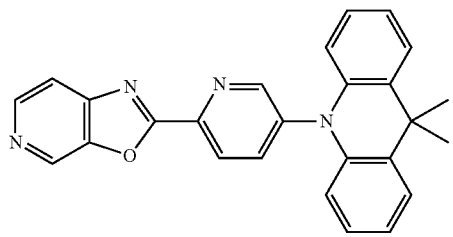
1-47
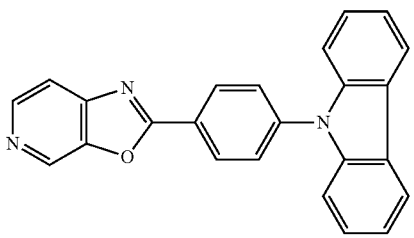
1-48
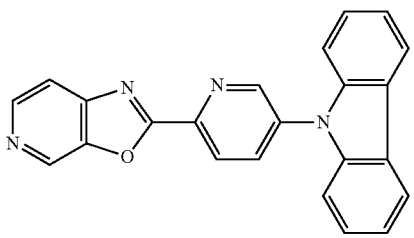
1-49
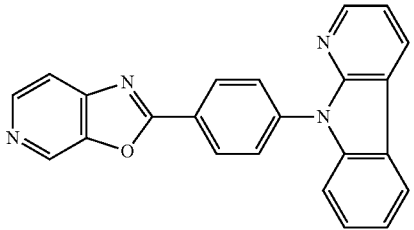
1-50
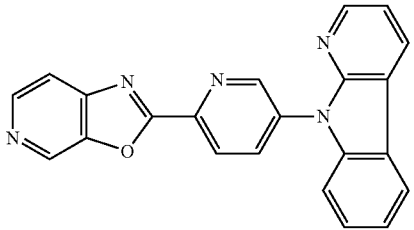
1-51
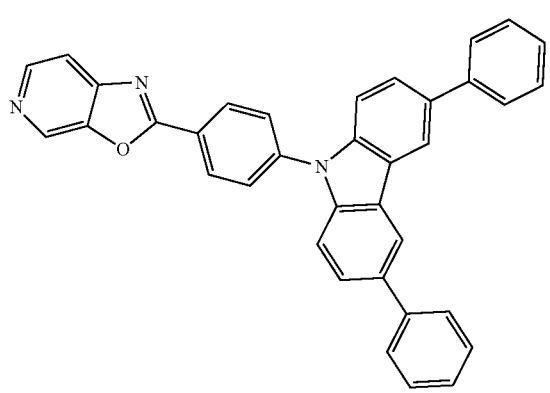

-continued
1-52
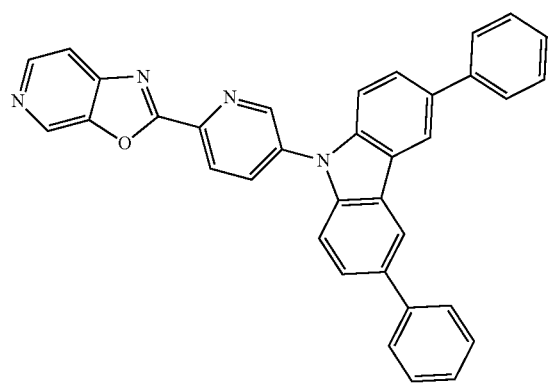
1-53
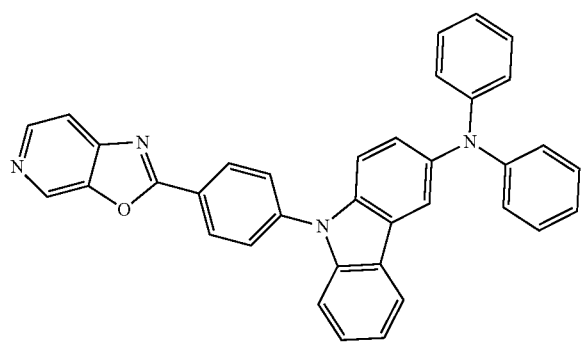
1-54
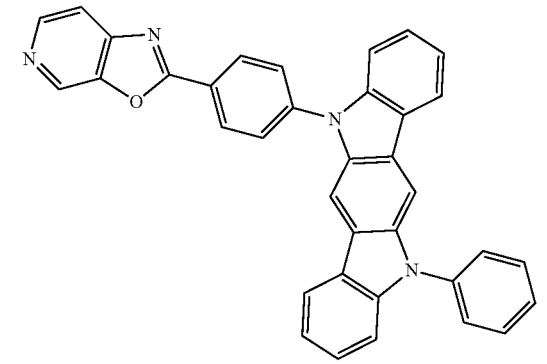
1-55
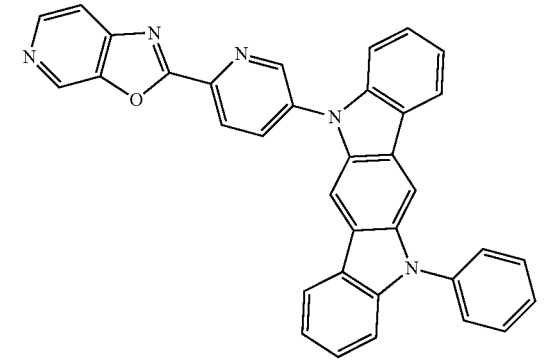
-continued
1-56
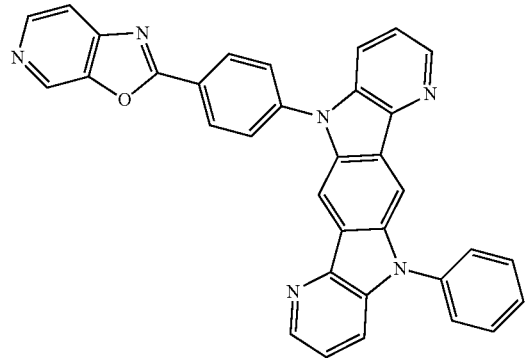
1-57
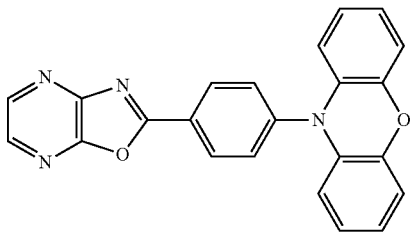
1-58
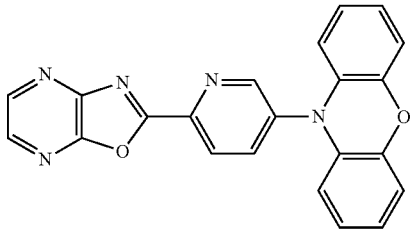
1-59
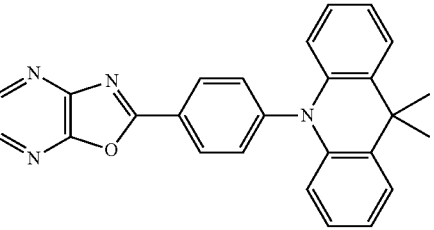
1-60
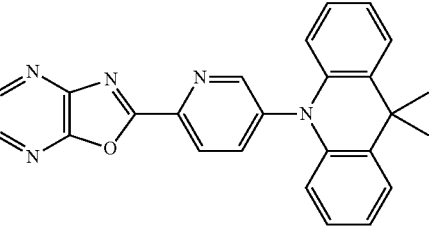
1-61
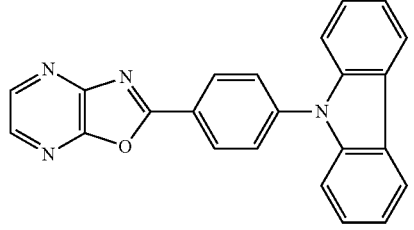

1-62
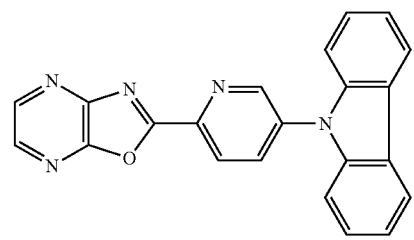
1-63
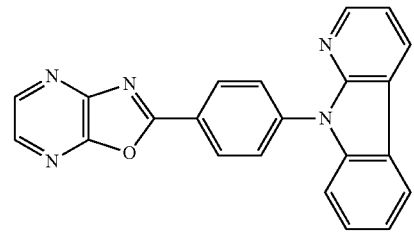
1-64
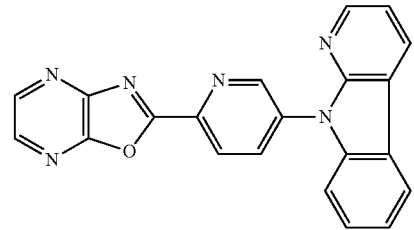
1-65
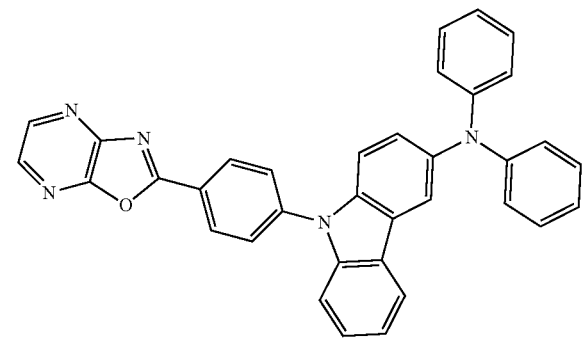
1-66
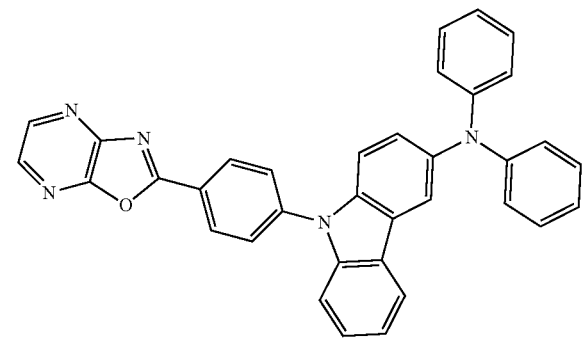
1-67
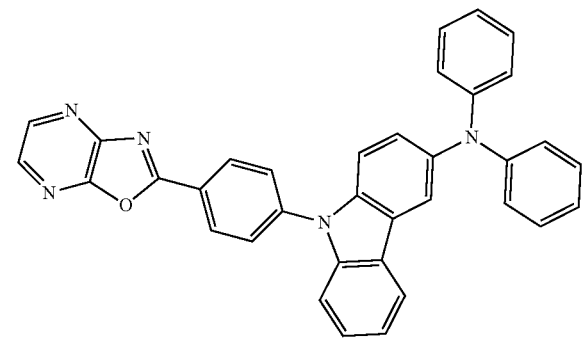
1-68
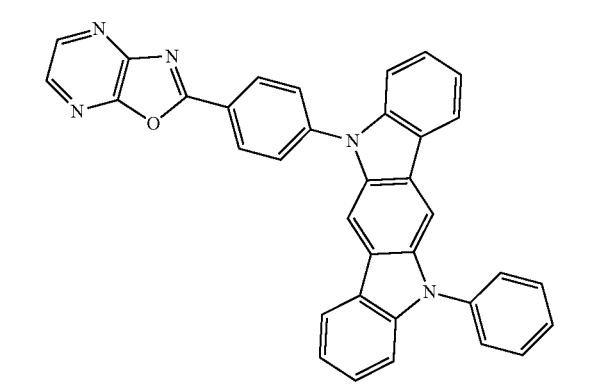
1-69
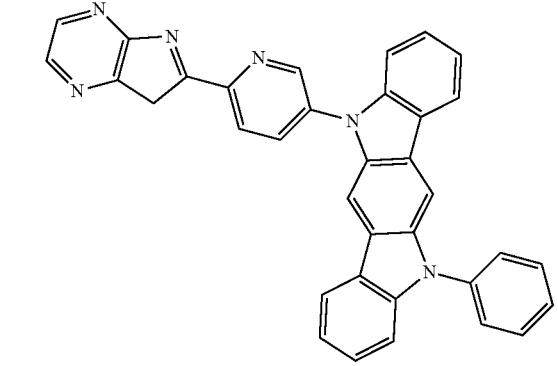
1-70
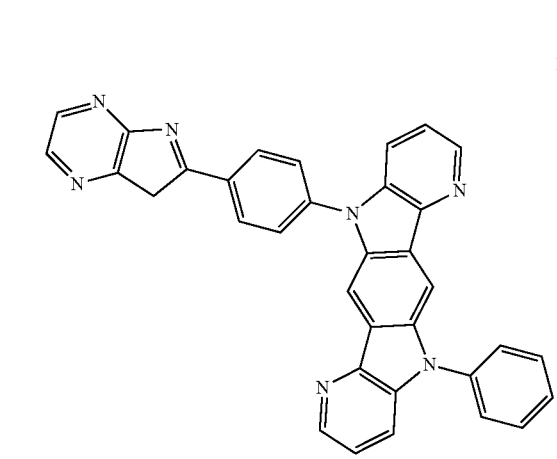

1-71
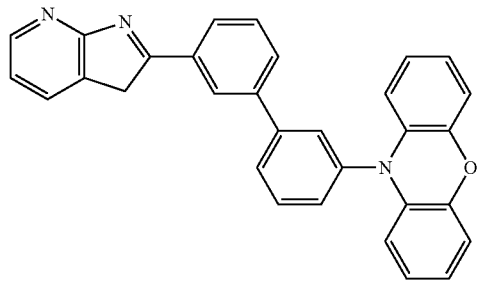
1-72
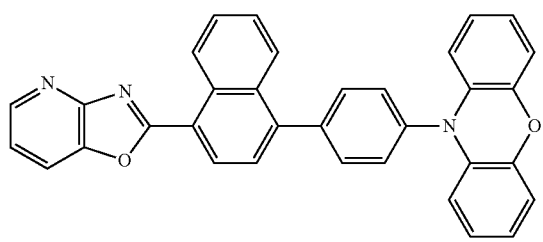
1-73
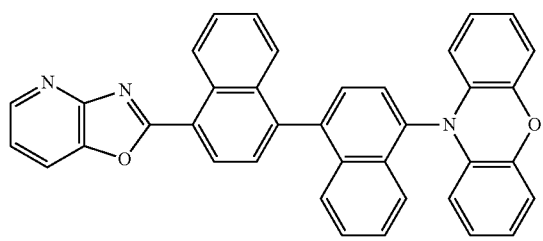
1-74
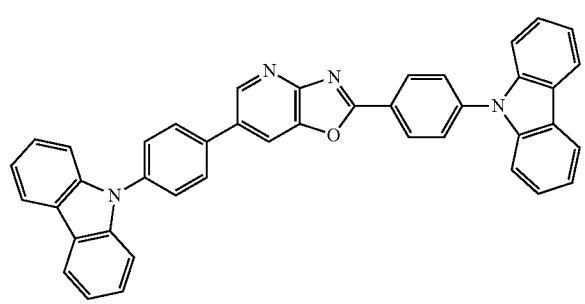
1-75
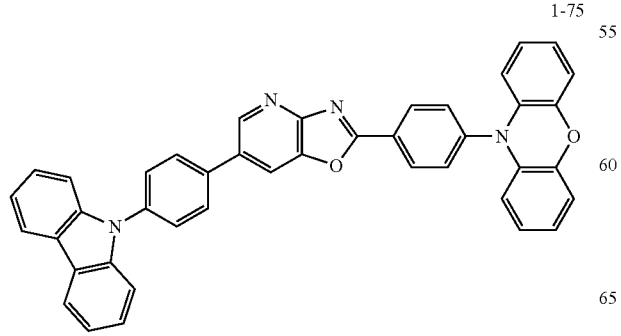
1-76
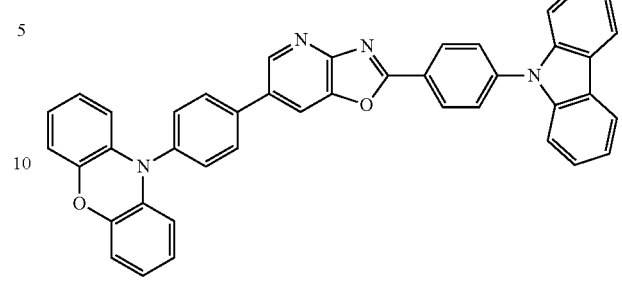
1-77
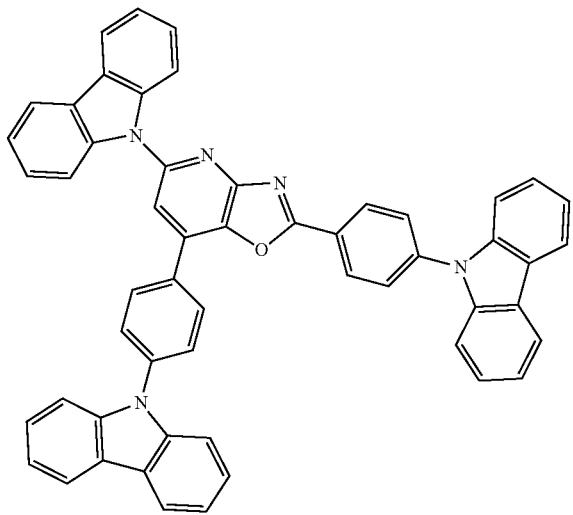
1-78
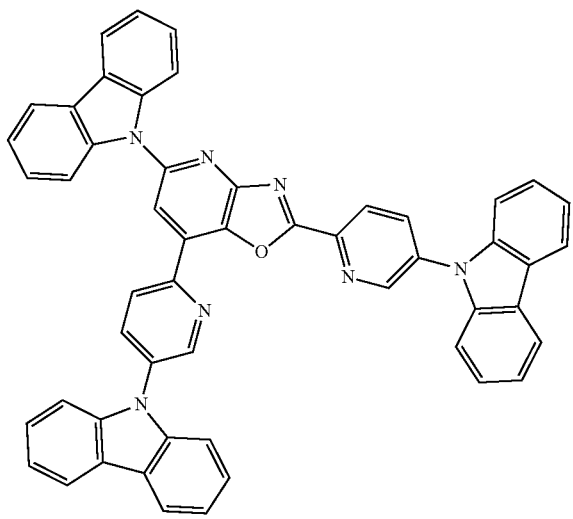
1-79
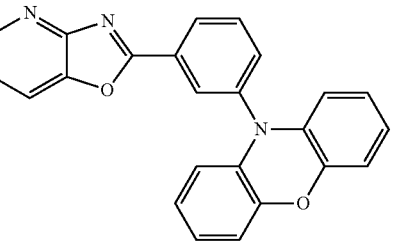

1-80
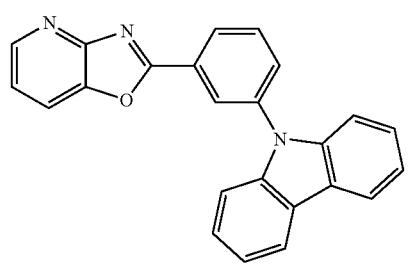
Compound Group 2
2-1
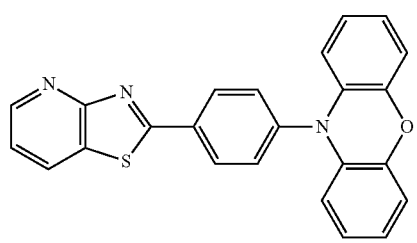
2-2
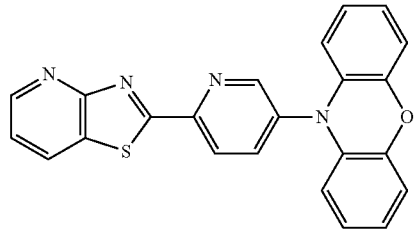
2-3
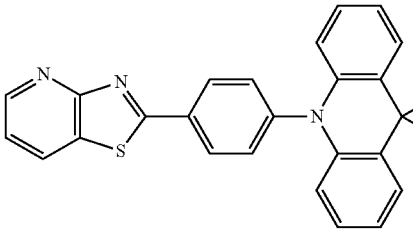
2-4
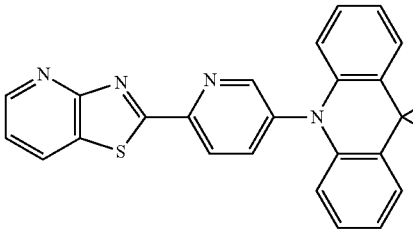
2-5
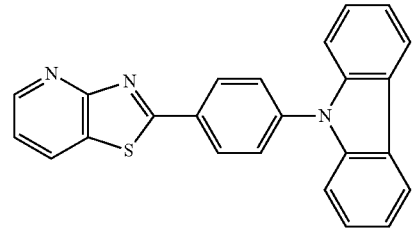
2-6
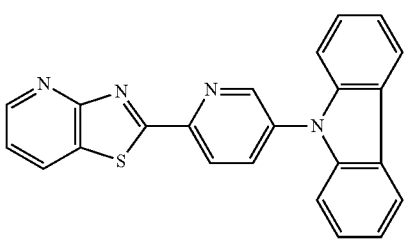
2-7
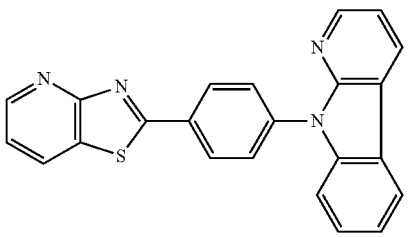
2-8
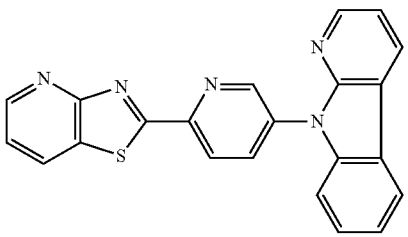
2-9
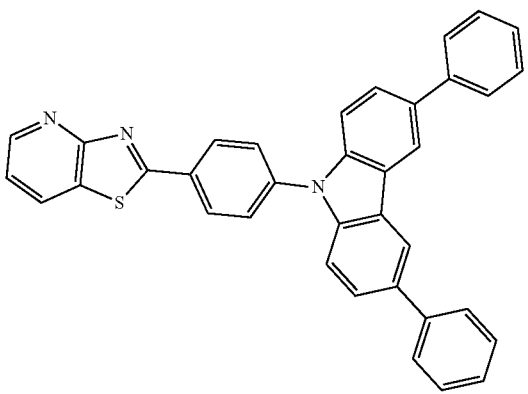
2-10
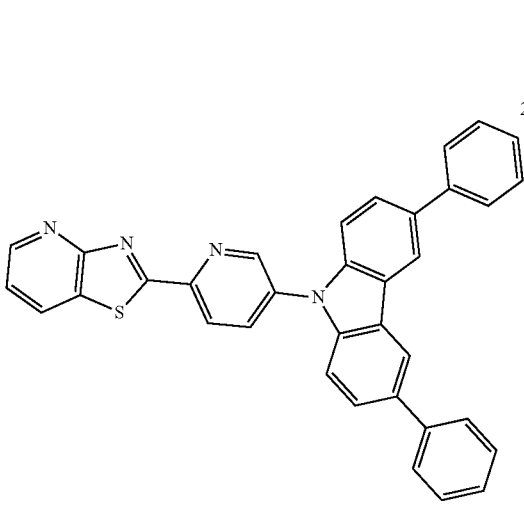

2-11
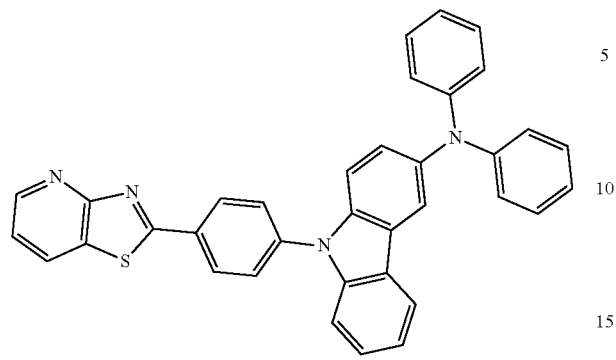
2-12
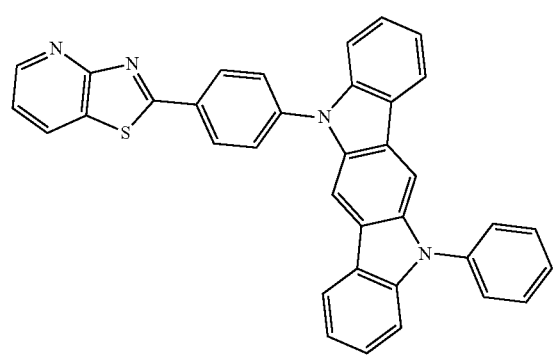
2-13
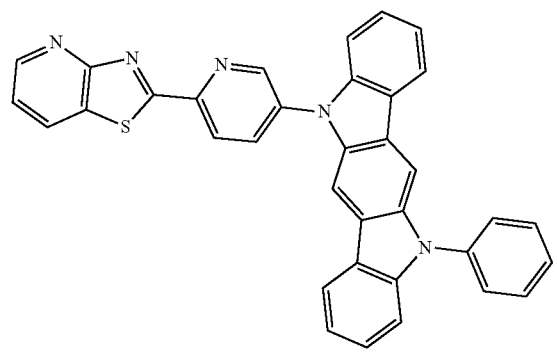
2-14
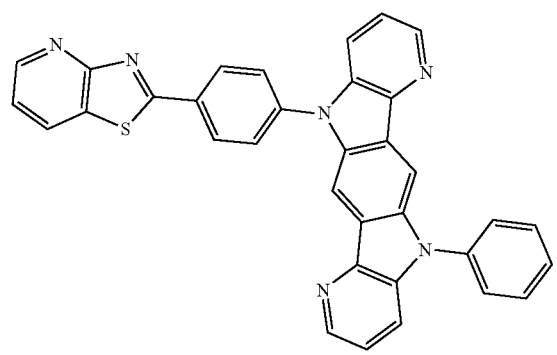
2-29
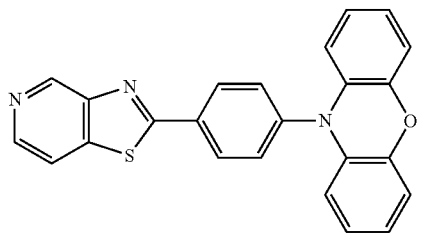
2-30
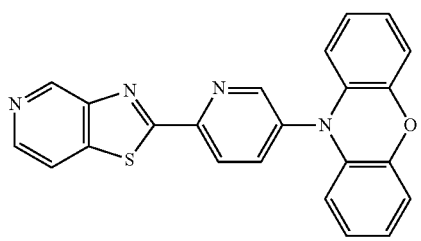
2-31
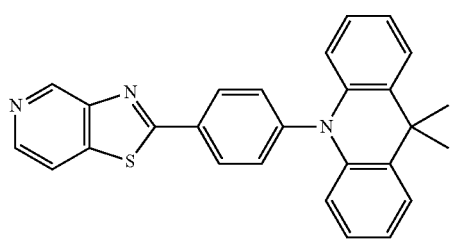
2-32
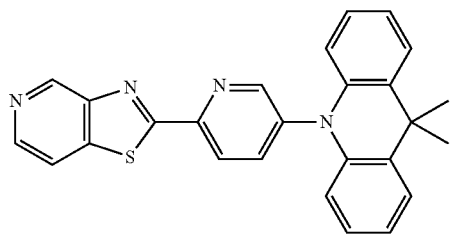
2-33
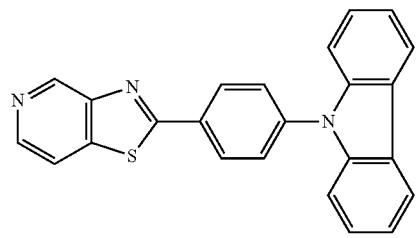
2-34
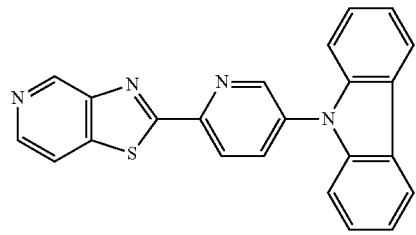

95
-continued
2-35
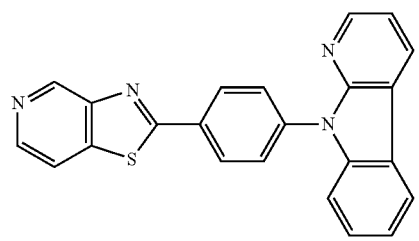
2-36
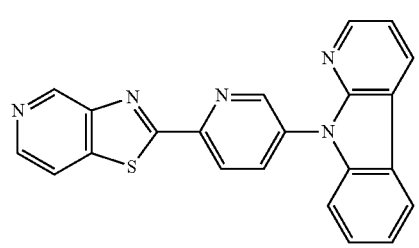
2-37
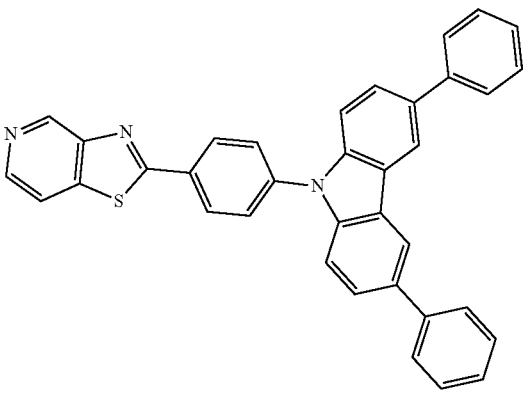
2-38
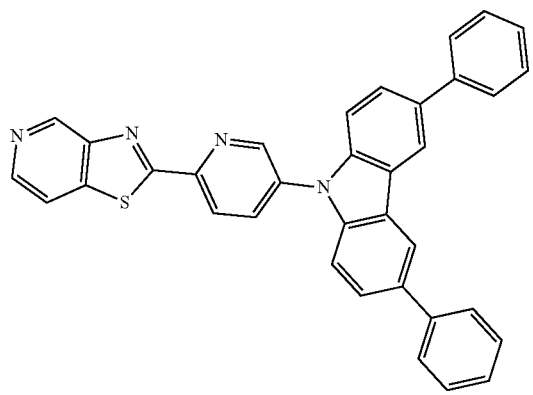
96
-continued
2-39
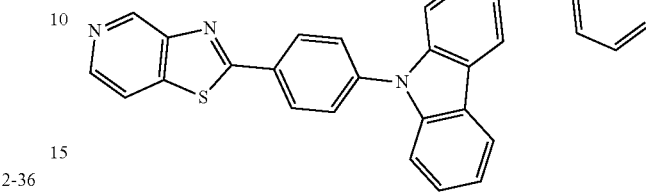
2-40
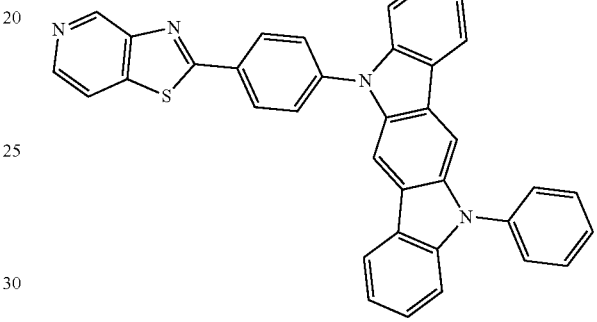
2-41
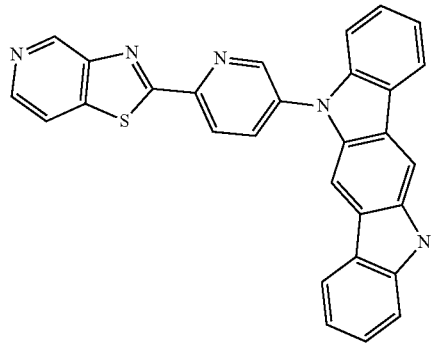
2-42
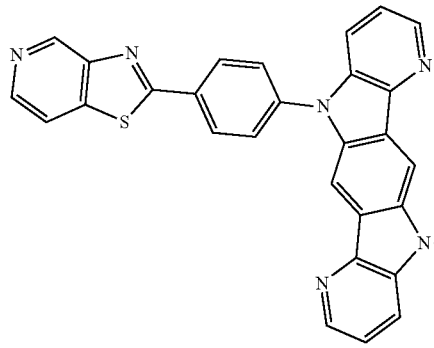

2-43
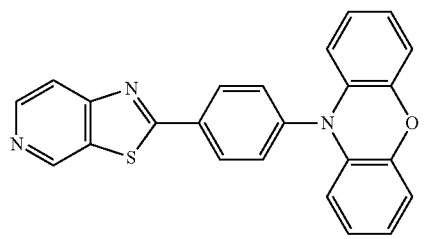
2-44
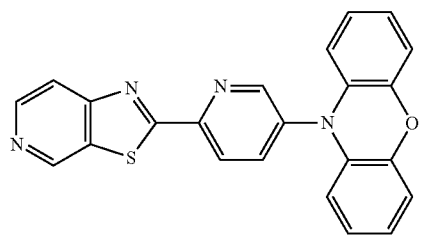
2-45
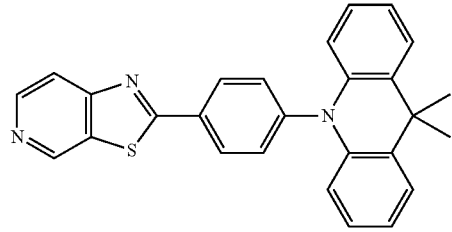
2-46
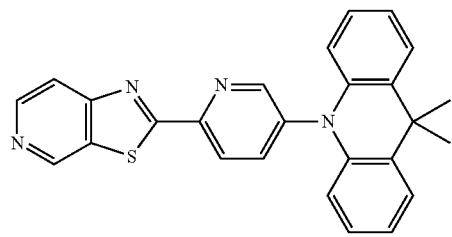
2-47
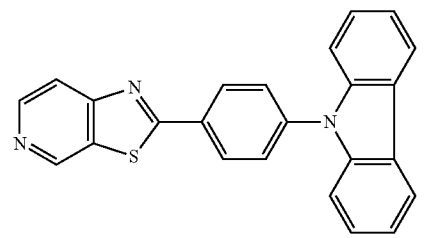
2-48
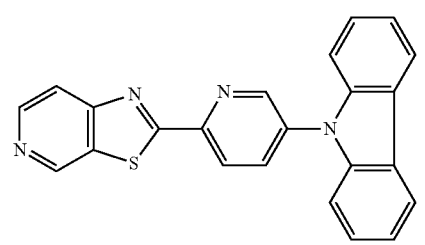
2-49
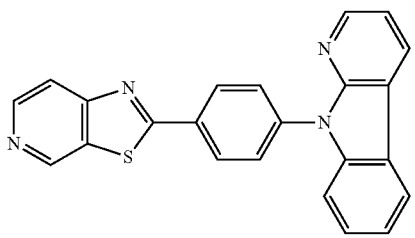
2-50
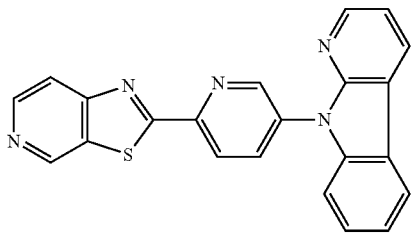
2-51
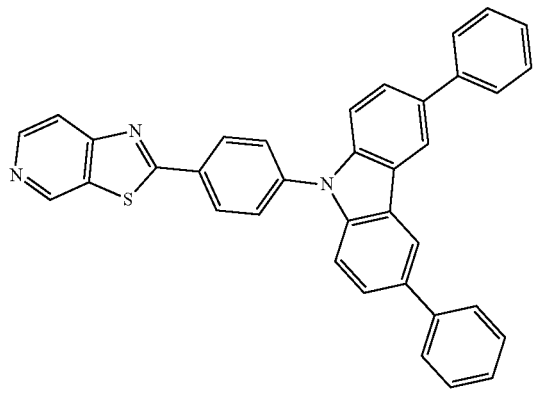
2-52
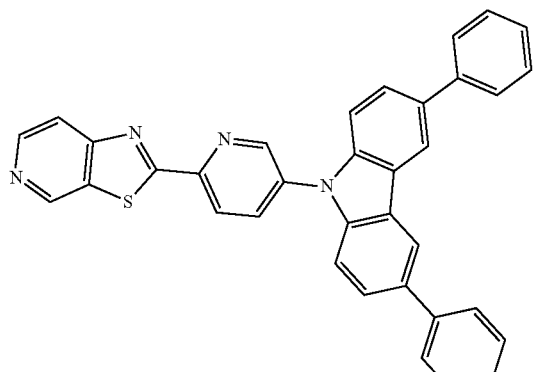

2-53
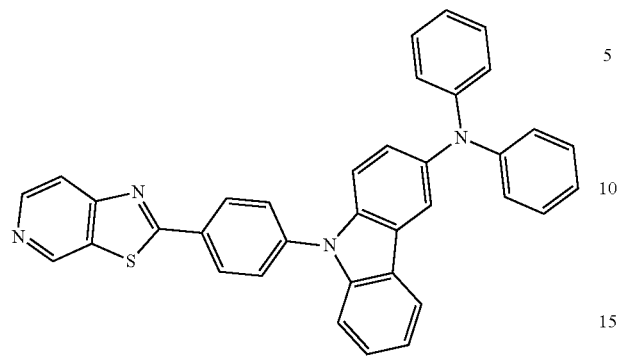
2-54
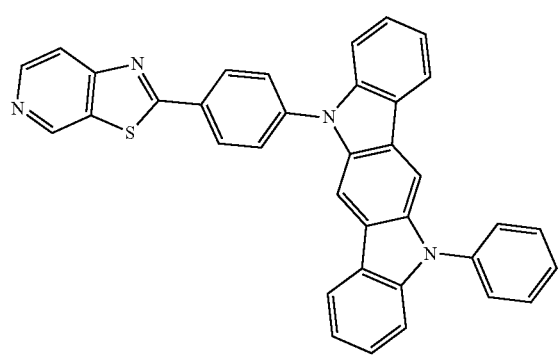
2-55
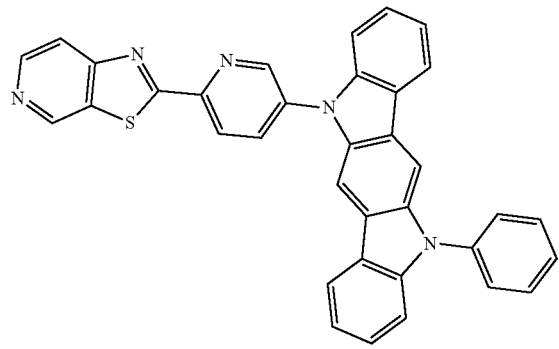
2-56
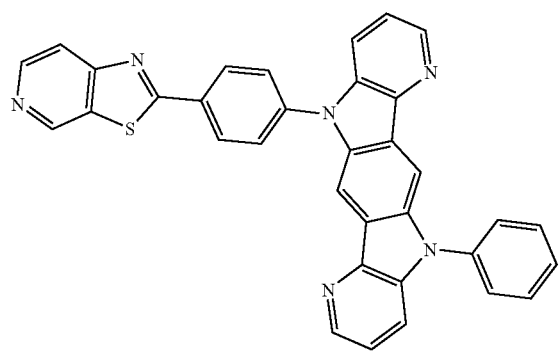
2-57
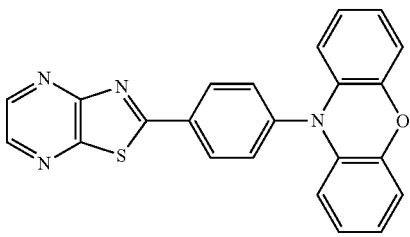
2-58
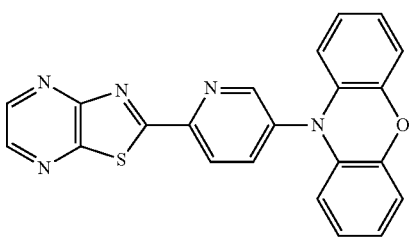
2-59
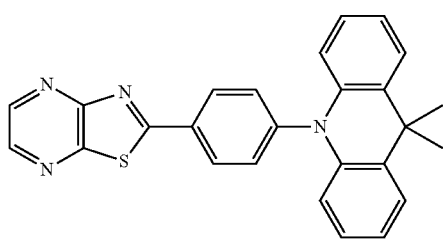
2-60
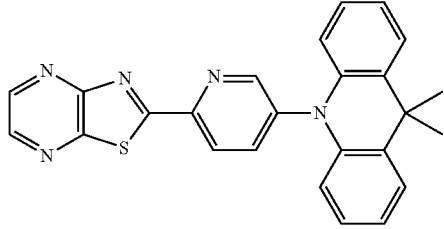
2-61
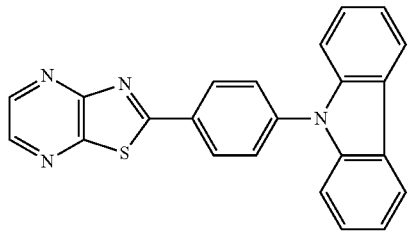
2-62
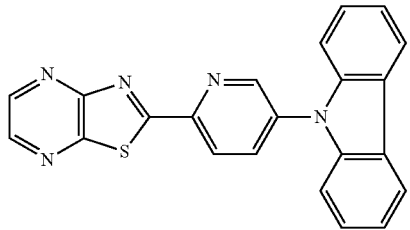

2-63
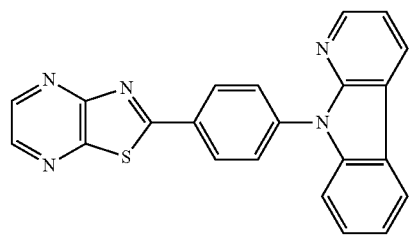
2-64
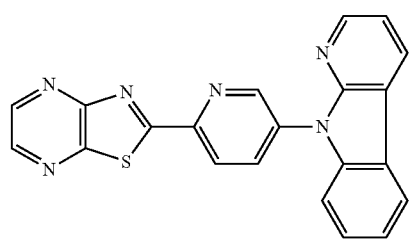
2-65
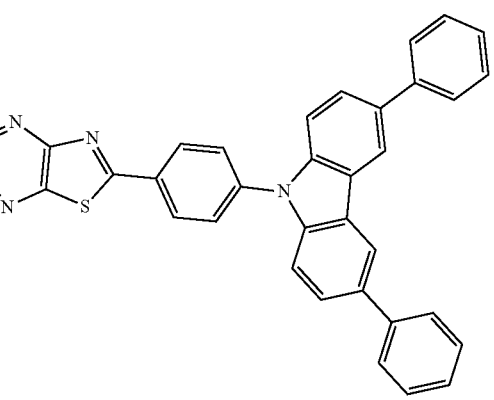
2-66
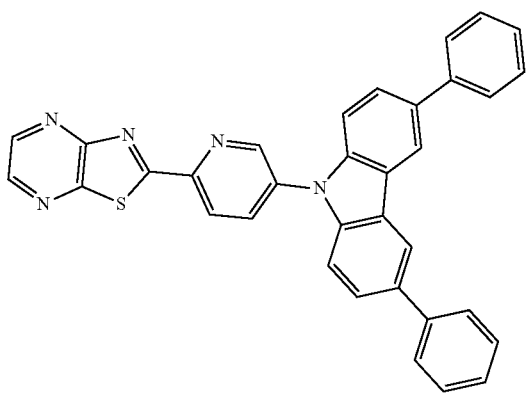
2-67
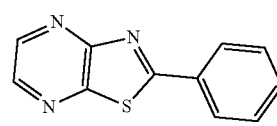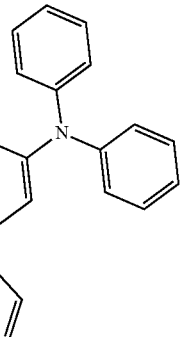
2-68
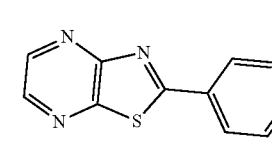
2-69
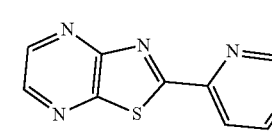
2-70
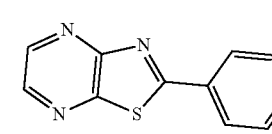

-continued
2-71
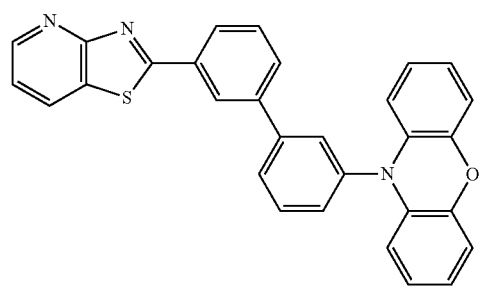
2-72
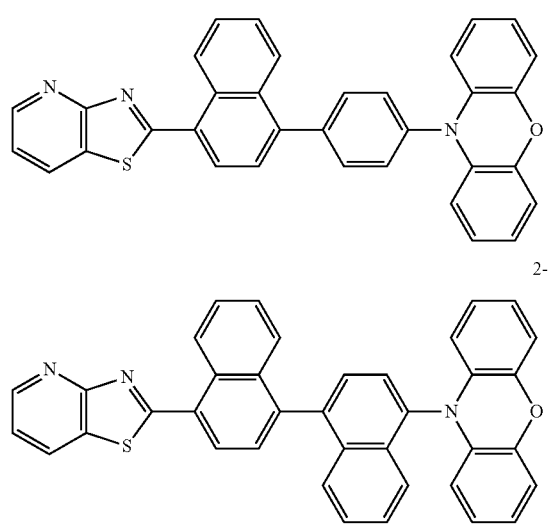
2-73
2-74
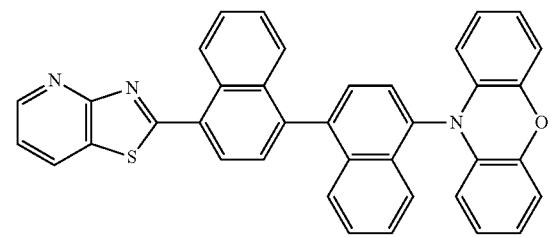
2-75
-continued
2-76
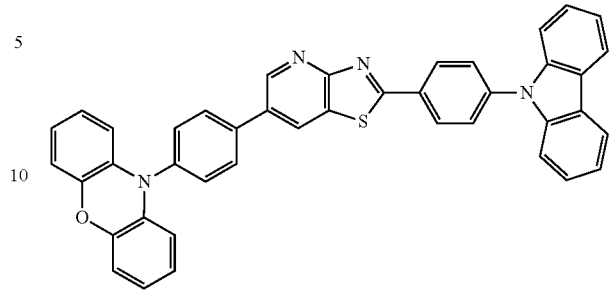
2-77
2-78
2-79
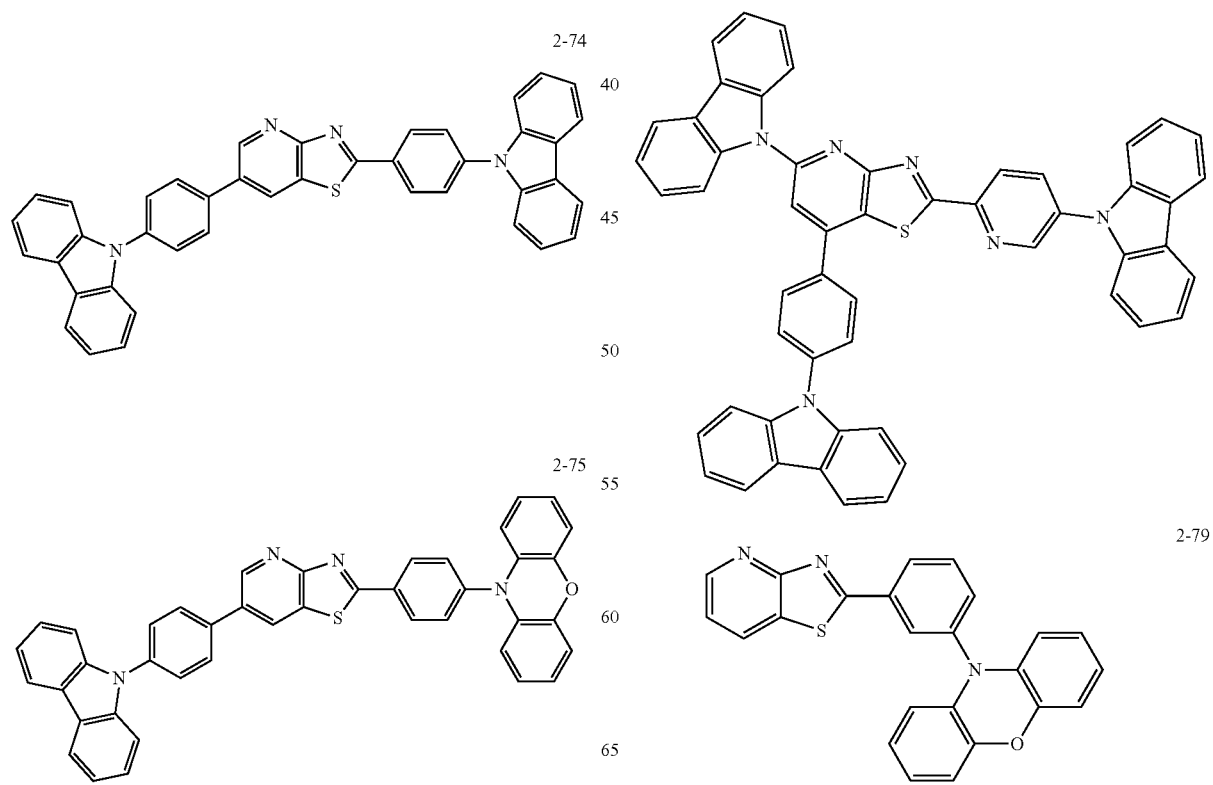

105

-continued 2-80

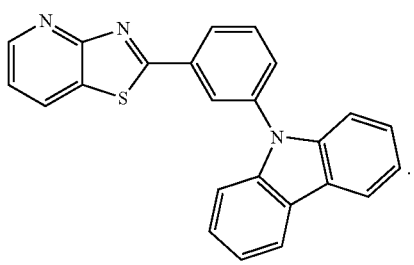

10. A compound represented by the following Formula 1:

Formula 1

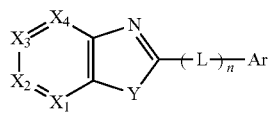

in Formula 1, at least one selected from among $X_2$ to $X_4$ is N, the rest are $CR_a$, or each of $X_1$ and $X_4$ among $X_1$ to $X_4$ is N, the rest are $CR_a$, Y is O or S, n is 1 or 2, L is an unsubstituted phenylene or an unsubstituted pyridinylene, $R_a$ is a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or is combined with an adjacent group to form a ring, and Ar is represented by Formula 2 below:

Formula 2

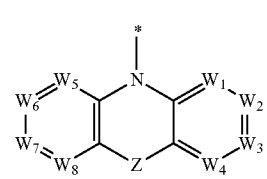

in Formula 2, $W_1$ to $W_8$ are each independently N or $CR_b$,

Z is a direct linkage, O, or $CR_cR_d$, and $R_b$ to $R_d$ are each independently a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or are combined with an adjacent group to form a ring.

106

11. The compound of claim 10, wherein Formula 1 above is represented by the following Formula 1-1 or Formula 1-2:

Formula 1-1

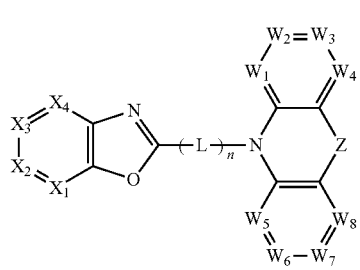

Formula 1-2

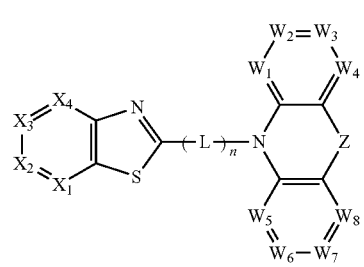

in Formula 1-1 and Formula 1-2, $X_1$ to $X_4$, L, n, Z, and $W_1$ to $W_8$ are the same as those defined with respect to Formula 1 and Formula 2 above.

12. The compound of claim 10, wherein any one selected from among $X_1$ to $X_4$ is N, the rest are $CR_a$, or each of $X_1$ and $X_4$ among $X_1$ to $X_4$ is N, the rest are $CR_a$, and $R_a$ is a hydrogen atom, or represented by any one selected from the following $R_a$-1 to $R_a$-4:

$R_a$-1

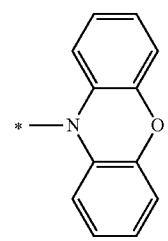

$R_a$-2

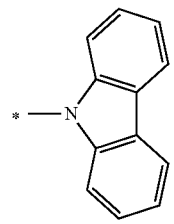

-continued

R<sub>a</sub>-3

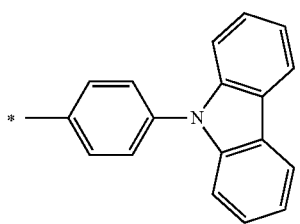

R<sub>a</sub>-4

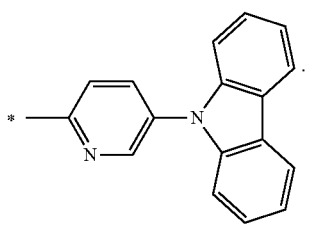

13. The compound of claim 10,
wherein Formula 2 is represented by any one selected from the following Formula 2-1 to Formula 2-4:

Formula 2-1

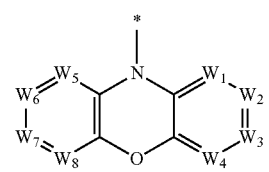

Formula 2-2

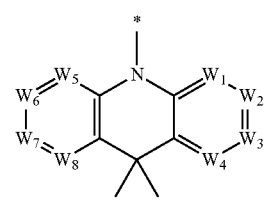

Formula 2-3

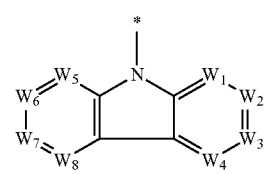

Formula 2-4

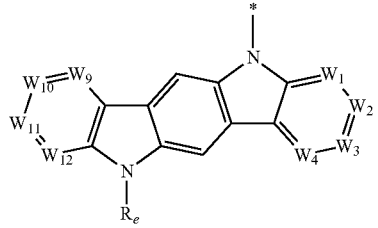

in Formula 2-4,
R$_e$ is a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, W$_9$ to W$_{12}$ are each independently N or CR$_f$, R$_f$ is a hydrogen atom, a deuterium atom, a halogen atom, a cyano group, a substituted or unsubstituted silyl group, a substituted or unsubstituted amine group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or are combined with an adjacent group to form a ring, and in Formula 2-1 to Formula 2-4, W$_1$ to W$_8$ are the same as those defined with respect to Formula 2 above.

14. The compound of claim 10,
wherein Ar is represented by any one selected from the following Ar-1 to Ar-6:

Ar-1

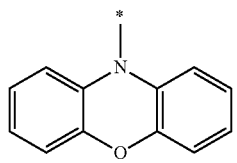

Ar-2

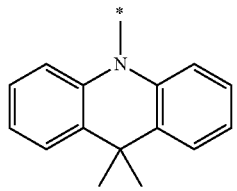

Ar-3

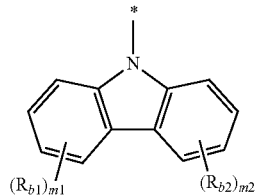

Ar-4

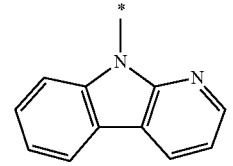

Ar-5

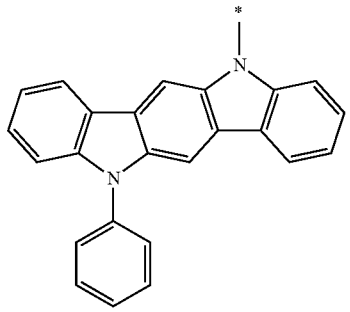

Ar-6

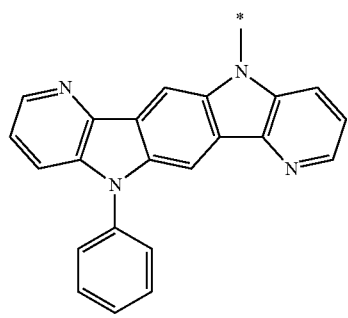

in Ar-3, m1 and m2 are each independently 0 or 1, and $R_{b1}$ and $R_{b2}$ are each independently a hydrogen atom, a deuterium atom, a substituted or unsubstituted arylamine group having 6 to 30 carbon atoms for forming a ring, or a substituted or unsubstituted aryl group having 6 to 30 carbon atoms for forming a ring.

15. The compound of claim 10, wherein L is represented by any one selected from the following L-1 and L-2:

L-1

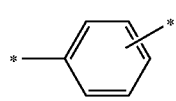

L-2

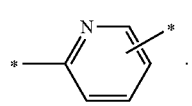

16. The compound of claim 10, wherein the compound represented by Formula 1 is a green dopant to emit green light having a center wavelength of 500 nm or more and 550 nm or less.

17. The compound of claim 10, wherein the compound represented by Formula 1 is a blue dopant to emit blue light having a center wavelength of 450 nm or more and less than 500 nm.

18. The compound of claim 10, wherein the compound represented by Formula 1 is a host material.

19. The compound of claim 10, wherein the compound represented by Formula 1, the absolute value of a difference ($\Delta E_{ST}$) between a lowest singlet excitation energy level (S1) and a lowest triplet excitation energy level (T1) is 0.2 eV or less.

20. The compound of claim 10, wherein the compound represented by Formula 1 is represented by any one selected from compounds represented in the following Compound Group 1 or Compound Group 2:

Compound Group 1

1-1

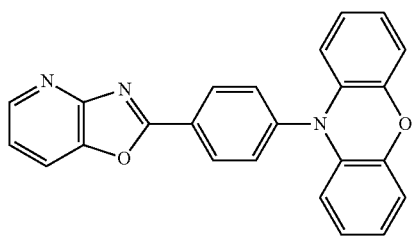

1-2

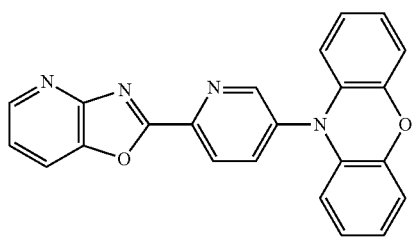

1-3

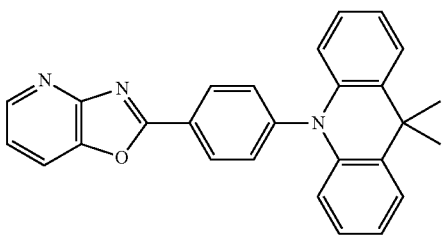

1-4

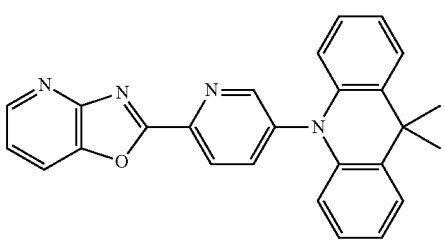

1-5

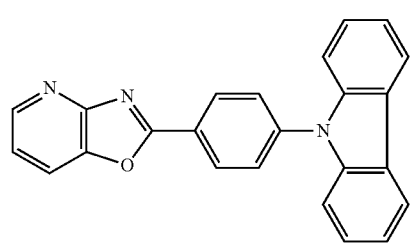

1-6

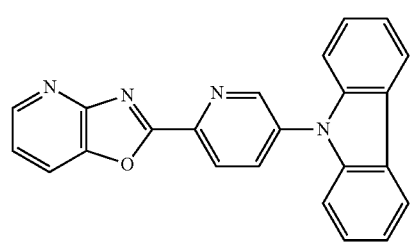

1-7
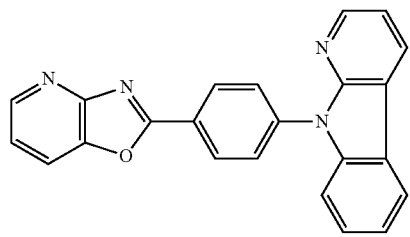
1-8
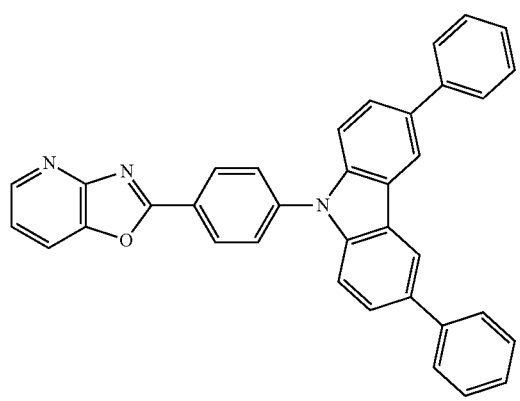
1-9
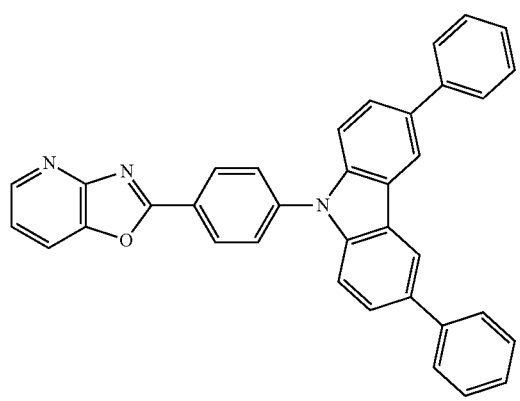
1-10
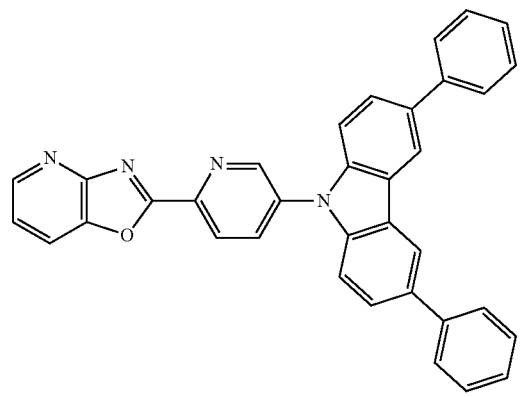
1-11
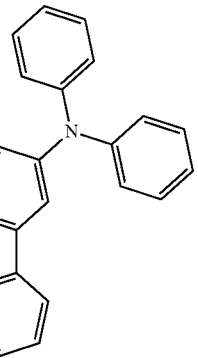
1-12
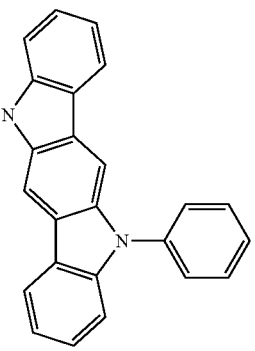
1-13
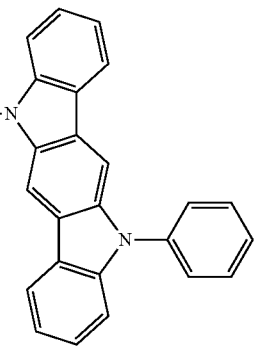
1-14
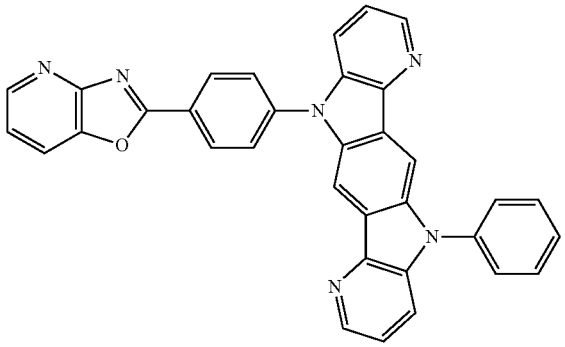

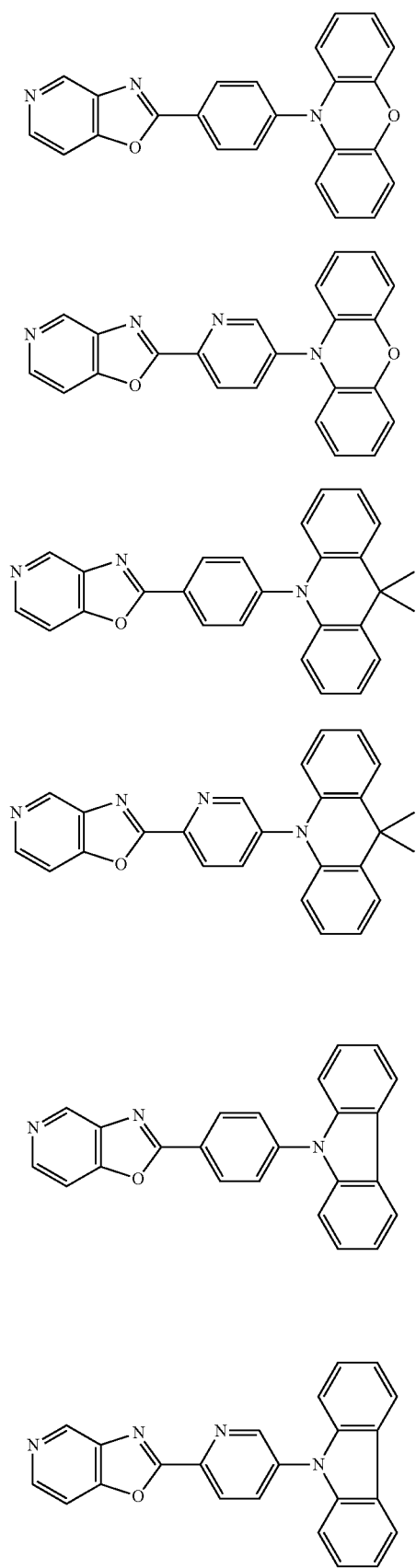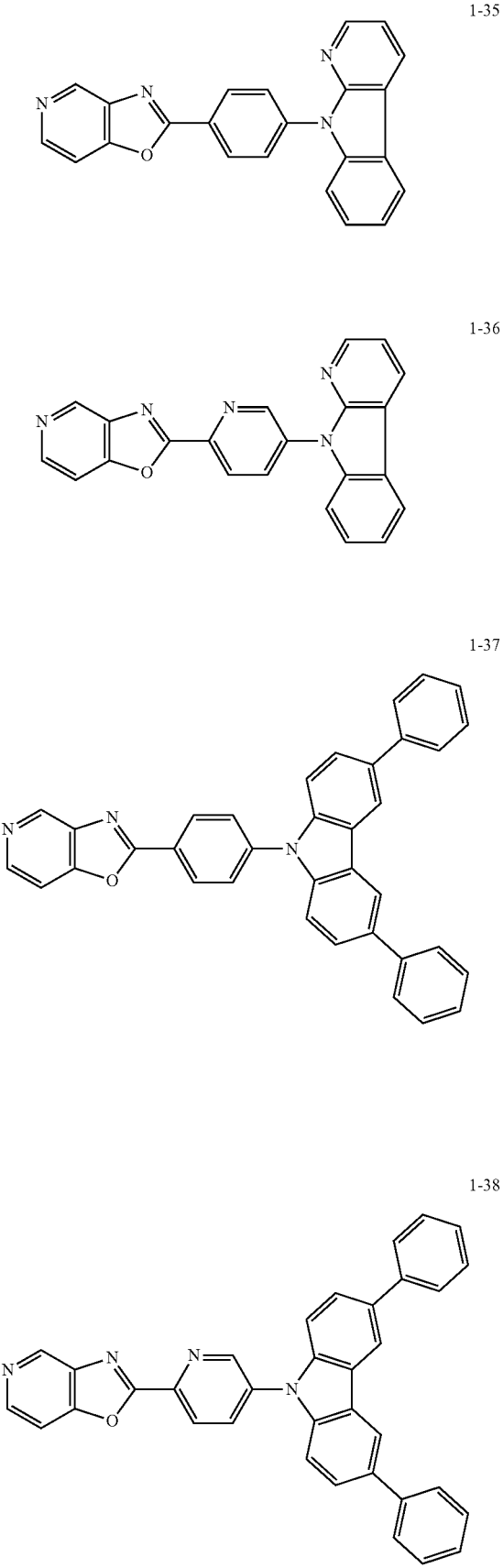

1-39
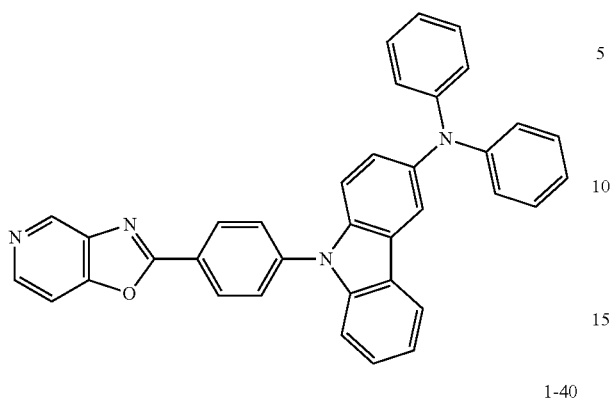
1-40
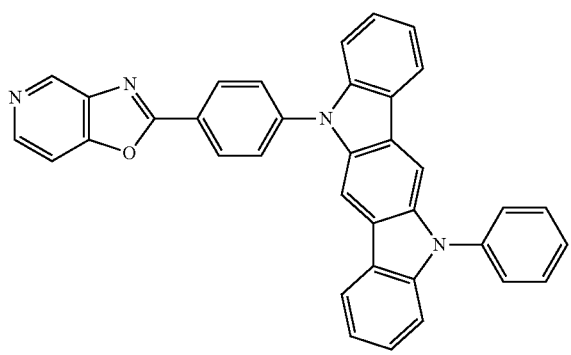
1-41
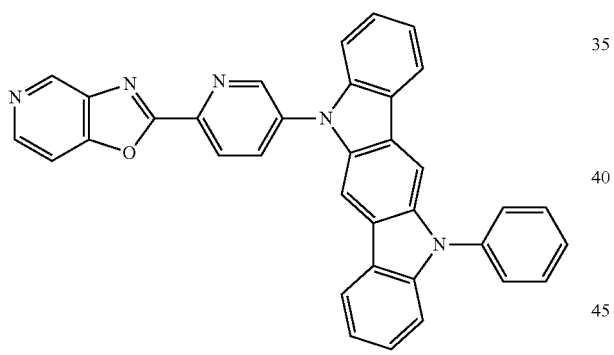
1-42
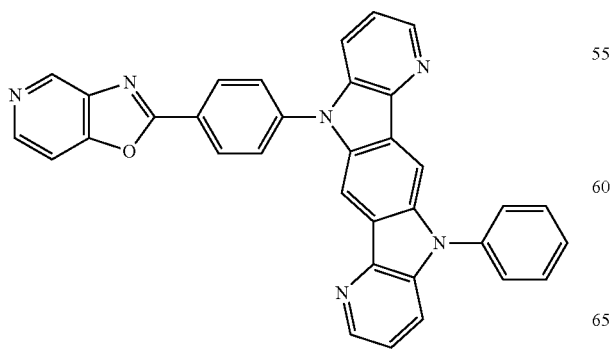
1-43
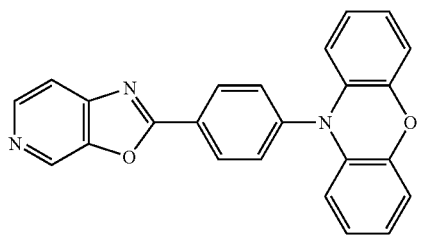
1-44
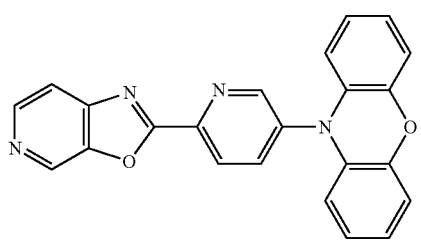
1-45
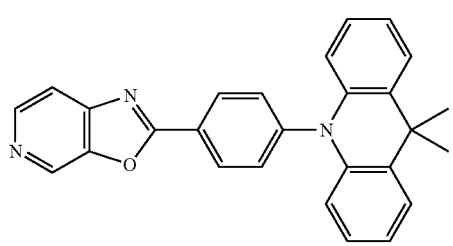
1-46
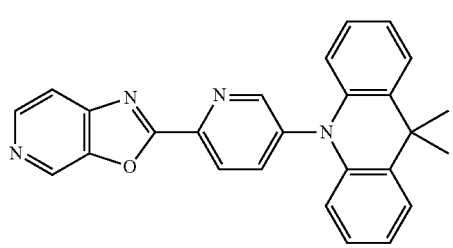
1-47
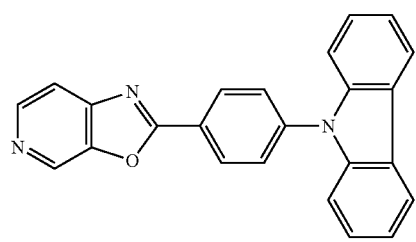
1-48
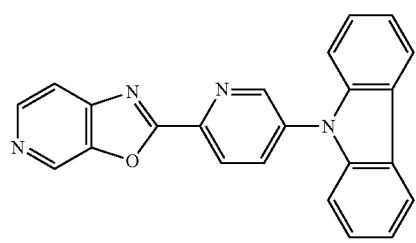

1-49
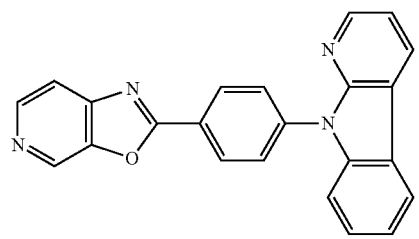
1-50
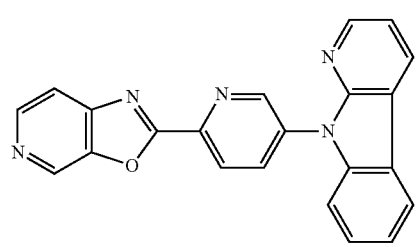
1-51
1-52
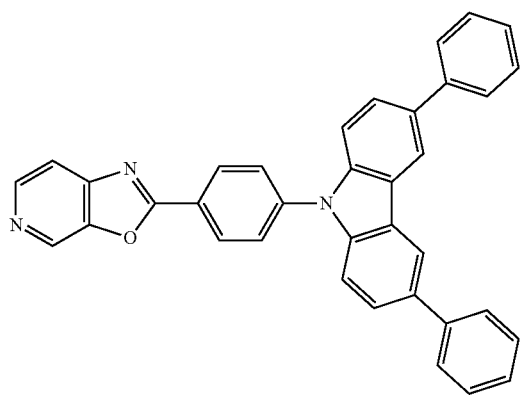
1-53
1-54
1-55
1-56
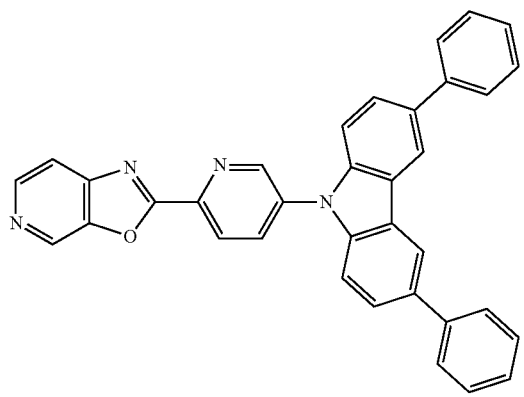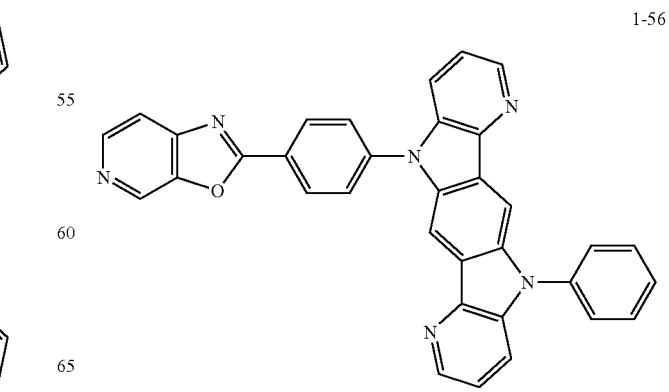

1-57
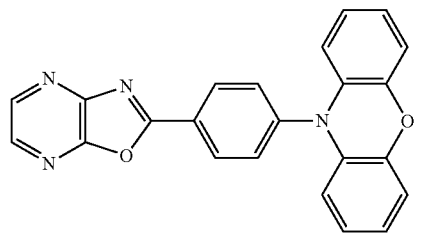
1-58
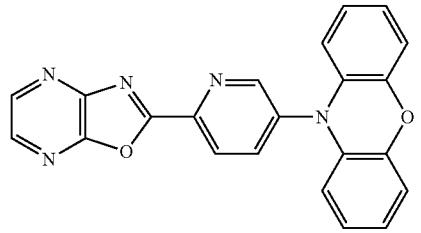
1-59
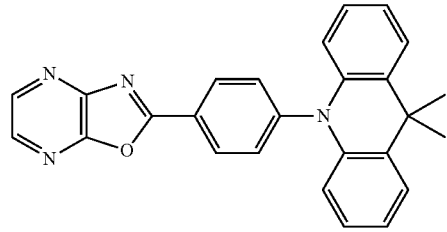
1-60
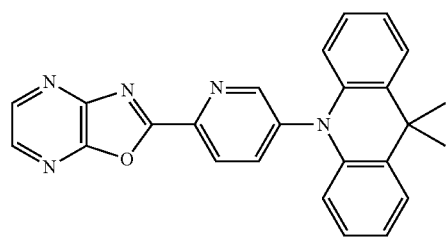
1-61
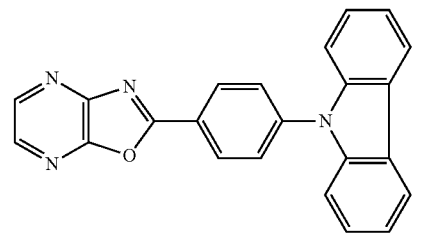
1-62
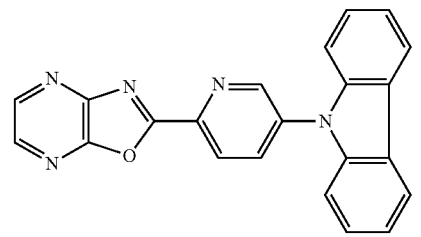
1-63
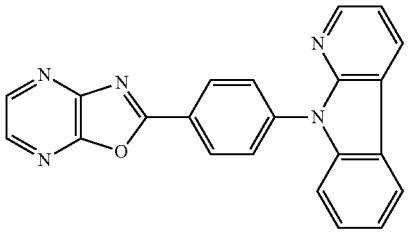
1-64
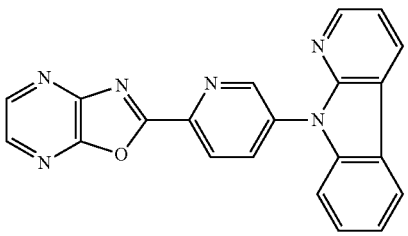
1-65
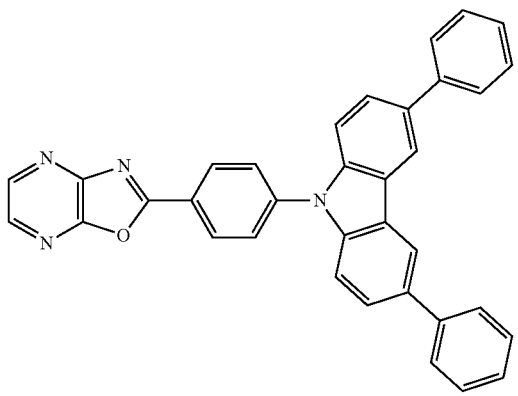
1-66
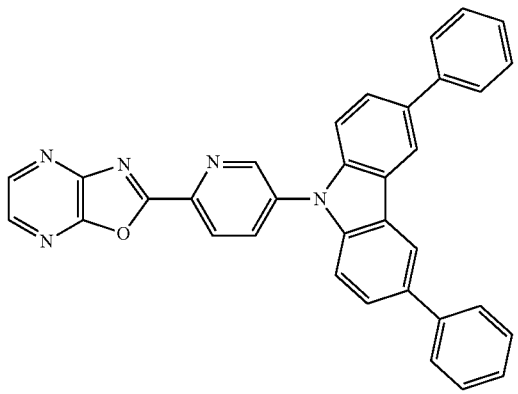

1-67
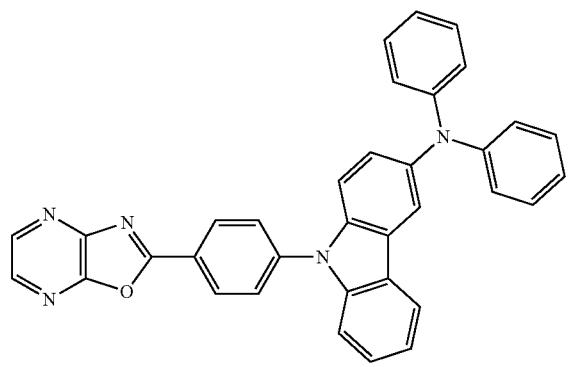
1-68
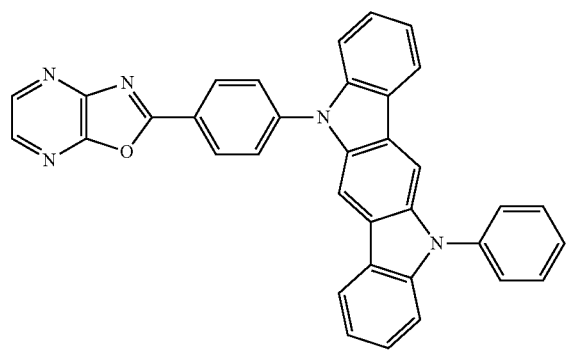
1-69
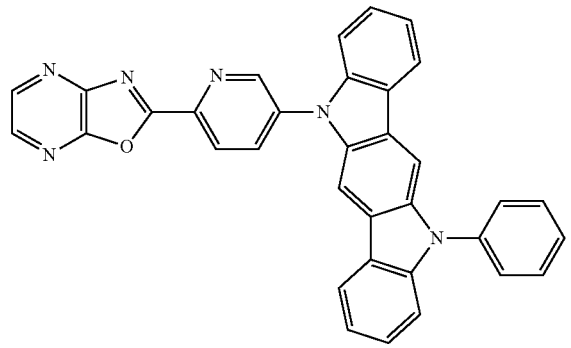
1-70
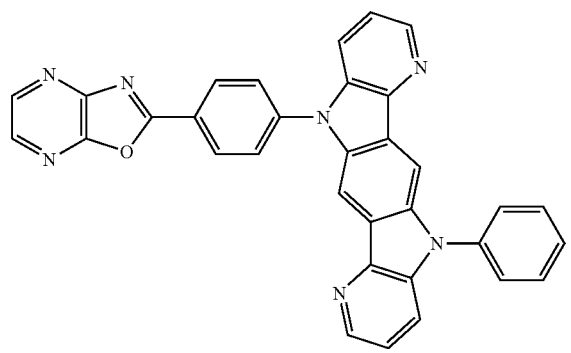
1-71
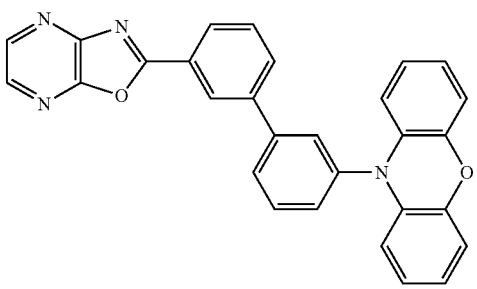
1-72
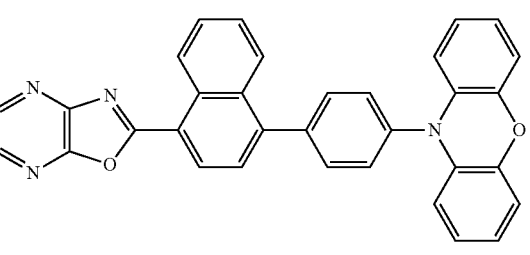
1-73
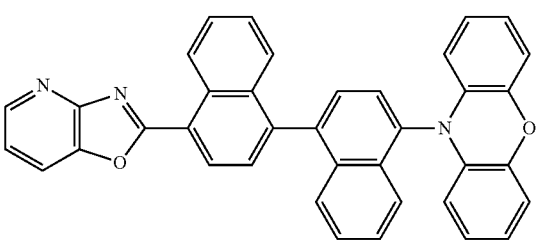
1-74
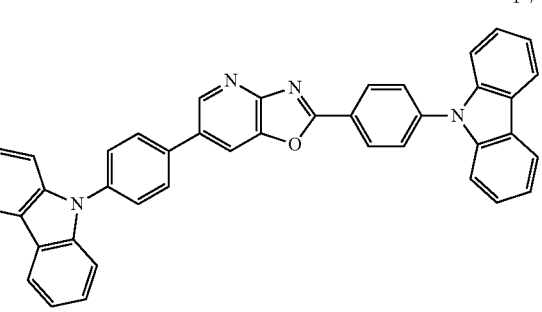
1-75
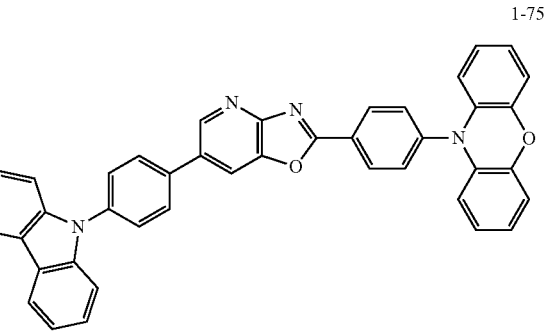

1-76
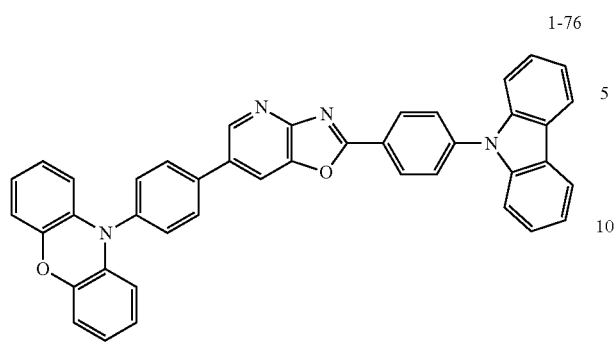
1-80
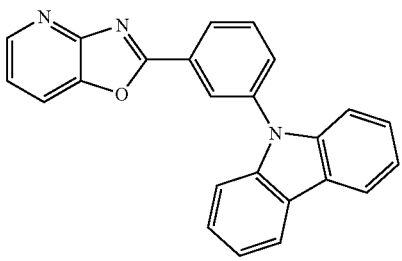
Compound Group 2
1-77
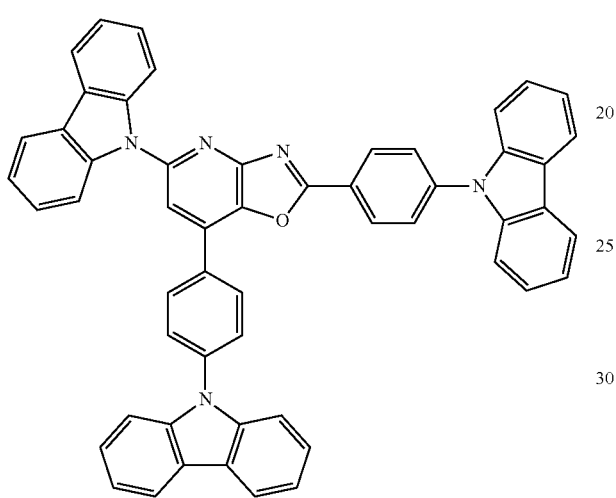
2-1
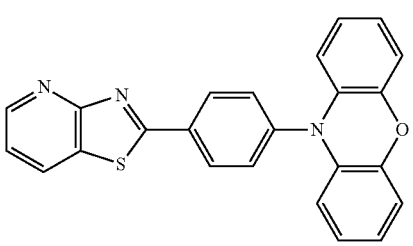
2-2
2-3
2-4
1-78
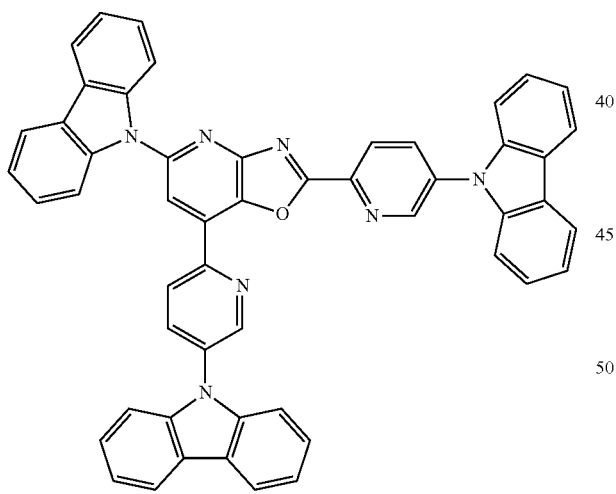
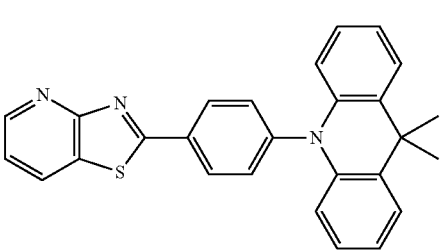
1-79
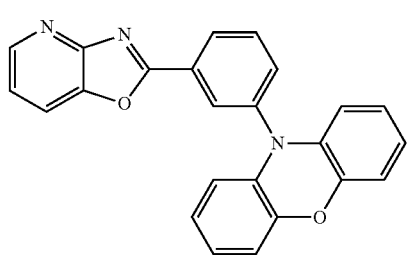
2-5
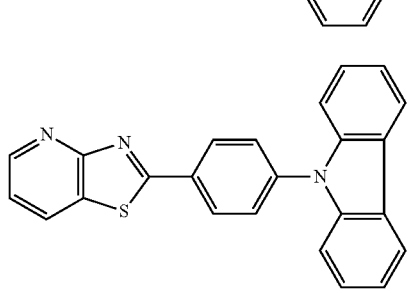

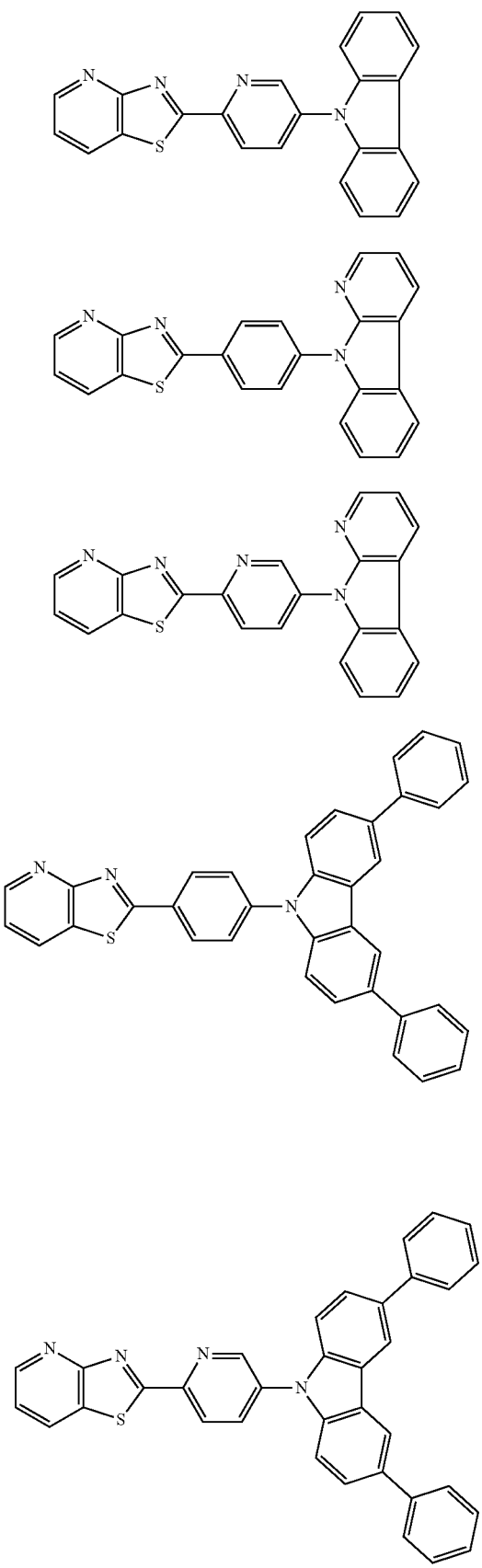

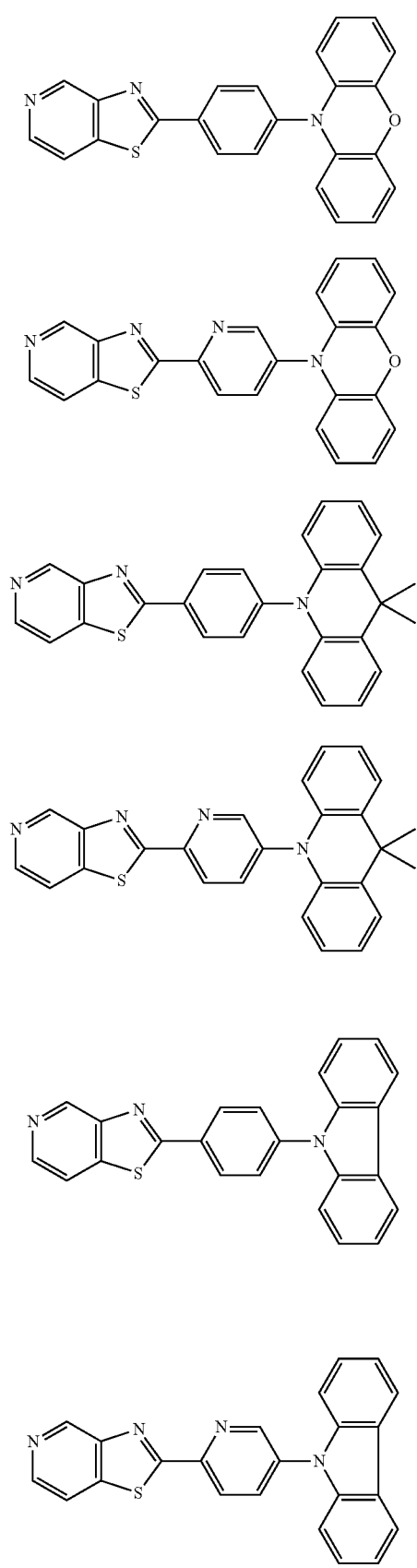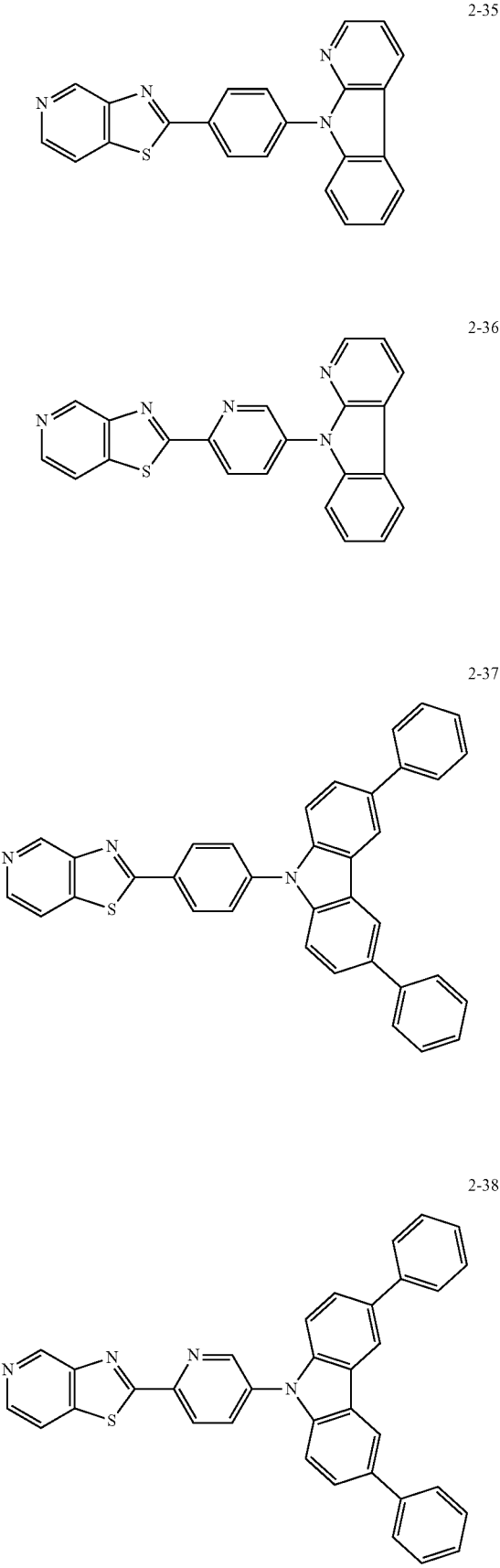

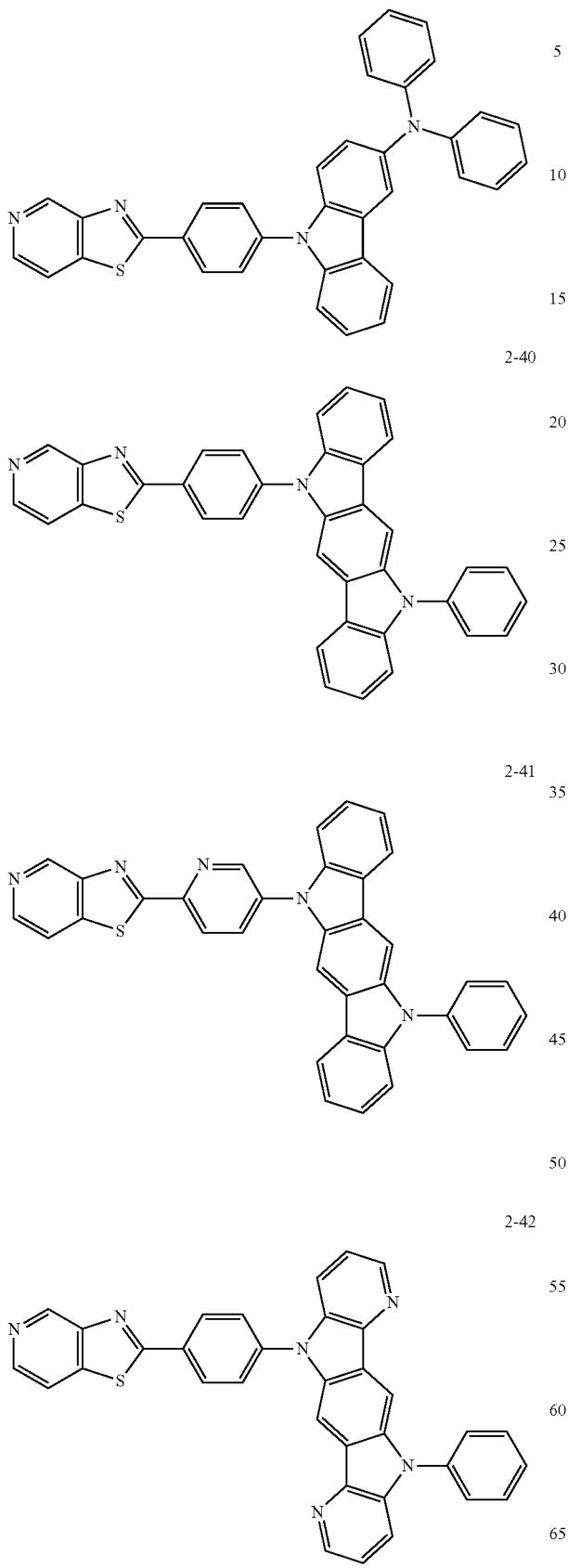
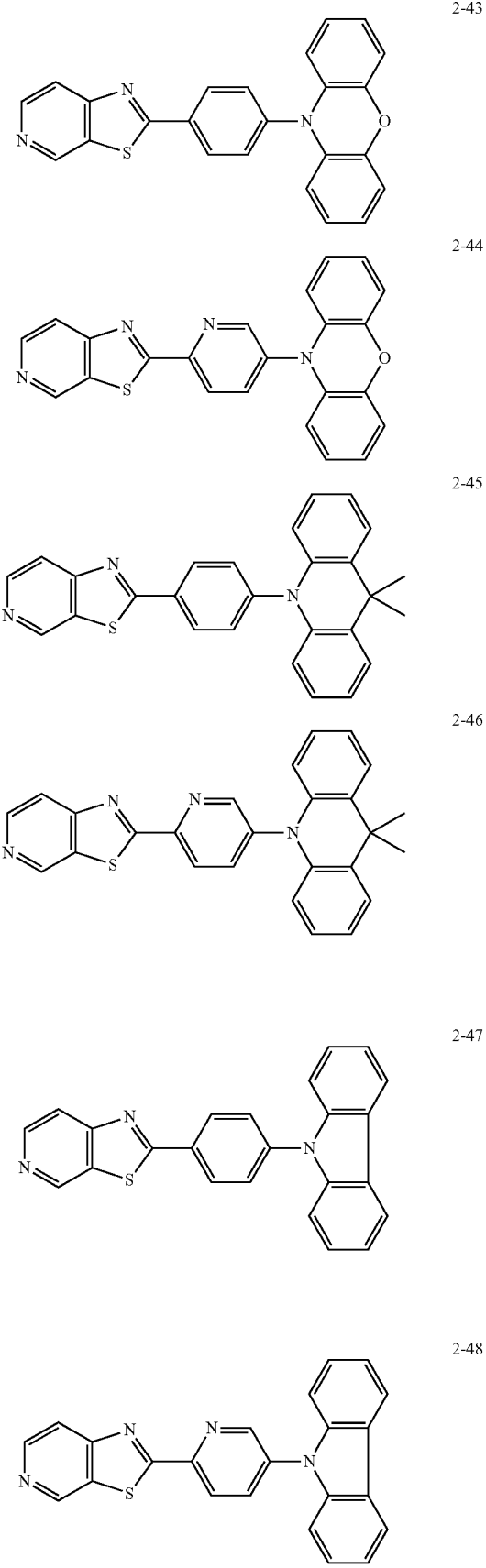

2-49
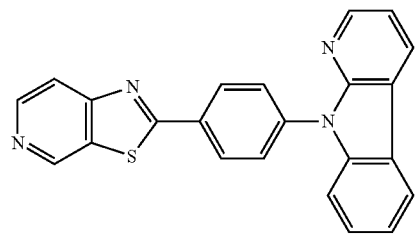
2-50
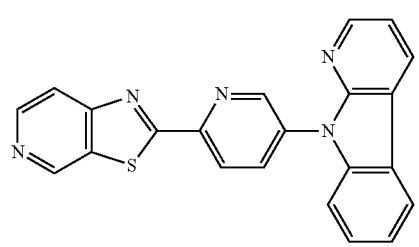
2-51
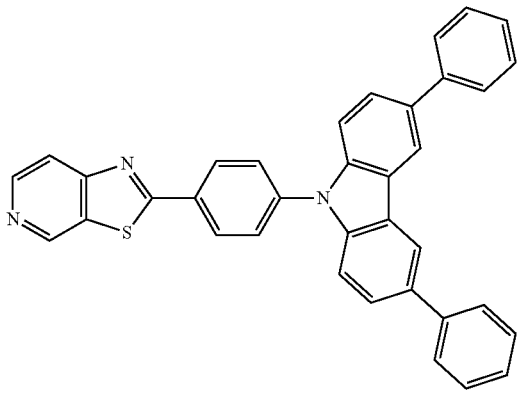
2-52
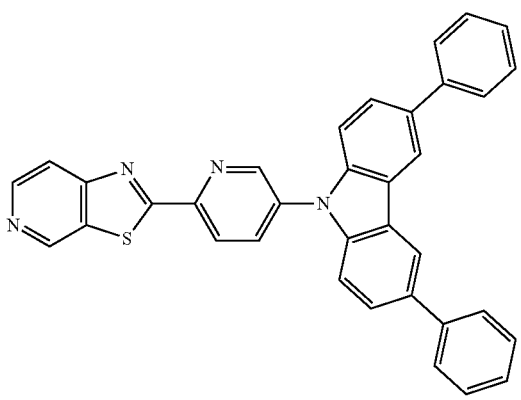
2-53
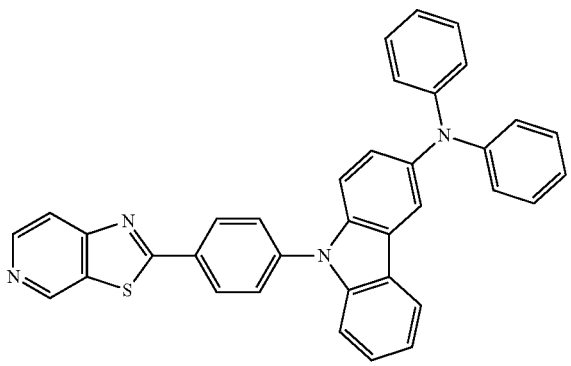
2-54
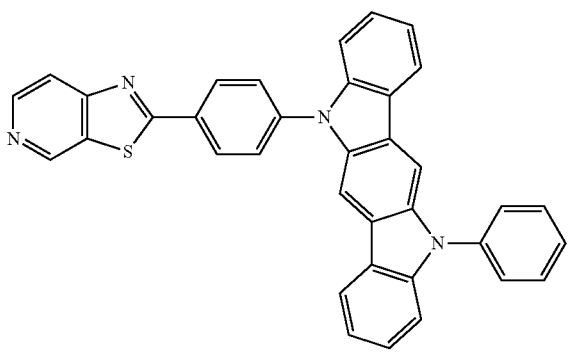
2-55
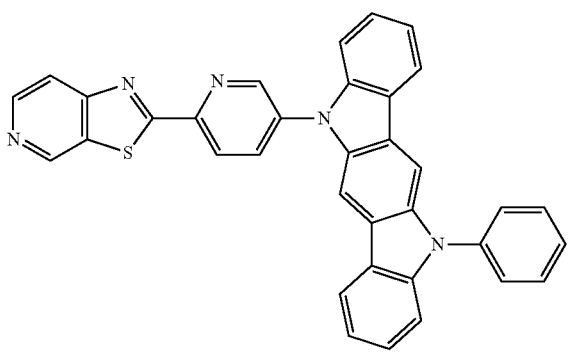
2-56
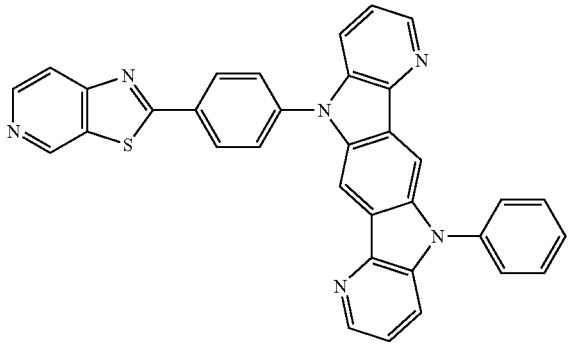

-continued
2-57
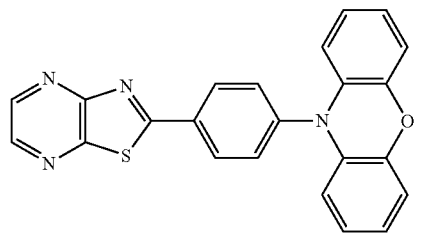
2-58
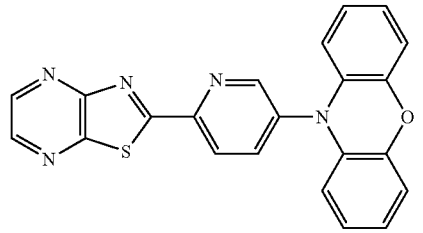
2-59
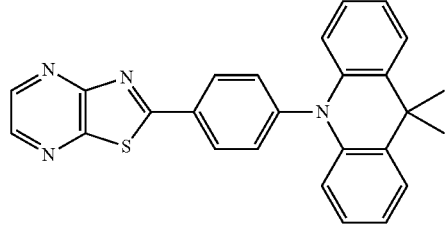
2-60
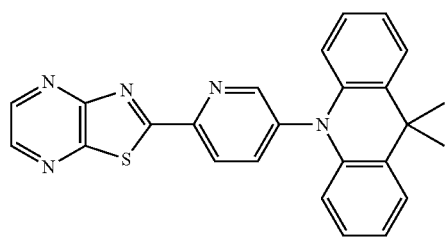
2-61
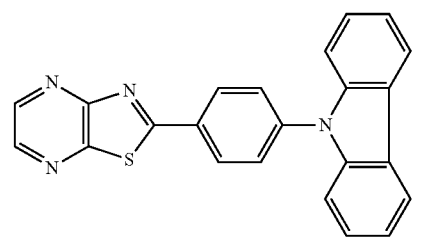
2-62
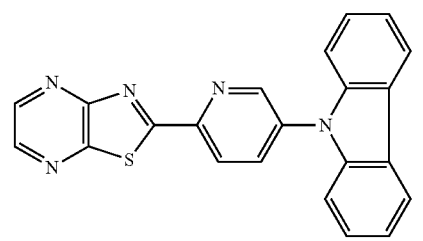
-continued
2-63
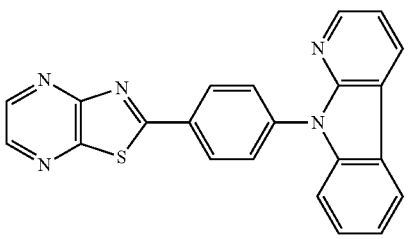
2-64
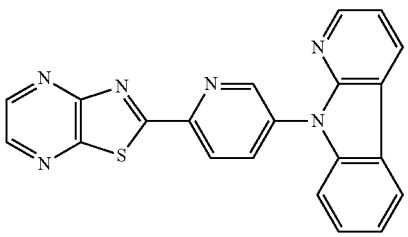
2-65
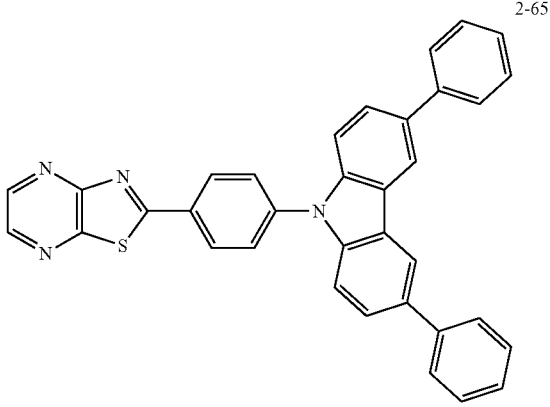
2-66
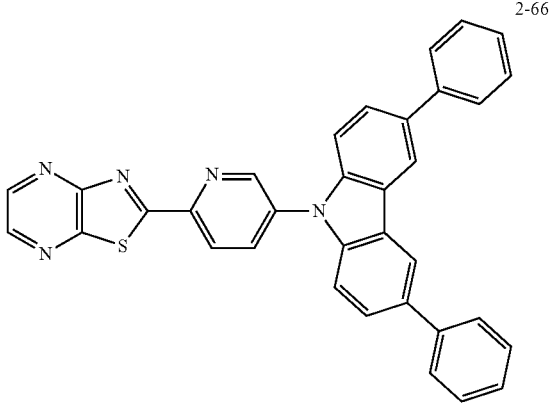

2-67
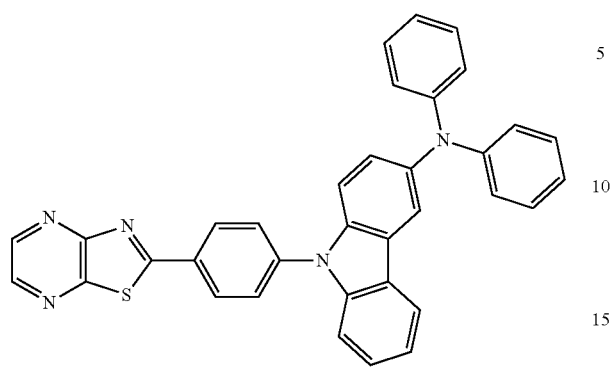
2-68
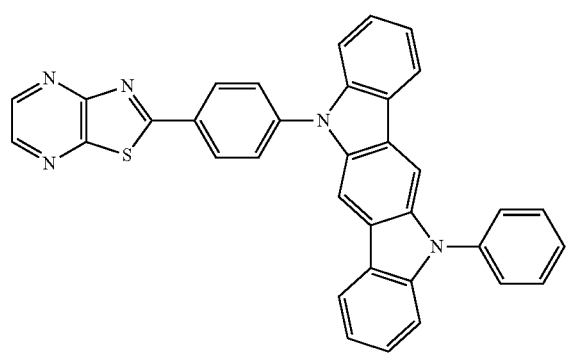
2-69
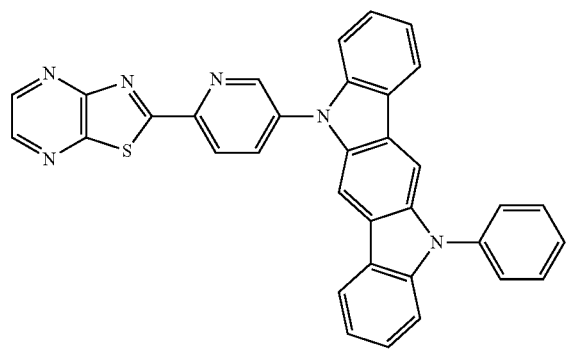
2-70
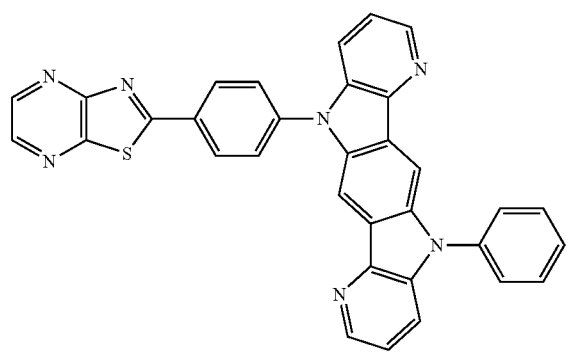
2-71
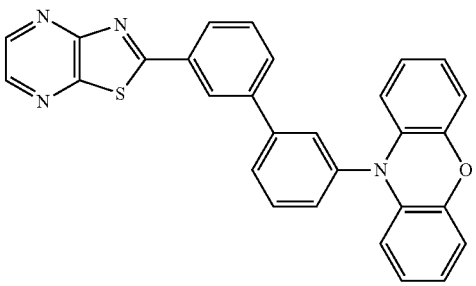
2-72
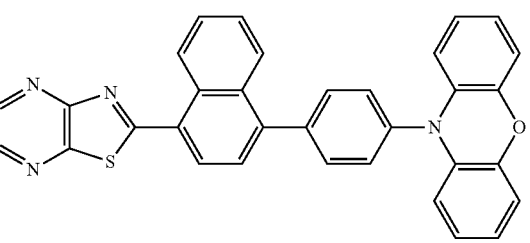
2-73
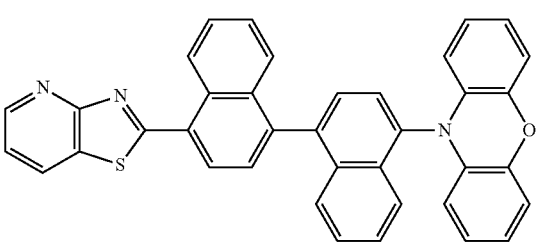
2-74
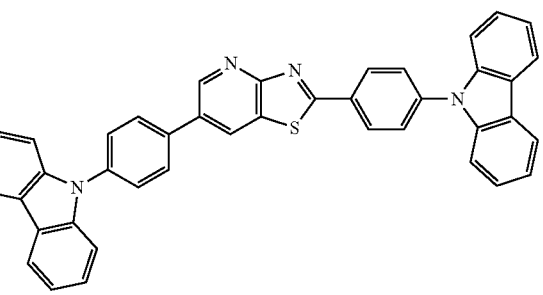
2-75
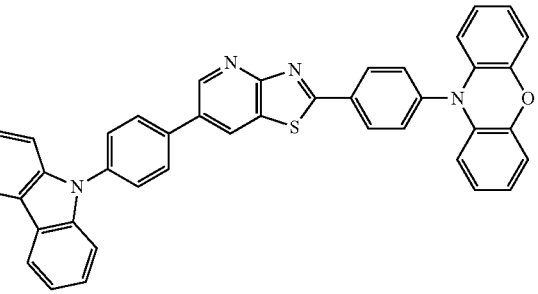

2-76
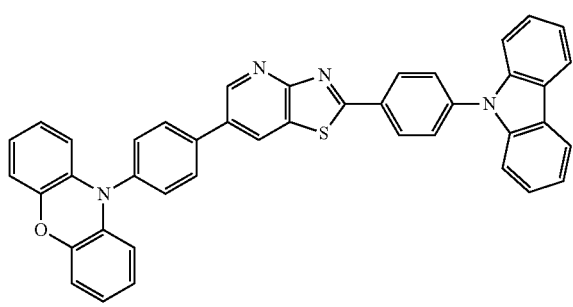
2-77
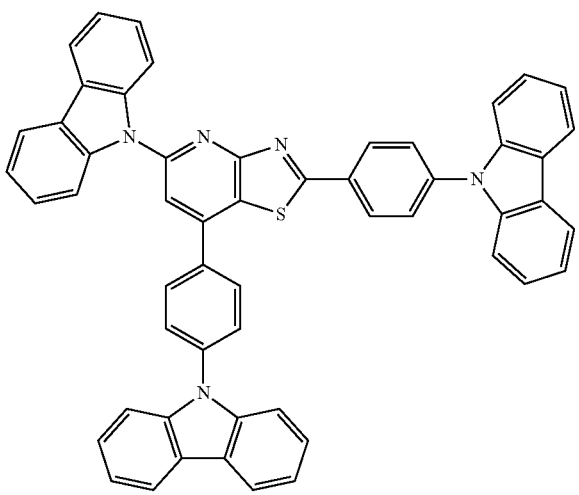
2-78
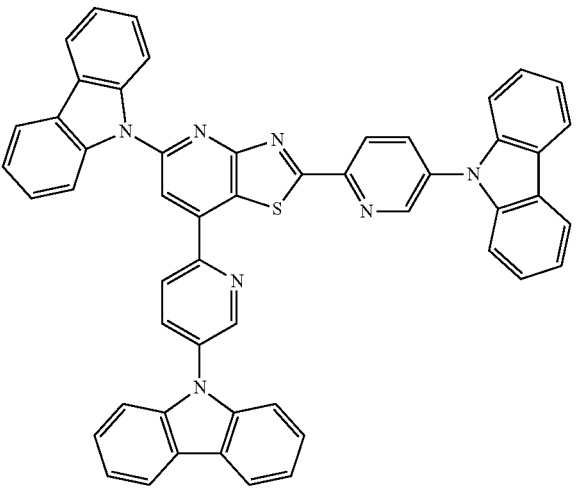
2-79
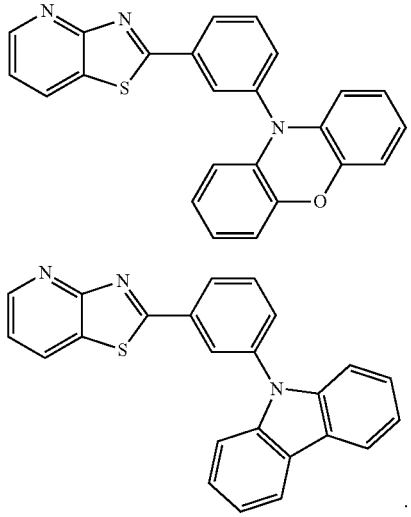
2-80
* * * * *